US011407786B2

(12) United States Patent
Lu et al.

(10) Patent No.: US 11,407,786 B2
(45) Date of Patent: *Aug. 9, 2022

(54) COMPOSITIONS AND METHODS FOR THE DELIVERY OF NUCLEIC ACIDS

(71) Applicant: CASE WESTERN RESERVE UNIVERSITY, Cleveland, OH (US)

(72) Inventors: Zheng-Rong Lu, Beachwood, OH (US); Amita M. Vaidya, Cleveland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 371 days.

This patent is subject to a terminal disclaimer.

(21) Appl. No.: 16/588,362

(22) Filed: Sep. 30, 2019

(65) Prior Publication Data

US 2020/0031865 A1    Jan. 30, 2020

Related U.S. Application Data

(63) Continuation-in-part of application No. 14/743,298, filed on Jun. 18, 2015, now Pat. No. 11,129,845.

(60) Provisional application No. 62/738,677, filed on Sep. 28, 2018.

(51) Int. Cl.
*A61K 48/00* (2006.01)
*C12N 15/113* (2010.01)
*C07K 5/062* (2006.01)
*C12N 15/11* (2006.01)

(52) U.S. Cl.
CPC .......... *C07K 5/0606* (2013.01); *C12N 15/111* (2013.01); *C12N 2310/14* (2013.01); *C12N 2310/3513* (2013.01); *C12N 2320/32* (2013.01)

(58) Field of Classification Search
None
See application file for complete search history.

(56) References Cited

U.S. PATENT DOCUMENTS

| 5,622,718 | A | 4/1997 | Al-Shamkhani et al. |
| 5,700,848 | A | 12/1997 | Soon-Shong et al. |
| 6,472,506 | B1 | 10/2002 | Moreau et al. |
| 2003/0161791 | A1 | 8/2003 | Bentley et al. |
| 2004/0028745 | A1 | 2/2004 | Bouhadir et al. |
| 2005/0271705 | A1 | 12/2005 | Hughes et al. |
| 2008/0221208 | A1 | 9/2008 | Palczewski et al. |
| 2010/0035986 | A1 | 2/2010 | Maeda et al. |
| 2011/0288170 | A1 | 11/2011 | Palczewski et al. |

FOREIGN PATENT DOCUMENTS

| CN | 101745119 A | 6/2010 |
| EP | 3223016 A1 | 9/2017 |
| GB | 1334980 A | 10/1973 |
| WO | 2008/042686 A3 | 10/2008 |
| WO | 2010/062502 A1 | 6/2010 |

OTHER PUBLICATIONS

Lai et al., Med. Oncol., 2012, 29: 1810-1816.*
Zonghua Liu, et al.; "Polysaccharides-based nanoparticles as drug delivery systems"; Advanced Drug Delivery Reviews; Journal; www.elsevier.com/locate/addr; Sep. 17, 2008; 13 pgs.
Applicant: Case Western Reserve University; "International Search Report and Written Opinion"; International PCT Application No. PCT/US2012/066847; International Filing Date: Nov. 28, 2012; dated Mar. 18, 2013; 13 pgs.
Wang et al., Biomaterials, 2008, 29: 15-22.
Wang etal., Bioconj. Chem., 2007, 18: 2169-2177.
Wang et al., Mol. Pharm., 2009, 6: 738-746.
Malamasetal.,J.Control. Release,onlineJun. 21, 2013, 171:296-307.
Zalipsky et al., Bioconj. Chem., 1995, 6: 705-708.
Kummitha et al 2012, Int. J. Nanomed. 7:5205-5214.
Applicant: Case Western Reserve University; International Application No. 19211484.1; Filing Date: Nov. 26, 2019; European Search Report; Date of Completion: May 27, 2020; 11 pgs.
Yujin Sun, et al.: "MRI of Breast Tumor Initiating Cells Using the Extra Comain-B of Fibronectin Targeting Nanoparticles", Theranostics, vol. 4, No. 8, Jan. 1, 2014, pp. 845-857, XP055432454, au issn: 1838-7460, doi: 10.7150/thno.8343.
Wang, Wei, et al.: "Screening and identifying of homing peptides to bladder cancer BIU-87 cells in Chinese", Chin. J. Cancer Biother., vol. 20, No. 5, Oct. 2013, pp. 515-521, XP002776454, abstract; figures 2-3.
Zheng Han, et al.: "EDB Fribronectin Specific Peptide for Prostate Cancer Targeting", Bioconjugate Chemistry, vol. 26, No. 5, May 20, 2015, pp. 830-838, XP055432466, ISSN: 1043-1802, DOI: 10.1021/acs.bioconjchem.5b00178.
Zheng Han et al.: "An EDB fibronectin specific contrast agent for molecular imaging of cancer metastasis" 23rd Annual Meeting & Exhibition May 30-Jun. 2015, Proc. Intl. Soc. Mag. Reson. Med., vol. 23, Jun. 3, 2015, XP009502183, Retrieved from the Internet: URL: http://dev.ismrm.org/2015/1910.html [retrieved on Dec. 6, 2015].

* cited by examiner

*Primary Examiner* — Ileana Popa
(74) *Attorney, Agent, or Firm* — Tarolli, Sundheim, Covell & Tummino LLP

(57) ABSTRACT

A nanosized complex includes siRNA and a compound comprising formula (I):

$$R^4S-\overset{\underset{NH}{|}}{C}\overset{O}{\|}-\overset{H}{N}\underset{a}{\frown}\overset{H}{N}-\overset{O}{\|}-\overset{R^1}{\underset{|}{N}}\underset{c}{\frown}\overset{H}{N}-\overset{O}{\|}-\overset{H}{N}\underset{b}{\frown}\overset{H}{N}-\overset{O}{\|}-\overset{|}{C}-SR^5$$
$$\underset{R^2}{|}\qquad\qquad\qquad\qquad\qquad\qquad\qquad\underset{R^3}{|}$$

20 Claims, 32 Drawing Sheets

Specification includes a Sequence Listing.

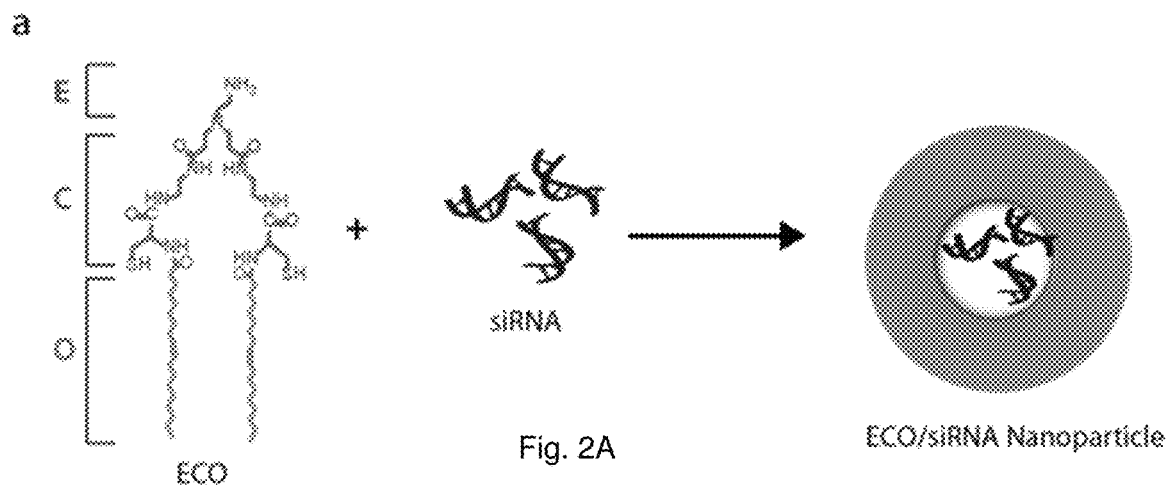
Fig. 2A
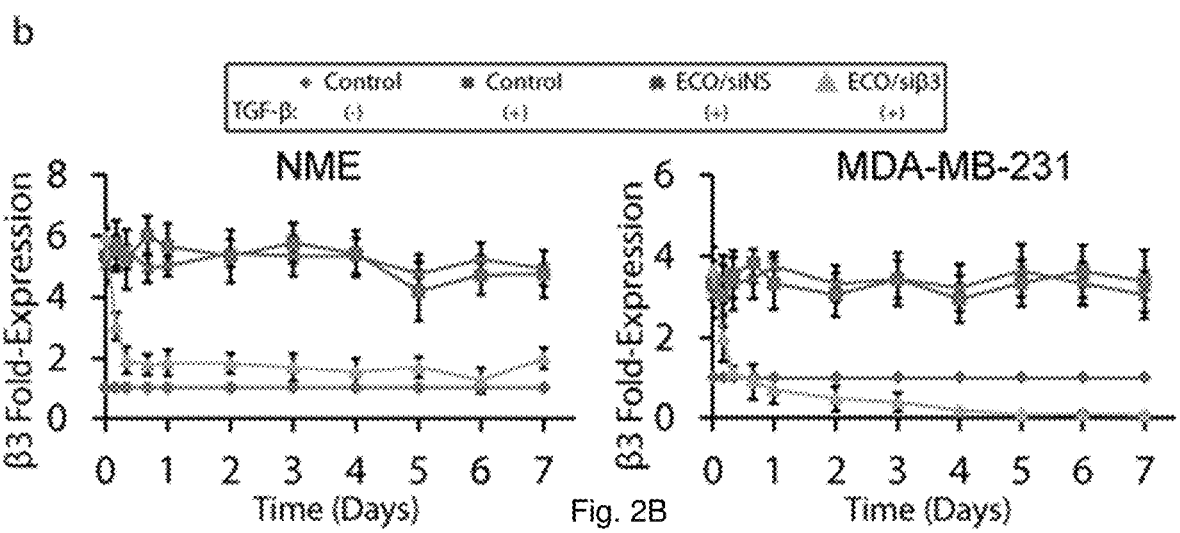
Fig. 2B
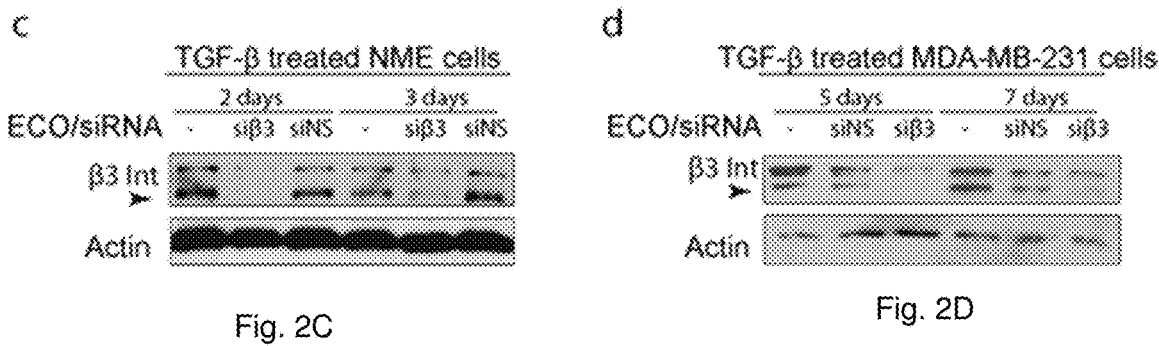
Fig. 2C
Fig. 2D a

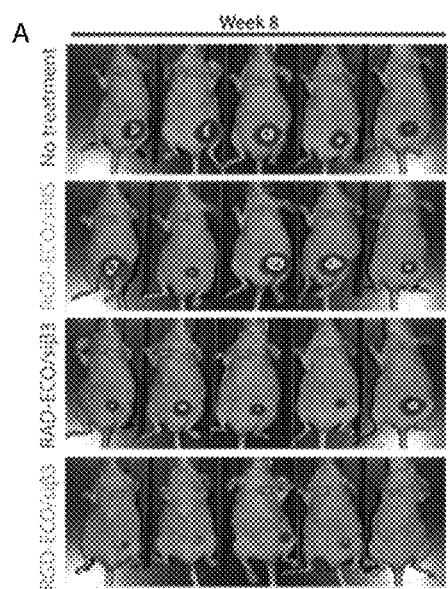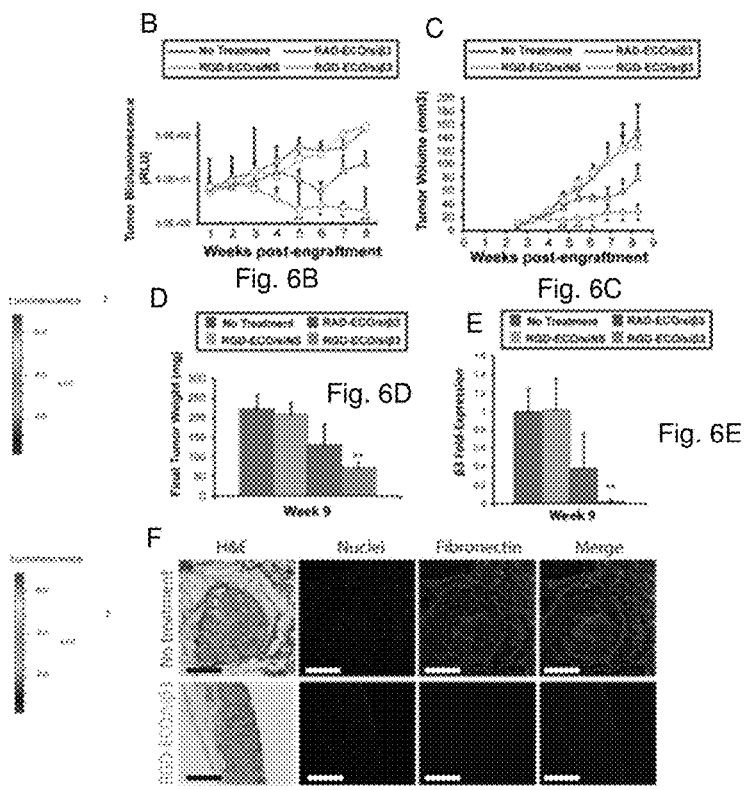
Fig. 6A  Fig. 6B  Fig. 6C  Fig. 6D  Fig. 6E  Fig. 6F

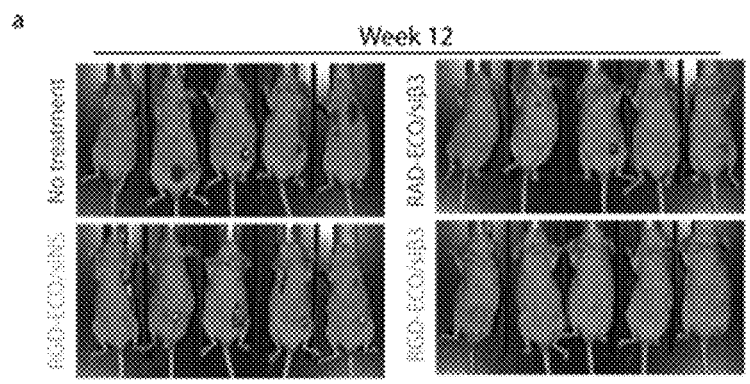
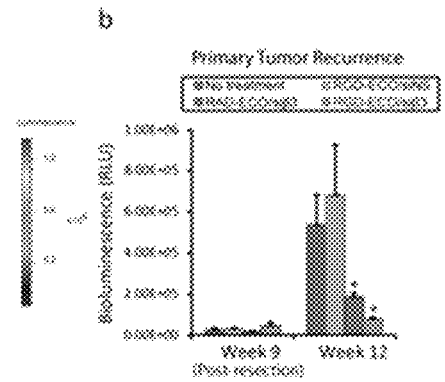
Fig. 7A
Fig. 7B
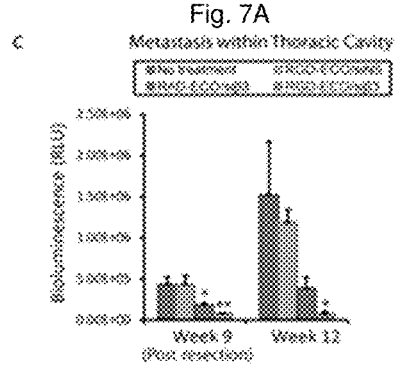
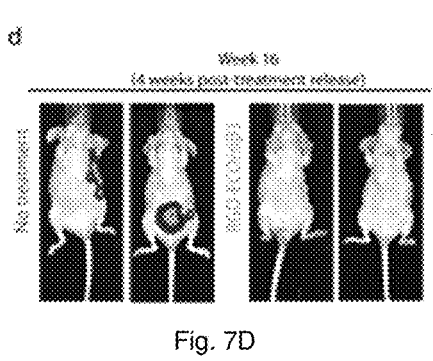
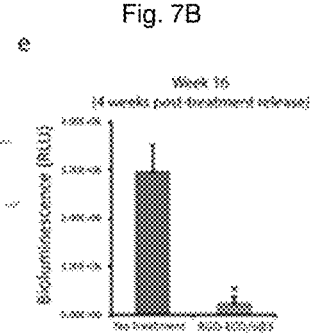
Fig. 7C
Fig. 7D
Fig. 7E

A

B

C

D

Time (h)

EC, Extracellular space; IC, Intracellular space; NP, Nanoparticles; INT, Integrins; V, Vesicle; EE, Early endosome; LE, Late endosome; LY, Lysosome; lncR, lncRNA; RISC, RNA-induced silencing complex

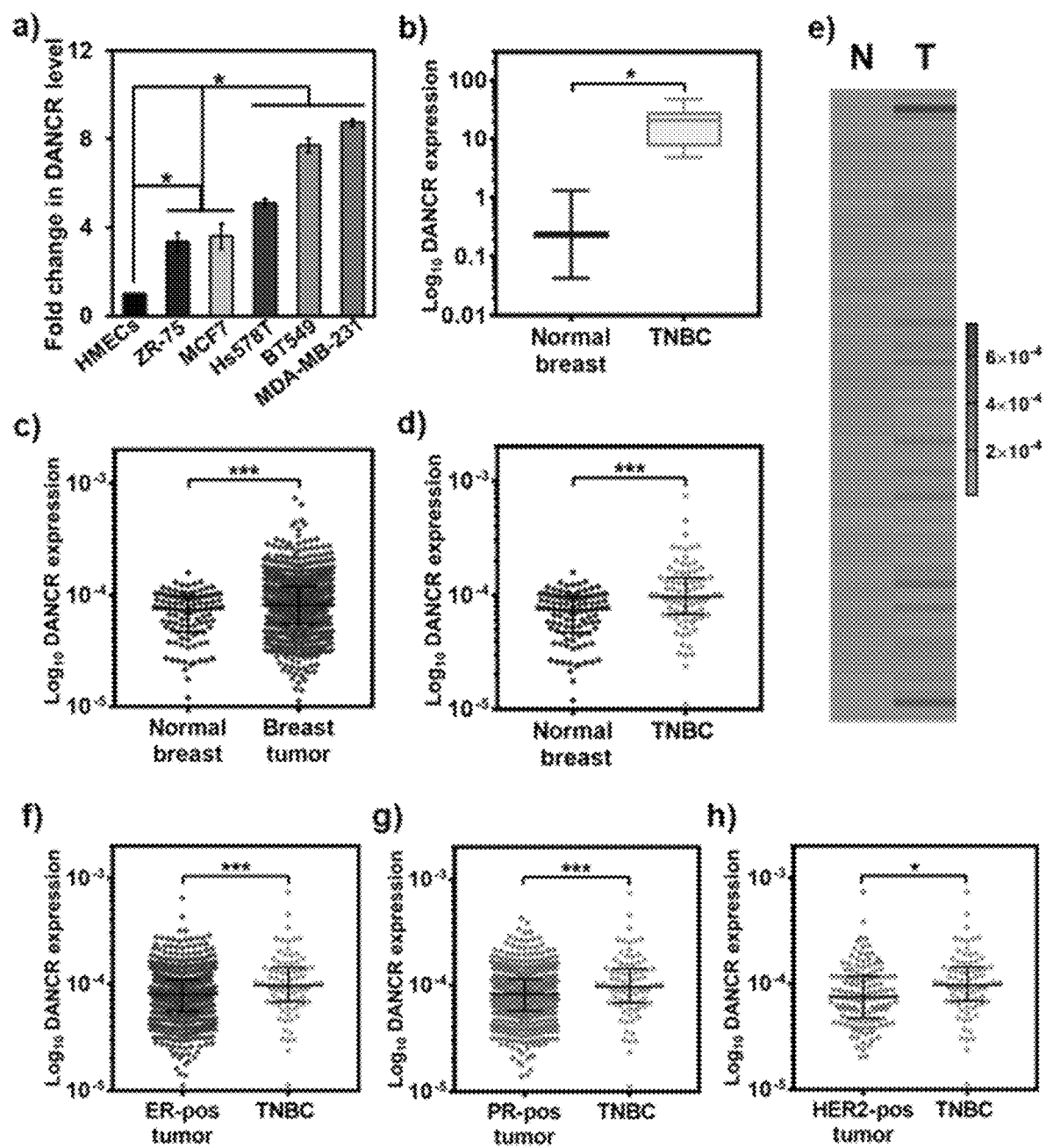
Fig. 15A-H

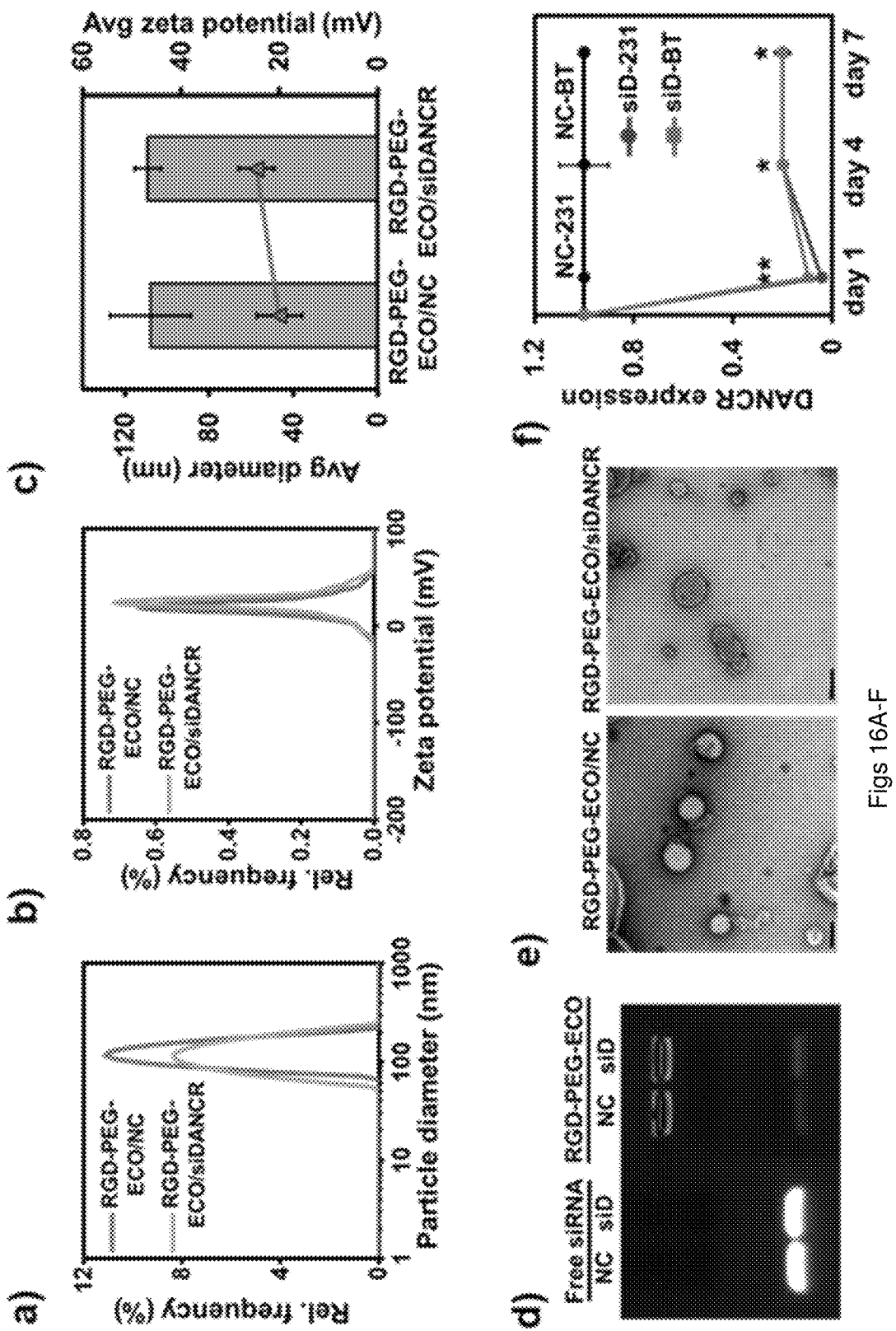
Figs 16A-F

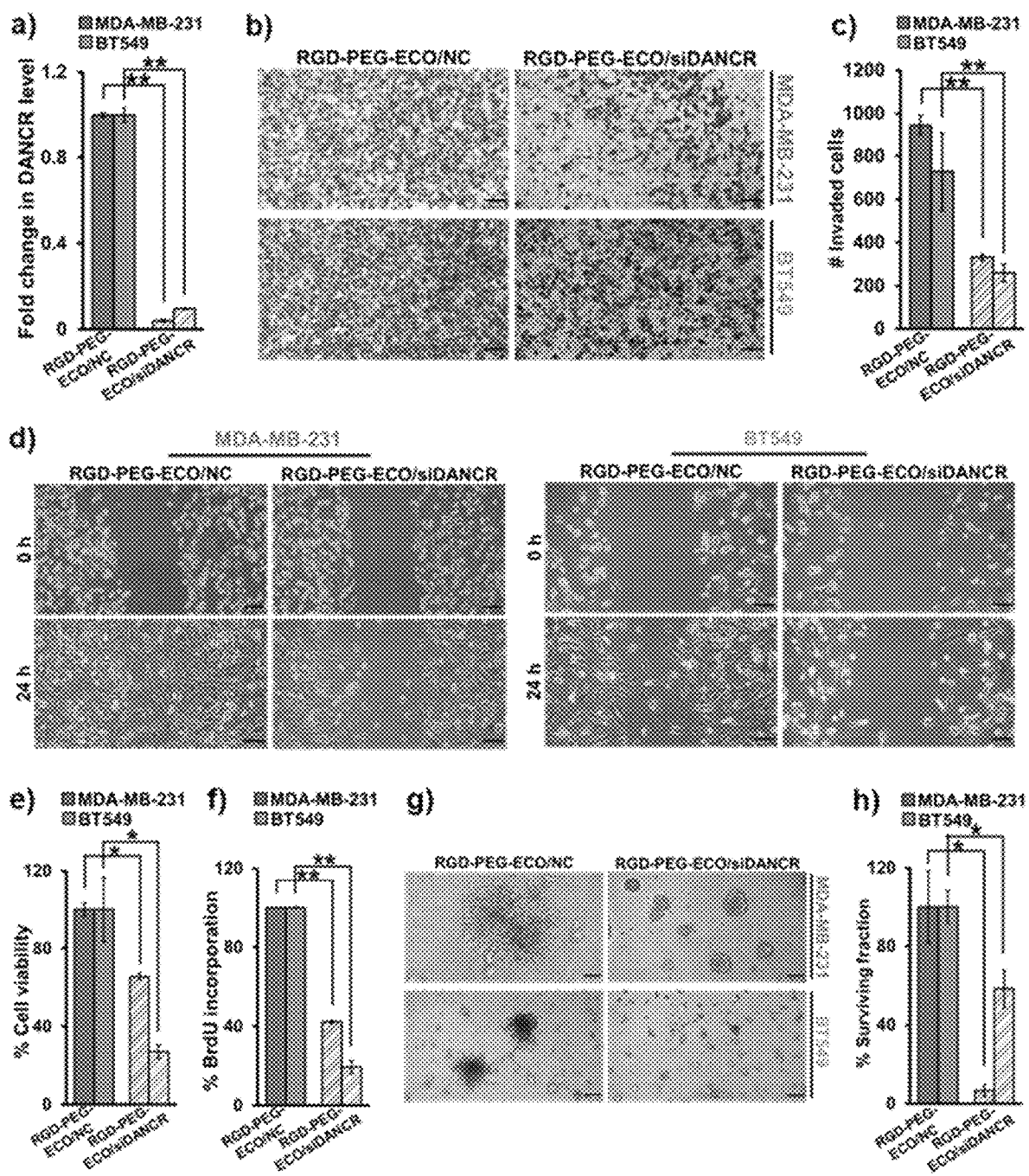
Figs. 17A-H

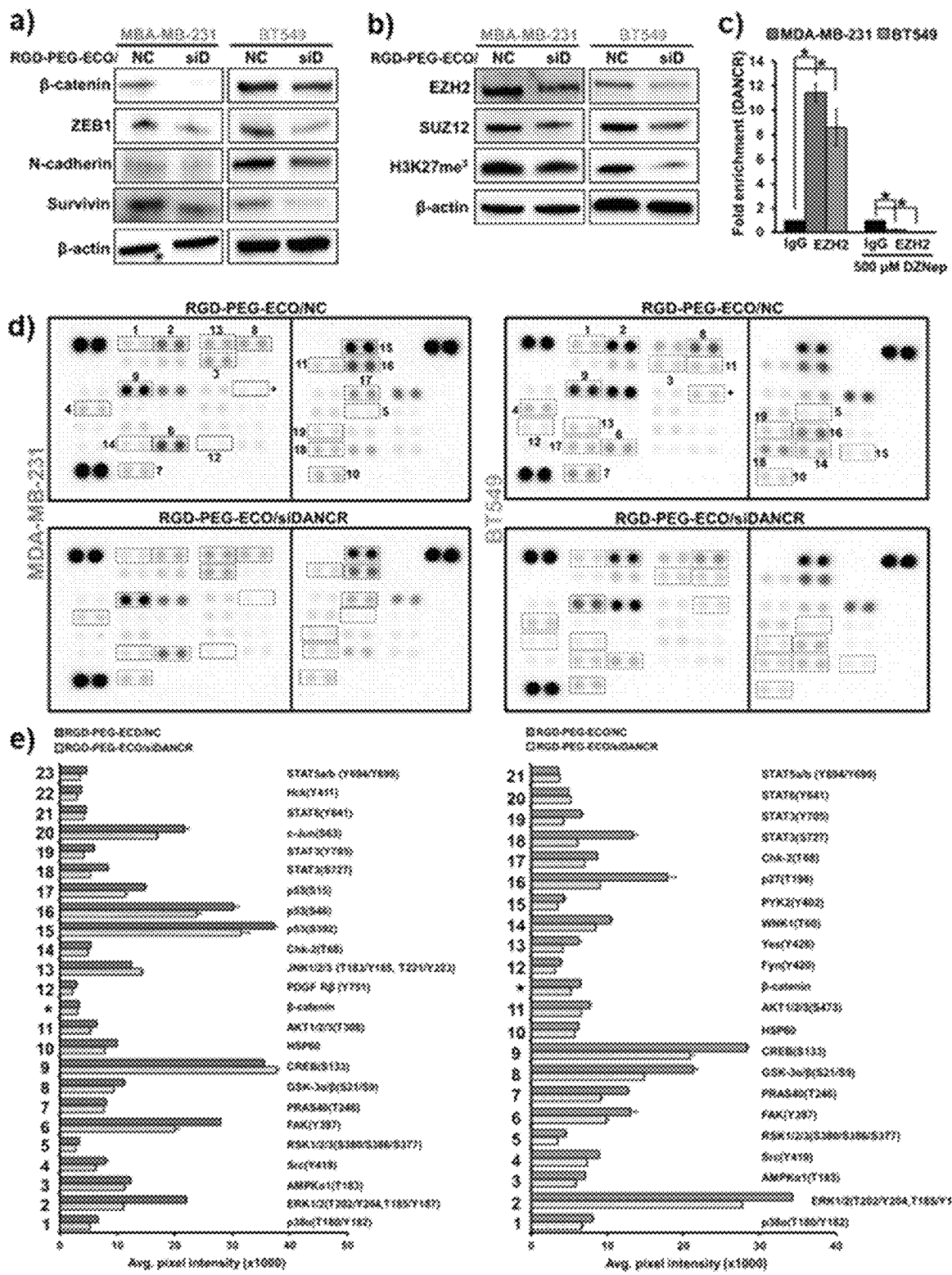
Figs. 18A-E

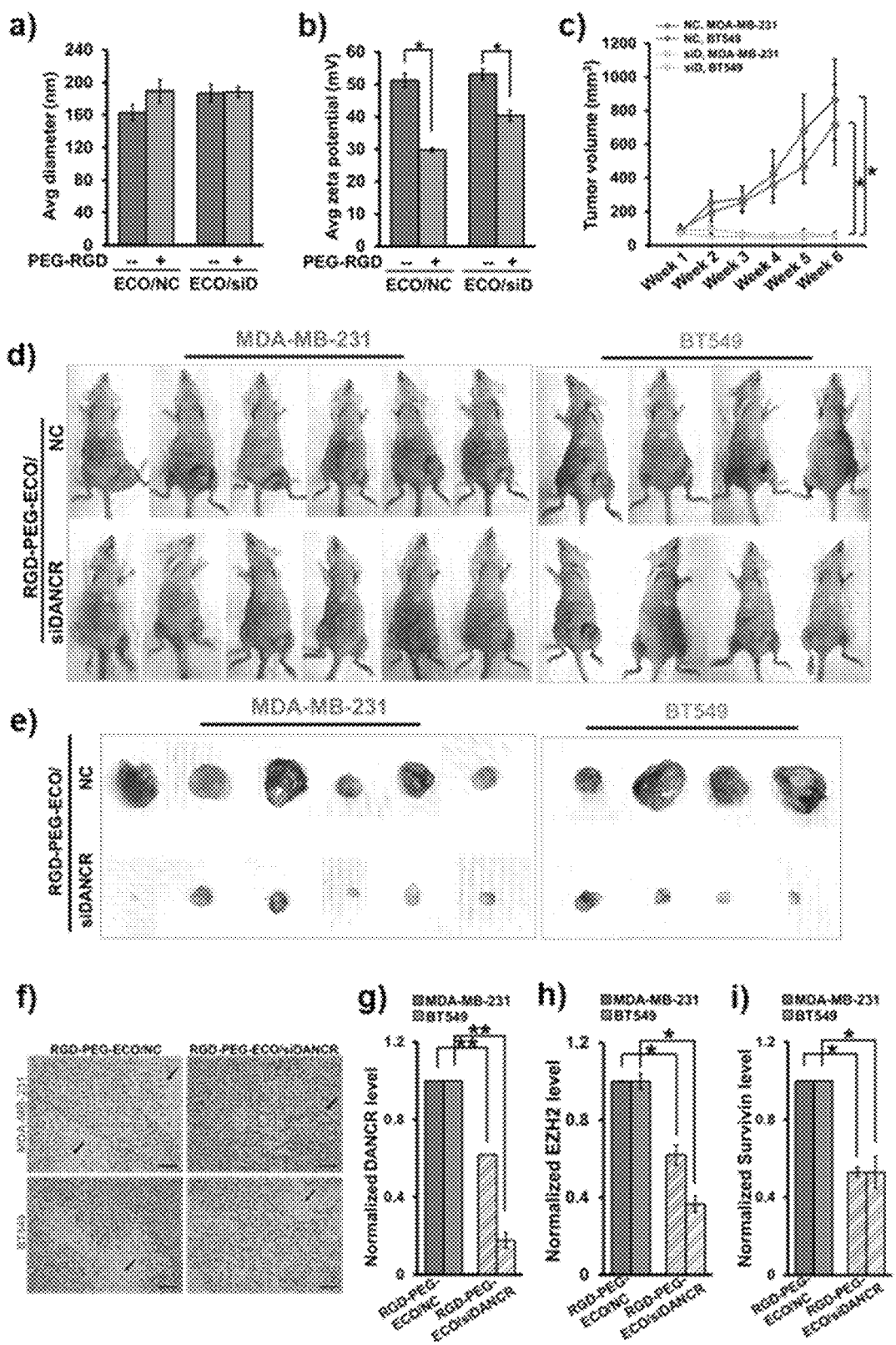
Figs. 19A-I

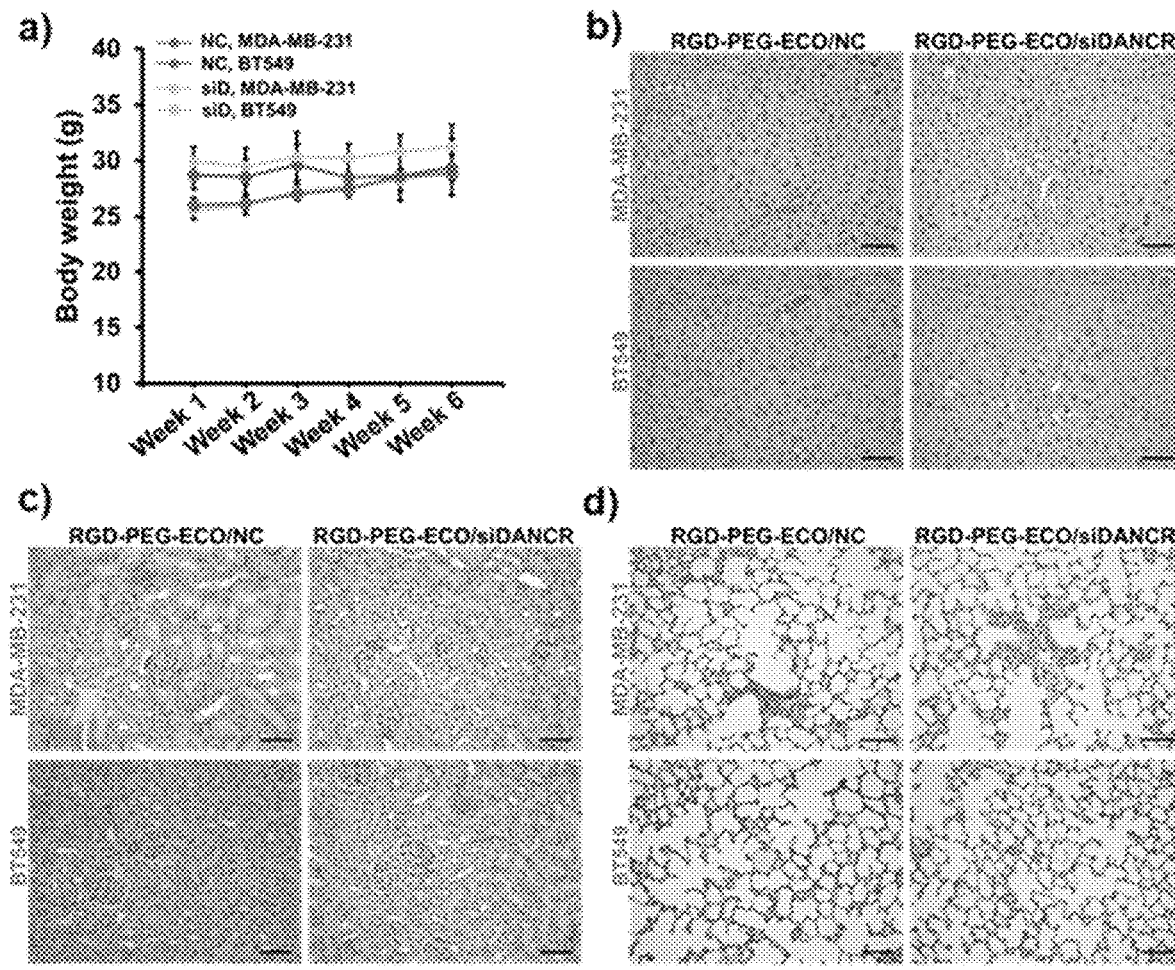
Figs. 20A-D

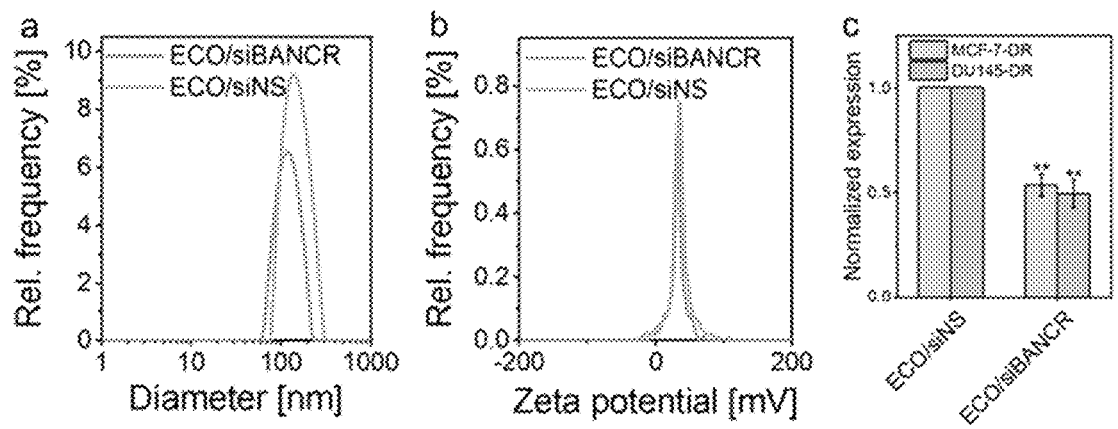
Figs. 24A-C
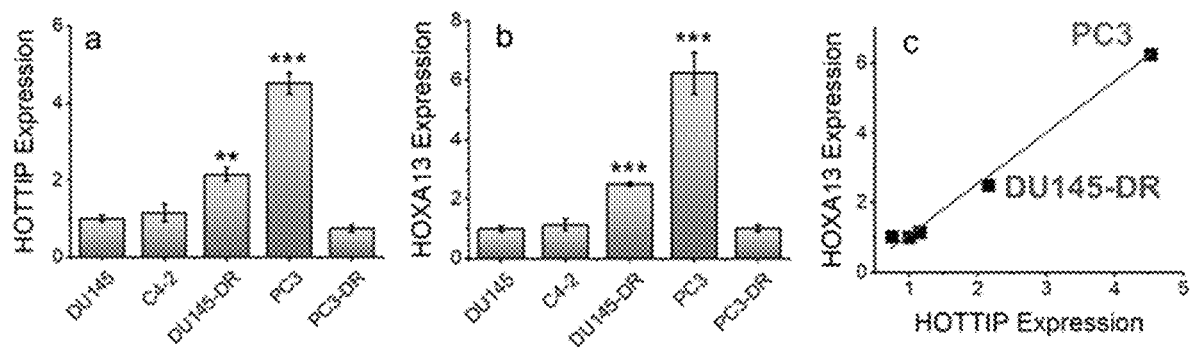
Fig. 25A-C

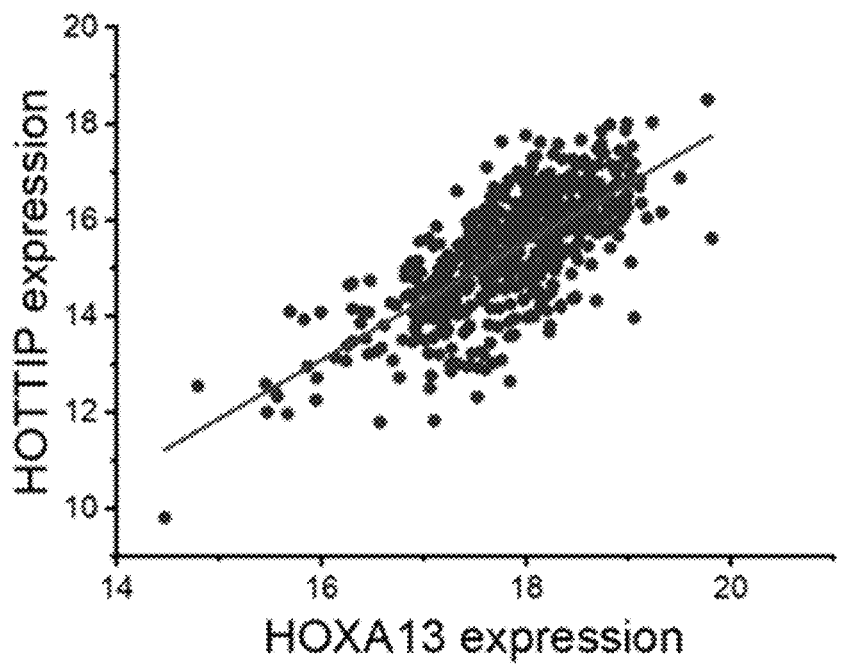
Fig. 26
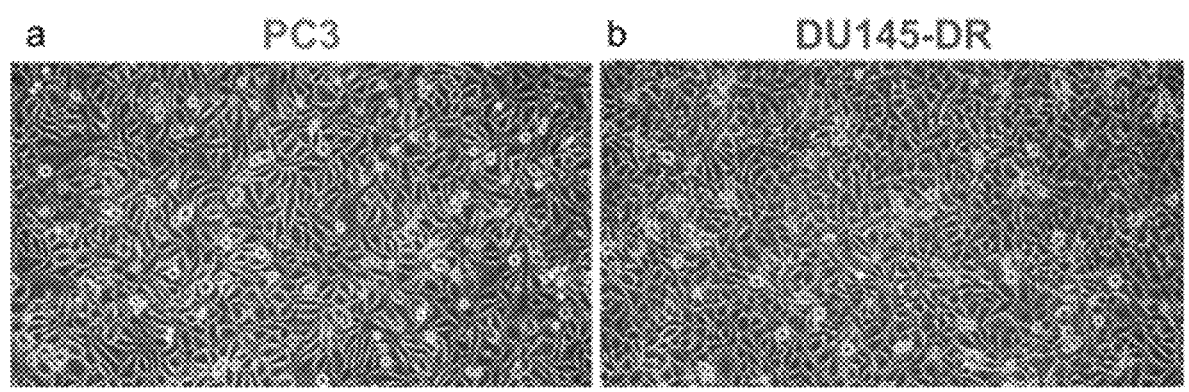
Fig. 27A-B

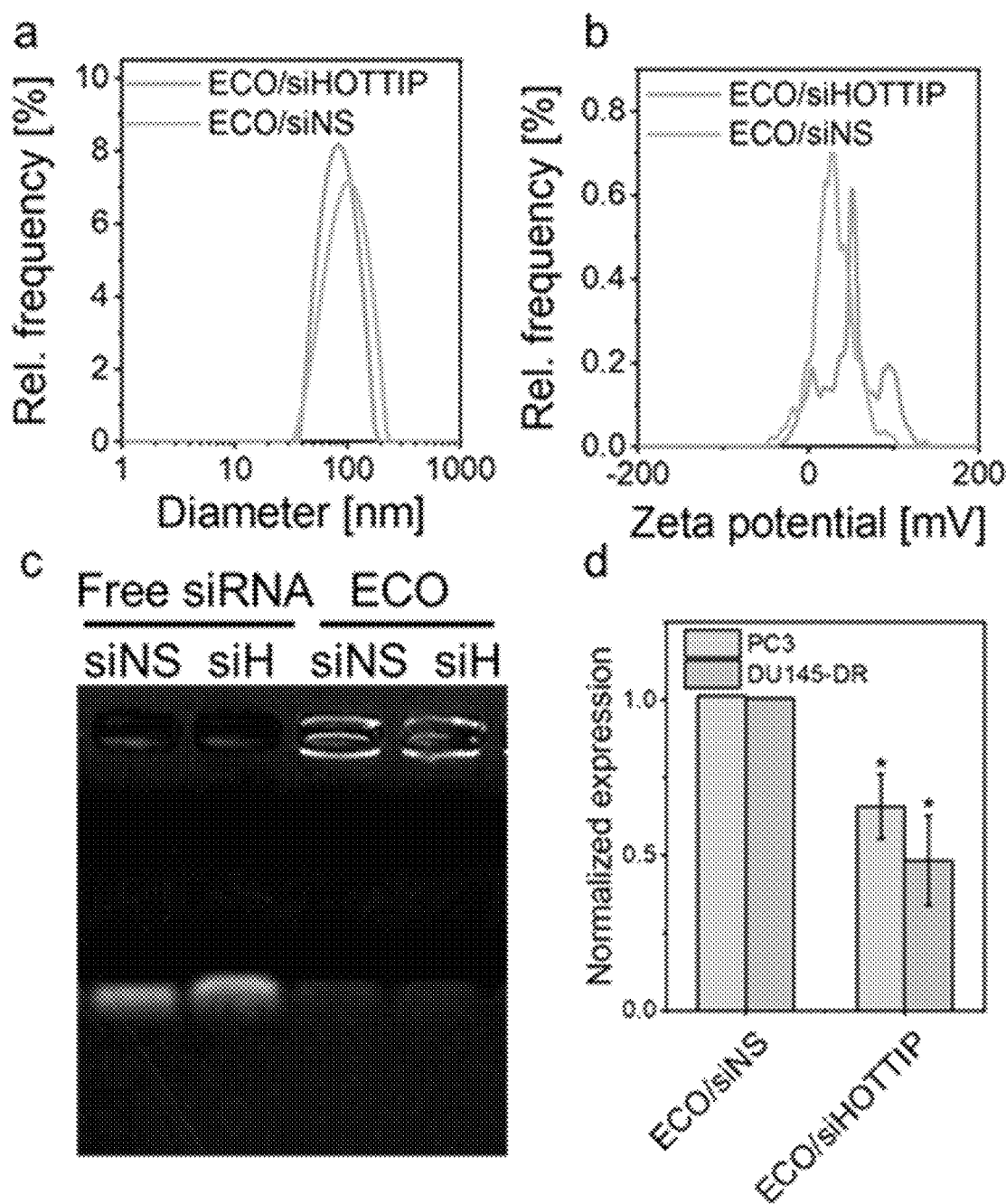
Figs. 28A-D

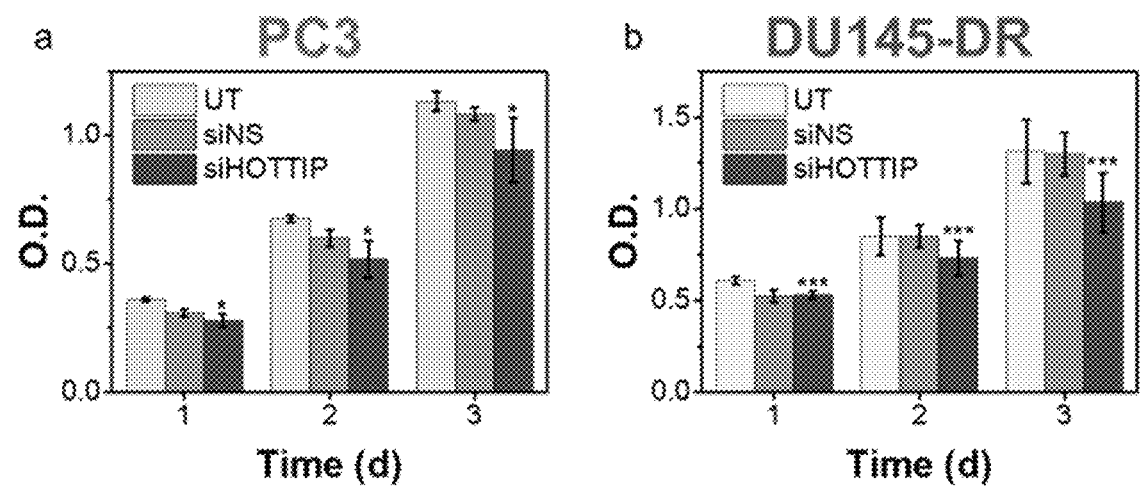
Figs. 29A-B
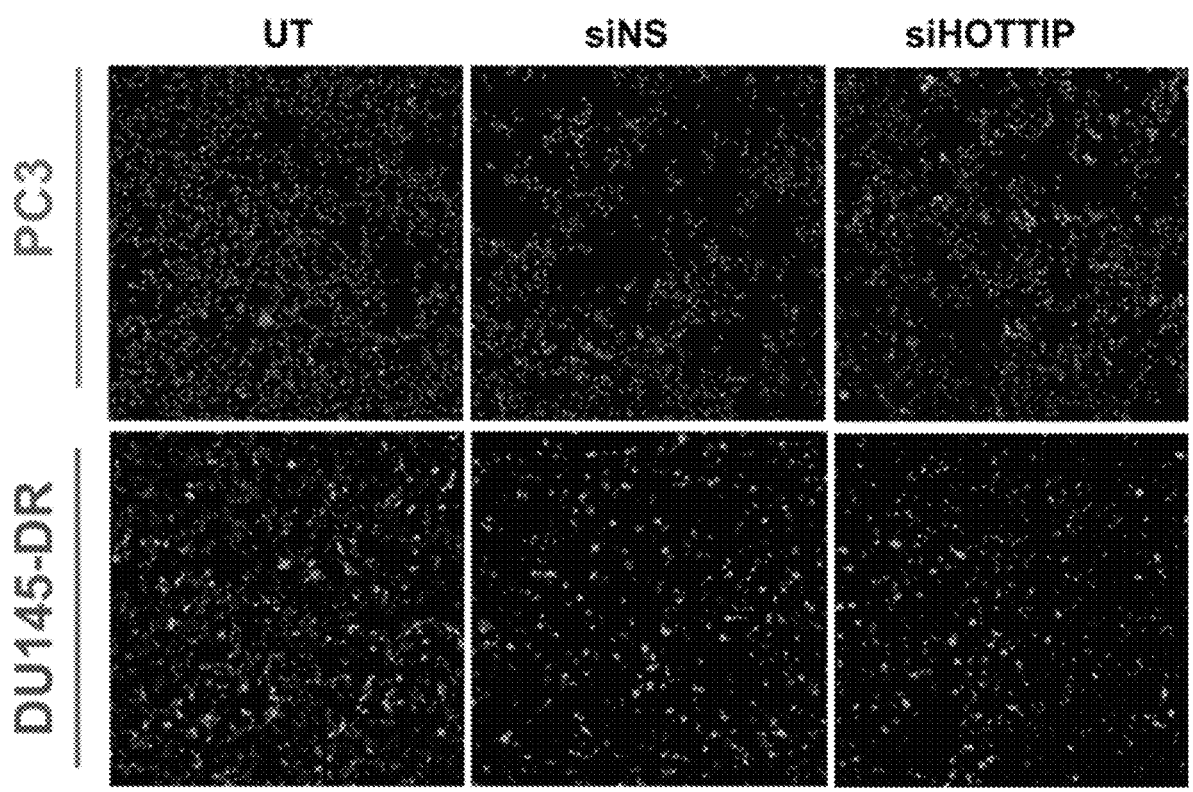
Fig. 30

SEQUENCE LISTING

```
<160> NUMBER OF SEQ ID NOS: 27

<210> SEQ ID NO 1
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1
gcucaucugg aagcuacuca ucact                                           25

<210> SEQ ID NO 2
<211> LENGTH: 27
<212> TYPE: DNA
<213> ORGANISM: Artificial Sequence
<220> FEATURE:
<223> OTHER INFORMATION: Synthetic Construct

<400> SEQUENCE: 2
agugaugagu agcuuccaga ugagcuc                                         27

<210> SEQ ID NO 3
<211> LENGTH: 25
<212> TYPE: DNA
<213> ORGANISM: Artificial Sequence
<220> FEATURE:
<223> OTHER INFORMATION: Synthetic Construct

<400> SEQUENCE: 3
gcucaucugg aaacuccuca ucacc                                           25

<210> SEQ ID NO 4
<211> LENGTH: 27
<212> TYPE: DNA
<213> ORGANISM: Artificial Sequence
<220> FEATURE:
<223> OTHER INFORMATION: Synthetic Construct

<400> SEQUENCE: 4
```
ggugaugagg aguuuccaga ugagcuc                               27

<210> SEQ ID NO 5
<211> LENGTH: 23
<212> TYPE: DNA
<213> ORGANISM: Artificial Sequence
<220> FEATURE:
<223> OTHER INFORMATION: Synthetic Construct

<400> SEQUENCE: 5
cuuacgcuga guacuucgad tdt                                   23

<210> SEQ ID NO 6
<211> LENGTH: 23
<212> TYPE: DNA
<213> ORGANISM: Artificial Sequence
<220> FEATURE:
<223> OTHER INFORMATION: Synthetic Construct

<400> SEQUENCE: 6
ucgaaguacu cagcguaagd tdt                                   23

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
aagcaaaccu gcggcugauc u                                     21

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct

<400> SEQUENCE: 8
ctactaagag cggctccacc ac                                    22

<210> SEQ ID NO 9
<211> LENGTH: 22
<212> TYPE: DNA
<213> ORGANISM: Artificial Sequence
<220> FEATURE:
<223> OTHER INFORMATION: Synthetic Construct

<400> SEQUENCE: 9
tcgattgctt gacgcagtct cc                                    22

<210> SEQ ID NO 10
<211> LENGTH: 22
<212> TYPE: DNA
<213> ORGANISM: Artificial Sequence
<220> FEATURE:
<223> OTHER INFORMATION: Synthetic Construct

<400> SEQUENCE: 10
acggatttgg tcgtattggg cg                                    22

<210> SEQ ID NO 11
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 11
ctcctggaag atggtgatgg                                                      20

<210> SEQ ID NO 12
<211> LENGTH: 27
<212> TYPE: DNA
<213> ORGANISM: Artificial Sequence
<220> FEATURE:
<223> OTHER INFORMATION: Synthetic Construct

<400> SEQUENCE: 12
ggucaugaga aacguggauu acadcdc                                              27

<210> SEQ ID NO 13
<211> LENGTH: 27
<212> TYPE: DNA
<213> ORGANISM: Artificial Sequence
<220> FEATURE:
<223> OTHER INFORMATION: Synthetic Construct

<400> SEQUENCE: 13
gguguaaucc acguuucuca ugaccuc                                              27

<210> SEQ ID NO 14
<211> LENGTH: 18
<212> TYPE: DNA
<213> ORGANISM: Artificial Sequence
<220> FEATURE:
<223> OTHER INFORMATION: Synthetic Construct

<400> SEQUENCE: 14
ccuacgccga guacuucg                                                        18

<210> SEQ ID NO 15
<211> LENGTH: 23
<212> TYPE: DNA
<213> ORGANISM: Artificial Sequence
<220> FEATURE:
<223> OTHER INFORMATION: Synthetic Construct

<400> SEQUENCE: 15
dtdtggaugc ggcucaugaa gcu                                                  23

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
gcgccactat gtagcgggtt                                                      20

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17
tcaatggctt gtgcctgtag tt                                                   22
```

```
<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
tcaagaacga aagtcggagg                                                  20

<210> SEQ ID NO 19
<211> LENGTH: 19
<212> TYPE: DNA
<213> ORGANISM: Artificial Sequence
<220> FEATURE:
<223> OTHER INFORMATION: Synthetic Construct

<400> SEQUENCE: 19
ggacatctaa gggcatcac                                                   19

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
aggacggctc ctctaaccat                                                  20

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
cttggtgttg cactgtgctt                                                  20

<210> SEQ ID NO 22
<211> LENGTH: 21
<212> TYPE: DNA
<213> ORGANISM: Artificial Sequence
<220> FEATURE:
<223> OTHER INFORMATION: Synthetic Construct

<400> SEQUENCE: 22
atggccgagg ctggcttcat c                                                21

<210> SEQ ID NO 23
<211> LENGTH: 22
<212> TYPE: DNA
<213> ORGANISM: Artificial Sequence
<220> FEATURE:
<223> OTHER INFORMATION: Synthetic Construct

<400> SEQUENCE: 23
acggcgcact ttcttcgcag tt                                               22

<210> SEQ ID NO 24
<211> LENGTH: 21
<212> TYPE: DNA
<213> ORGANISM: Artificial Sequence
<220> FEATURE:
<223> OTHER INFORMATION: Synthetic Construct
```

```
<400> SEQUENCE: 24
gcacaggacu ccauggcaau u                                      21

<210> SEQ ID NO 25
<211> LENGTH: 21
<212> TYPE: DNA
<213> ORGANISM: Artificial Sequence
<220> FEATURE:
<223> OTHER INFORMATION: Synthetic Construct

<400> SEQUENCE: 25
uugccaugga guccugugcu u                                      21

<210> SEQ ID NO 26
<211> LENGTH: 21
<212> TYPE: DNA
<213> ORGANISM: Artificial Sequence
<220> FEATURE:
<223> OTHER INFORMATION: Synthetic Construct

<400> SEQUENCE: 26
cggcaggagc ccaaggaaau u                                      21

<210> SEQ ID NO 27
<211> LENGTH: 21
<212> TYPE: DNA
<213> ORGANISM: Artificial Sequence
<220> FEATURE:
<223> OTHER INFORMATION: Synthetic Construct

<400> SEQUENCE: 27
uuuccuuggg cuccugccgu u                                      21
```

COMPOSITIONS AND METHODS FOR THE DELIVERY OF NUCLEIC ACIDS

RELATED APPLICATION

This application claims priority from U.S. Provisional Application Nos. 62/738,677, filed Sep. 28, 2018, and is a Continuation-in-Part of U.S. Ser. No. 14/743,298, filed Jun. 18, 2015, the subject matter of which are incorporated herein by reference in their entirety.

GOVERNMENT FUNDING

This invention was made with government support under Grant No. EB00489 awarded by The National Institutes of Health and Grant Number DGE-0951783, awarded by the National Science Foundation Graduate Research Fellowship. The United States government has certain rights to the invention.

BACKGROUND

RNA interference (RNAi) is a natural antisense mechanism that cells possess to regulate the expression of genes at the mRNA level. This process relies on the ability of short fragments (19-23 nucleotides in length) of double stranded small interfering RNA (siRNA) to recognize and guide complementary mRNA transcripts into the RNA-induced silencing complex (RISC). Once translocated into the RISC complexes, the mRNA transcripts are cleaved and ultimately degraded inside the cell, rendering them ineffective for translation into proteins. Meanwhile, the siRNAs are preserved and constantly recycled for further silencing events. The ability to synthetically design siRNAs against particular mRNA sequences has triggered numerous clinical and pre-clinical studies to tailor RNAi induced silencing against a variety of disease-related genetic transcripts.

Delivery of siRNA with nanoparticles is desirable in order to overcome their susceptibility to serum nucleases and their ability to stimulate the innate immune system upon intravenous injection. The use of nanoparticles can also prevent the possibility of off-target side effects. Nanoparticles are also required for successful siRNA therapies because they can facilitate intracellular release following uptake by tumor cells. Endocytosis has been identified as a dominant cellular uptake mechanism, whereby foreign material delivered to cells will be sequestered into endosomal compartments and ultimately degraded after fusion with lysosomes. As a result, siRNA therapy faces an additional delivery barrier because access to the RISC complexes in the cytoplasm is necessary for effective treatment. Viral vectors have evolved for millions of years to become efficient carriers at introducing their genetic material into host cells. As a result, adenoviruses and retroviruses are currently explored as possible gene therapy vectors, but the success they have shown in vivo is masked by their potential to severely trigger the immune response.

Compared to viral vectors, non-viral or synthetic vectors have many advantages, such as low immunogenicity, low production cost, and ease of modification, thus making them very attractive for siRNA delivery platforms. However, much research is still required in order to improve upon the low transfection efficiencies of most current non-viral vectors.

Cationic lipid constructs are widely used as alternatives to viral nanoparticles. They form nanoparticles through the electrostatic interaction with the negatively-charged siRNA. Such nanoparticles, or lipoplexes, can be designed to exhibit similar characteristics and behaviors to those observed with viral vectors by utilizing pH sensitive moieties that facilitate endosomal escape. This is typically accomplished by incorporating an amine-rich head group with an overall slightly acidic pKa into the cationic lipid structure. Once they become protonated in the acidic endosomal-lysosomal compartments, cationic lipoplexes are able to participate in membrane fusion and degradation events by inducing an electrostatic flip-flop reorganization of anionic phospholipids in the membrane bilayer. This extensive transfer of lipids neutralizes the charge interactions that govern particle formation, causing the inevitable dissociation of siRNA from the lipoplexes, followed by and subsequent release into the cytoplasm.

SUMMARY

Embodiments described herein relate to compounds used to form multifunctional pH-sensitive carriers that are designed to condense nucleic acids and deliver the condensed nucleic acids to cells. The compounds can include a protonable amino head group, which can complex with nucleic acids, fatty acid or lipid tails, which can participate in hydrophobic condensation, and two cystenyl residues capable of forming disulfide bridges via autooxidation.

In some embodiments, the compound includes formula (I):

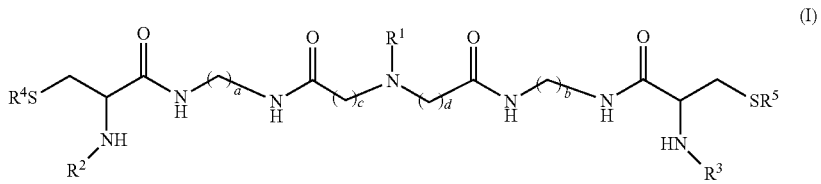

wherein $R^1$ is an akylamino group or a group containing at least one aromatic group; $R^2$ and $R^3$ are independently an aliphatic group or a hydrophobic group derived, for example, from a fatty acid; $R^4$ and $R^5$ are independently H, a substituted or unsubstituted akyl group, an akenyl group, an acyl group, an aromatic group, polymer, a targeting group, or a detectable moiety; a, b, c, and d are independently an integer from 1 to 10 (e.g., a, b, c, and d are each 2); and pharmaceutically acceptable salts thereof.

In some embodiments, $R^1$ can include at least one of:

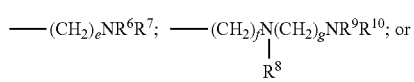

-continued

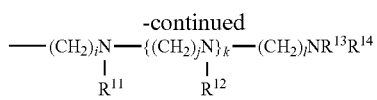

where $R^6$, $R^7$, $R^8$, $R^9$, $R^{10}$, $R^{11}$, $R^{12}$, $R^{13}$, and $R^{14}$ are independently hydrogen, an alkyl group, a hydrophobic group, or a nitrogen containing substituent; and e, f, g, i, j, k, and l, are an integer from 1 to 10. For example, $R^1$ can include at least one of $CH_2CH_2NH_2$, $CH_2CH_2NHCH_2CH_2NHCH_2CH_2NH$, or $CH_2CH_2NHCH_2CH_2CH_2CH_2NHCH_2CH_2CH_2NH$.

In other embodiments, $R^2$ and $R^3$ are independently a hydrophobic group derived from oleic acid or linoleic acid and are the same or different.

In some embodiments, $R^4$ and $R^5$ are independently H, a substituted or unsubstituted polymer, a targeting group, or a detectable moiety.

In some embodiments, the compound can have the formulas:

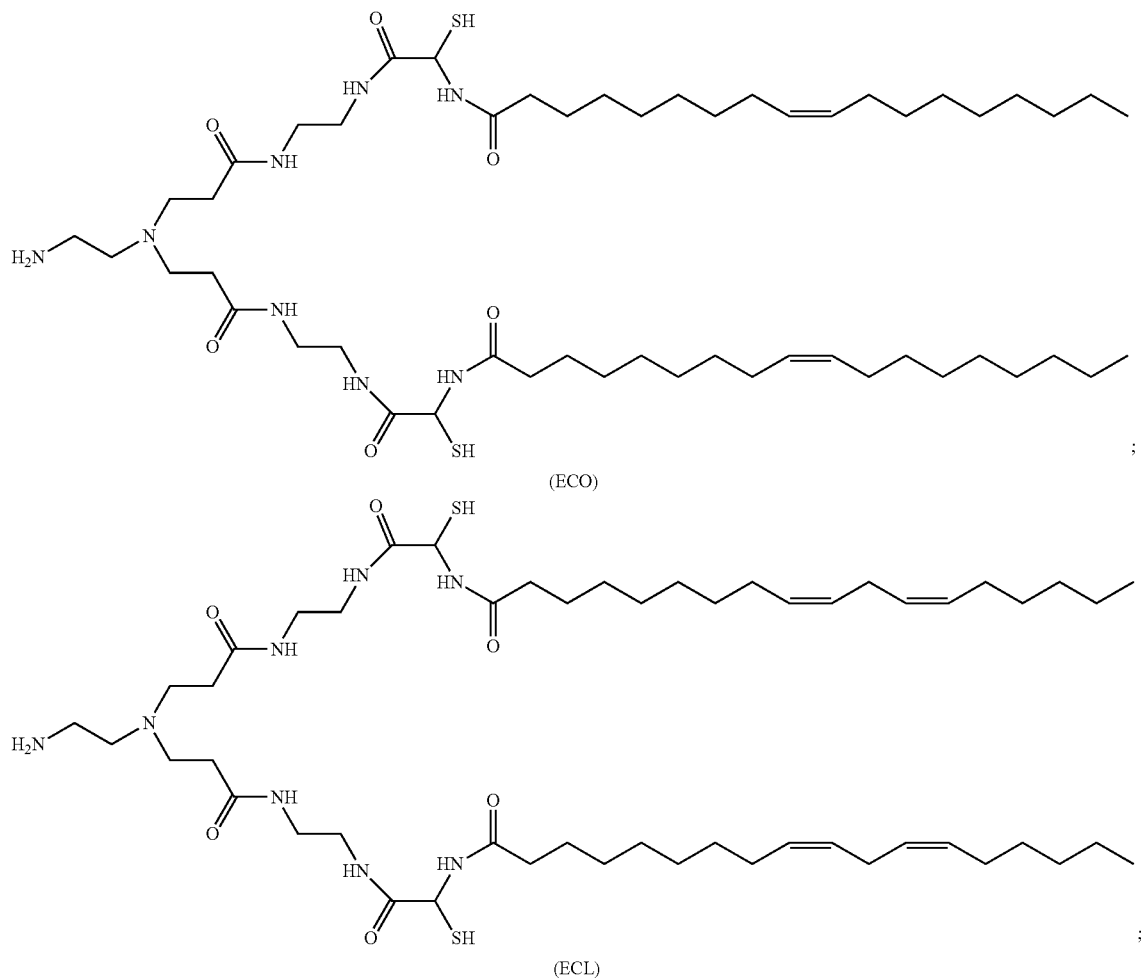

or pharmaceutically acceptable salts thereof.

In other embodiments, a targeting group can be covalently attached to the compound by a linker. The targeting group can be a peptide, a protein, an antibody, or an antibody fragment. The linker can include a polyamino acid group, a polyalkylene group, or a polyethyelene glycol group. The linker can also include an acid labide bond that is hydrolyzable in an endolyssomal environment following uptake to cells, such as cancer cells.

BRIEF DESCRIPTION OF THE DRAWINGS

FIGS. 2(A-D) illustrate a schematic, plots, and immunoblots showing ECO/siβ3 nanoparticles induced sustained gene silencing of β3 integrin. A) ECO forms nanoparticles with siRNA through electrostatic interactions, disulfide cross-linking and hydrophobic interactions. B) β3 integrin mRNA expression in quiescent or TGF-β stimulated (5 ng/mL, 72 hours) NME and MDA-MB-231 cells with the indicated treatment groups at 100 nM siRNA by semi-quantitative real-time PCR (n=3, mean±SE, p≤0.01 for all time points beyond 8 hours). Western blot analysis of β3 integrin expression in quiescent or TGF-β stimulated (5 ng/mL, 72 hours) NME c) and MDA-MB-231 d) cells at the indicated time points post-nanoparticle treatment with the indicated treatment groups.

B) Semi-quantitative real-time PCR analysis (n=3) of EMT markers in NME cells (**p≤0.01). C) Western blot analysis of E-cadherin and N-cadherin in NME cells. D) Invasion assay of quiescent or TGF-β stimulated NME cells (n=3, *p≤0.05, **p≤0.01). E) Proliferation as measured by [$^3$H] thymidine incorporation of either quiescent or TGF-β stimulated NME cells (n=3, *p≤0.05, **p≤0.01). For all experimental groups, NME cells were pre-treated with TGF-β (5 ng/mL; 72 hours) followed by ECO/siRNA nanoparticle treatment using 100 nM siRNA. For panels b-e, data represent mean±SE. Results for panels c-e are representative of three independent experiments.

Figure 4A:
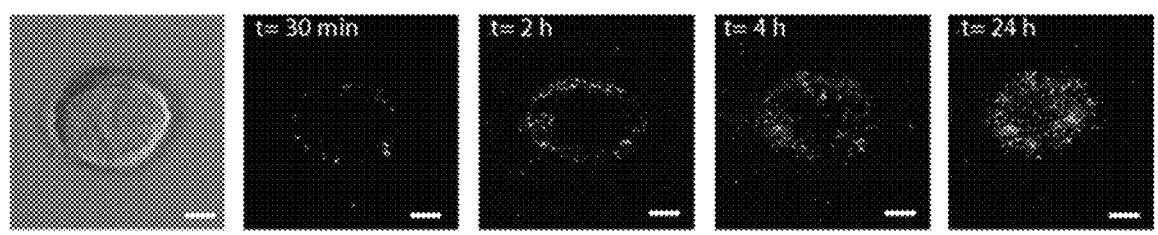
Figure 4B:
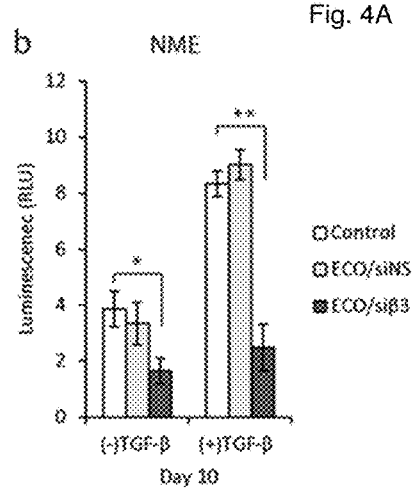
Figure 4C:
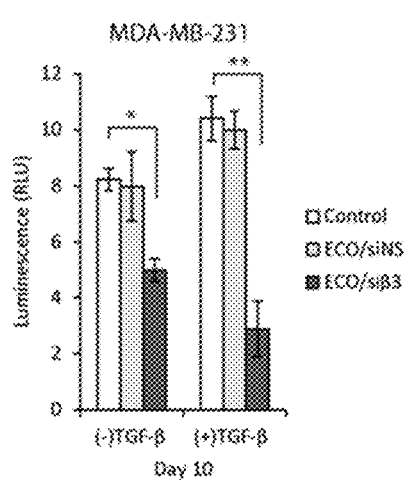

FIGS. 4(A-C) illustrate images and graphs showing ECO/siβ3 nanoparticles attenuated 3D organoid outgrowth. NME and MDA-MB-231 cells were grown in a compliant 3D-organotypic microenvironment and treated with ECO nanoparticles containing Alexa Fluor 488-labeled siRNA. Cellular uptake of ECO/siRNA nanoparticles monitored by fluorescence confocal microscopy (scale bar, 100 m). A) Brightfield microscopic image of a single organoid and fluorescence confocal microscopic images of ECO/siRNA nanoparticle uptake in the organoid over the course of 24 hours. B) NME and c) MDA-MB-231 cells were grown in a compliant 3D-organotypic microenvironment for up to 10 days with or without prior TGF-β stimulation (5 ng/mL) for 72 h. On day 4, 6 and 8, cells were treated with ECO/siNS or ECO/siβ3 nanoparticles at 100 nM siRNA. Organoid growth at day 10 was monitored via longitudinal bioluminescence (n=4, *p≤0.05, **p≤0.01). For panels c-d, data represent mean±SE.

Figures 5A, 5B, 5C, 5D, 5E:
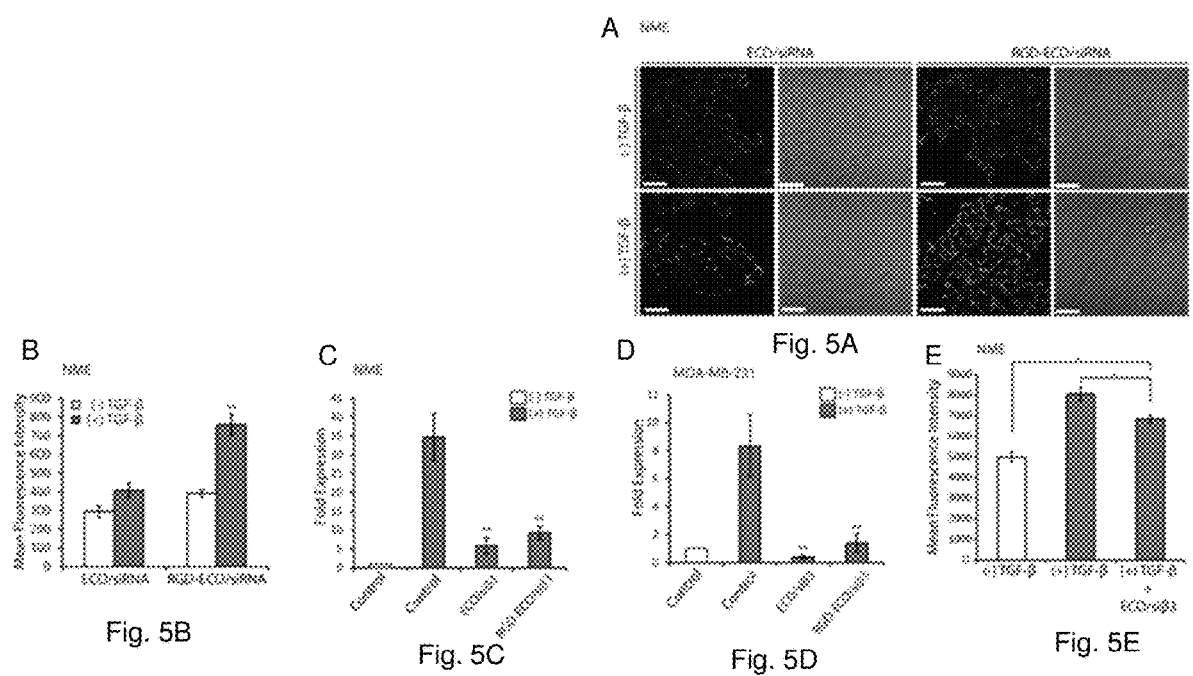

FIGS. 5(A-E) illustrate images and a graph showing RGD modification of ECO/siRNA nanoparticles enhances uptake in post-EMT breast cancer cells. A) confocal microscopy (scale bar, 50 μm) and B) quantified by flow cytometry (n=3, p≤0.01). Quantitative analysis of β3 integrin mRNA levels following treatment with siβ3 nanoparticles by real-time PCR (n=3, p≤0.01) in (C) NME and (D) MDA-MB-231 cells revealed RGD-targeted ECO/siRNA nanoparticles maintain gene silencing. E) Cellular uptake in NME cells, both with and without TGF-β stimulation (5 ng/mL; 72 hours), was quantified by flow cytometry for RGD-ECO/siRNA nanoparticles containing Alexa Fluor 488-labelled siRNA 4 hours after treatment. One group of TGF-β stimulated NME cells (TGF-β+ECO/siβ3) was treated with ECO/siβ3 nanoparticles at 100 nM siRNA for 48 hours prior to cellular uptake with the RGD-targeted nanoparticles to quantify the effect of β3 integrin silencing on targeted uptake (n=3, ±SE, *p≤0.05, **p≤0.01). For panels B-E, data represent mean±SE.

FIGS. 6(A-F) illustrate RGD-targeted ECO/siβ3 nanoparticles inhibited primary tumor growth and EMT in mice after systemic administration. A) and quantified by B) BLI (data represents mean±SE, n=5, *p≤0.05, **p≤0.01), and C) caliper measurements (data represents mean±SE, n=5, *p≤0.05, p≤0.01). D) Primary tumors were resected at week 9, and final tumor weights of the indicated treatment groups were obtained (data represents mean±SE, n=5, p≤0.01). E) Semi-quantitative real-time quantification of β3 integrin mRNA expression from resected primary tumors of the indicated groups (data represents mean±SE, n=5, **p≤0.01). F) H&E, DAPI and fibronectin immunostaining of the indicated primary tumors (scale bar, 300 m).

FIGS. 7(A-E) illustrate RGD-ECO/siβ3 nanoparticles inhibited breast cancer metastasis and primary tumor recurrence. A) BLI images of mice at week 12 revealed differences in metastasis and primary tumor recurrence for the different treatment groups after primary tumor resection on week 9. B) Quantification of primary tumor recurrence (data represents mean±SE, n=5, *p≤0.05). C) Quantification of thoracic metastasis by BLI (data represents mean±SE, n=5, *p≤0.05, **p≤0.01). Mice were released from ECO/siRNA therapeutic regimen at week 12. D) Representative BLI of mice on week 16. E) Quantification of whole body tumors from D. (data represents mean±SE, n=5, *p≤0.05).

FIGS. 8(A-C) illustrate plots showing zeta potential of A) ECO/siRNA, B) PEG-ECO/siRNA, and C) PEG(HZ)-ECO/siRNA nanoparticles incubated in PBS solutions at pH levels corresponding to stages of intracellular trafficking (pHs 7.4, 6.5, 5.4).

Figure 9:
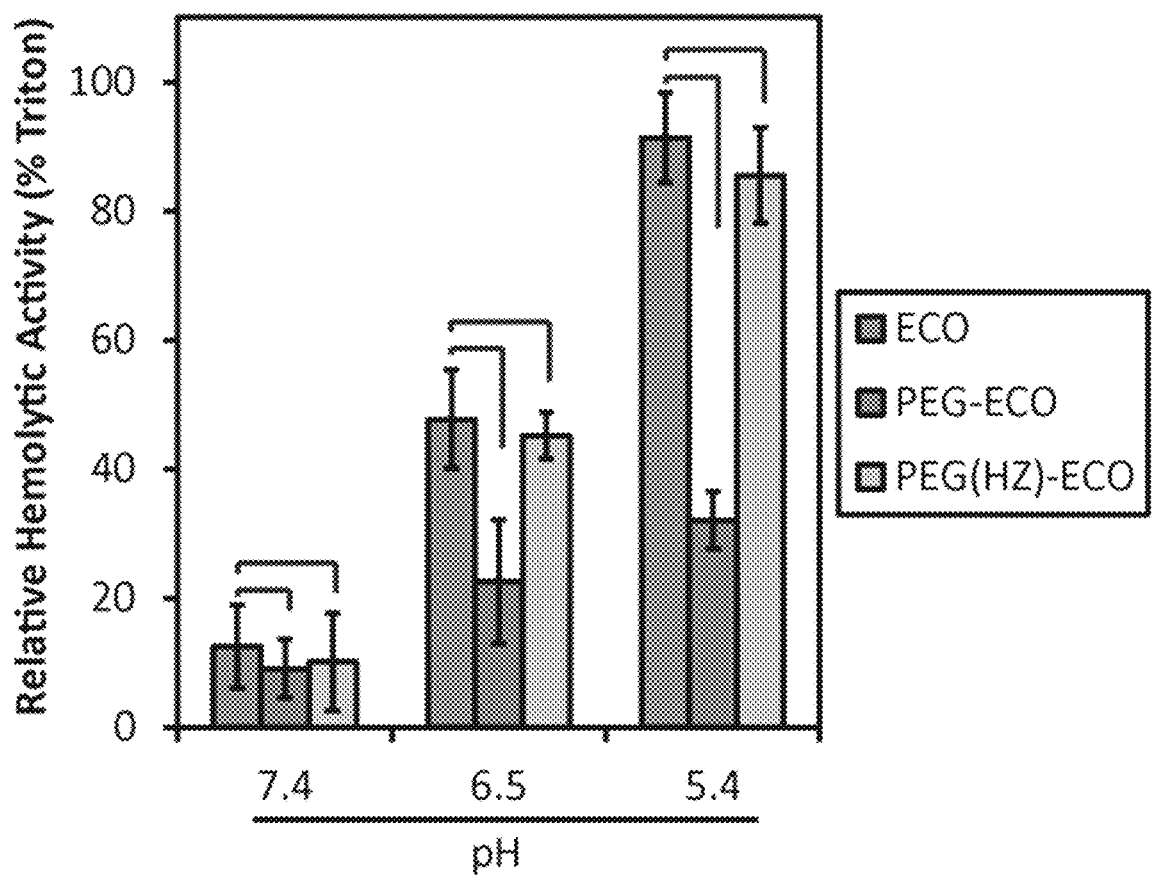

FIG. 9 illustrates a plot showing the comparison of hemolytic activity of ECO, PEG-ECO, and PEG(HZ)-ECO siRNA nanoparticles at pH levels corresponding to stages of intracellular trafficking. Relative hemolytic activity was calculated with respect to the hemolytic activity of 1% Triton-X-100.

FIGS. 10(A-C) illustrate a graph, plot, and image showing A) Cellular uptake of unmodified, PEG-, PEG(HZ)-, RGD-PEG-, and RGD-PEG(HZ)-modified ECO/siRNA nanoparticles quantified with flow cytometry using an AF647-labeled siRNA. B) Luciferase silencing of unmodified, PEG-, PEG(HZ)-, RGD-PEG-, and RGD-PEG(HZ)-modified ECO/siRNA nanoparticles in MDA-MB-231-luc triple-negative breast cancer cells. C) Confocal microscopy images of MDA-MB-231 cells incubated with RGD-PEG-, and RGD-PEG(HZ)-modified ECO/siRNA nanoparticles at 10 min, 3 hr, and 6 hr. DAPI, cell nucleus (blue); Lysotracker DND-26, lysosomes (green); siRNA, AF-647 (red).

FIGS. 11(A-D) illustrate in vivo luciferase silencing efficiency following a single i.v. treatment with various surface-modified ECO/siRNA nanoparticles (1.0 mg/kg siRNA dose). A) Quantification of bioluminescence signal from ROIs drawn over the tumor. B) Representative BLI images of the different treatment groups. Tumor accumulation and retention of surface-modified ECO/siRNA nanoparticles following i.v. administration. C) Representative FMT images of a single mouse from each treatment group over 24 hours post-treatment with nanoparticles formulated with an AF647-tagged siRNA. An ROI was drawn over the area containing the tumor. D) Quantification of fluorescence signal from each ROI. Flow cytometry and confocal microscopy analysis of single cell suspensions obtained from primary MDA-MB-231 mammary fat pad tumors following i.v. administration of various surface modified ECO/siRNA nanoparticles.

Figure 12A:
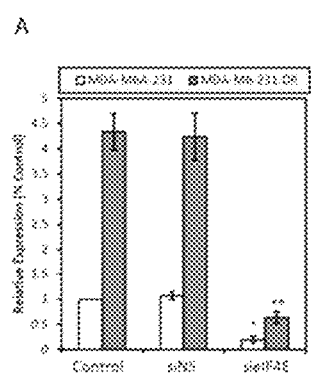
Figure 12B:
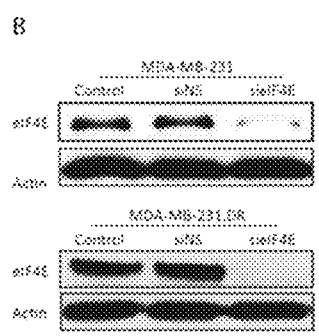

FIGS. 12(A-C) illustrate evaluation of eIF4E mRNA and protein expression as determined by A) qRT-PCR and B) western blot analysis in MDA-MB-231 and MDA-MB-231.DR cells 5 days following treatment with RGD-PEG(HZ)-ECO/siRNA nanoparticles (N/P=8) delivering either sieIF4E or siNS (100 nM). C) Dose-response curves as determined by MTT assay of MDA-MB-231 and MDA-MB-231.DR cells treated with varying concentrations of PTX following prior treatment with RGD-PEG(HZ)-ECO/siRNA nanoparticles delivering sieIF4E or siNS. Cells were first treated with RGD-PEG(HZ)-ECO/siRNA nanoparticles for 48 hours followed by treatment with varying concentrations of PTX for an additional 48 hours.

FIGS. 13(A-F) illustrate in vivo efficacy of combination therapy involving PTX and RGD-PEG(HZ)-ECO/sieIF4E nanoparticles. Alternating treatment of siRNA nanoparticles and PTX every 6 days began after 4 weeks once the primary tumors reach an average of 150 mm$^3$. A) Quantification of bioluminescent imaging over the course of the experiment (data represents mean±SE, n=5, *p≤0.05, **p≤0.01) and B)

BLI images at week 10. C) Tumor growth was monitored using digital caliper measurements (data represents mean±SE, n=5, *p≤0.05, **p≤0.01). D) Primary tumors were resected at week 10 and E) final tumor weights were obtained (data represents mean±SE, n=5, *p≤0.05, **p≤0.01). F) Semi-quantitative real-time quantification of eIF4E mRNA expression from the resected primary tumors (data represents mean±SE, n=5, *p≤0.05, **p≤0.0, # p>0.05).

FIGS. 14(A-B) illustrate a schematic representation of formation and working of RGD-PEG-ECO/siRNA nanoparticles. (a) Amino lipid carrier ECO (E) is mixed with the targeting moiety RGD-PEG-Mal followed by electrostatic condensation with siRNA molecules. Oxidation of cysteine residues (C) to form disulfide bonds and hydrophobic condensation of the oleic acid tails (O) further stabilize the formation of RGD-PEG-ECO/siRNA nanoparticles. (b) RGD-PEG-ECO/siRNA nanoparticles mediate efficient siRNA delivery by the PERC mechanism. Nanoparticles are internalized into cells by receptor-mediated endocytosis and travel through the intracellular trafficking pathway. As the pH in the endosomes decreases, the pH-sensitive amphiphilicity of the nanoparticles enables them to induce endosomal membrane destabilization and endosomal escape into the cytosol. The nanoparticles then undergo reductive dissociation, releasing the siRNA cargo into the cytoplasm where it encounters the RNAi machinery to silence the target lncRNA.

FIGS. 15(A-H) illustrate plots and an immunoblot showing DANCR is significantly overexpressed in TNBC. (a) Endogenous expression of DANCR is significantly elevated in all breast cancer cell lines: MCF7 (luminal A; $ER^+$, $PR^{+/-}$, $Her2^-$), ZR-75 (luminal B, $ER^+$, $PR^{+/-}$, $Her2^+$), and Hs578T, BT549, and MDA-MB-231 (claudin-low $ER^-$, $PR^-$, $Her2^-$), compared to HMECs, and even more so in the TNBC cell lines. (b) Quantification of DANCR expression from a breast cancer array containing cDNA from normal subjects (n=4) and breast cancer patients shows that DANCR is highly upregulated in tumor samples from TNBC patients (n=12), in comparison with breast tissues from normal subjects. (c) Differential gene expression analysis for DANCR performed for 104 normal and 790 breast cancer samples from TCGA database shows a significant upregulation of DANCR in breast cancer samples, particularly in 80 TNBC samples (d), compared to normal levels. (e) Heat map comparing and demonstrating the heterogeneity of DANCR expression in the individual normal (N) and TNBC (T) samples from TCGA database. DANCR expression is significantly higher in TNBC samples than breast cancer samples expressing (f) ER (n=584), (g) PR (n=508), and (h) HER2 (n=128) receptors (error bars denote s.e.m., *p≤0.05, ***p≤0.0005).

FIGS. 16(A-F) illustrate plots and images showing RGD-PEG-ECO/siDANCR nanoparticles mediate robust and sustained silencing of DANCR expression in MDA-MB-231 and BT549 cells. RGD-PEG-ECO/NC and RGD-PEG-ECO/siDANCR nanoparticles were formulated at N/P=10, RGD-PEG/ECO=2.5 mol %, and [siRNA]=100 nM and characterized on LiteSizer. The particles show (a) and (b) single intensity peaks indicating uniform distribution, with (c) predicted size of about 108 nm and zeta potential of 22 mV. (d) Gel retardation assay of RGD-PEG-ECO/NC and RGD-PEG-ECO/siDANCR nanoparticles shows high encapsulation efficiency, with free siRNA as control. (e) Morphology of RGD-PEG-ECO/NC and RGD-PEG-ECO/siDANCR nanoparticles is visualized by transmission electron microscopy. (f) MDA-MB-231 and BT549 cells transfected with RGD-PEG-ECO/NC and RGD-PEG-ECO/siDANCR nanoparticles were harvested on days 1, 4, and 7, for measurement of DANCR knockdown by qRT-PCR. DANCR expression by siDANCR treatment is normalized to NC treatment for both the cell lines (scale bar=200 nm, error bars denote s.e.m., **p≤0.00005, *p≤0.005).

FIGS. 17(A-H) illustrate graphs and images showing RGD-PEG-ECO/siDANCR nanoparticles inhibit TNBC invasion, migration, and proliferation. (a) siDANCR-treated MDA-MB-231 and BT549 cells show 80-90% knockdown in DANCR expression after 24 h, compared to NC-treated cells (p<0.0005). (b) DANCR silencing leads to substantial reduction in the invasive potential of MDA-MB-231 and BT549 cells plated in Matrigel-coated Transwell inserts in serum-free media for 24 h. The migrated cells were fixed with 10% formalin, stained with 0.05% crystal violet, and counted using ImageJ software (p<0.0005). (c & d) Standard scratch-wound assays demonstrate that siDANCR-treated MDA-MB-231 and BT549 cells have reduced ability to close the scratched wounds in 24 h, while the NC-treated cells readily migrate and close the wounds. (e) MTT assay demonstrates significant reduction in cell viability of MDA-MB-231 and BT549 cells treated with siDANCR nanoparticles, compared to NC (*p<0.01). (f) DANCR silencing in MDA-MB-231 and BT549 cells results in significant decrease in cell proliferation, as indicated by the decreased BrdU incorporation, in comparison to NC (**p<0.0001). (g) MDA-MB-231 and BT549 cells treated with RGD-PEG-ECO/siDANCR nanoparticles show considerable reduction in their ability to form 3D tumor spheroids, compared to NC-treated cells. (h) Clonogenic assay shows significant suppression of proliferative potential of MDA-MB-231 and BT549 cells treated with RGD-PEG-ECO/siDANCR nanoparticles, compared to NC nanoparticles (*p<0.01). Colonies formed after plating 2000 siDANCR- and NC-treated cells were stained with 0.01% crystal violet after 10 days, counted, and represented as % of survived colonies. Error bars denote s.e.m., scale bar=100 μm.

FIGS. 18(A-E) illustrate immunoassays, graphs, and images showing RGD-PEG-ECO/siDANCR nanoparticles suppress the expression of proteins involved in multiple oncogenic pathways. (a) DANCR silencing in MDA-MB-231 and BT549 cells induces significant decrease in the expression of β-catenin (Wnt signaling); ZEB 1 and N-cadherin (EMT markers); and the anti-apoptotic protein, survivin. β-Actin is used as the loading control. (b) RGD-PEG-ECO/siDANCR nanoparticle-mediated silencing of DANCR in MDA-MB-231 and BT549 cells downregulates the expression of the PRC2 complex proteins EZH2 and SUZ12, along with decreased H3K27 tri-methylation marks. (c) DANCR regulates PRC2 complex by directly binding to EZH2 in MDA-MD-231 and BT549 cells (*p<0.005). (d) Phospho-kinase arrays demonstrate the differential phosphorylation patterns of 43 kinases with treatment of RGD-PEG-ECO/siDANCR nanoparticles in MDA-MB-231 and BT549 cells. Proteins highlighted in the boxes show significant differences in phosphorylation status between NC and DANCR knockdown. (e) The bar graphs represent the corresponding kinases/proteins that show significant changes (p<0.05) in expression between control and DANCR silencing, calculated by comparing the mean pixel intensities of the duplicate spots.

FIGS. 19(A-I) illustrate plots, images, and graphs showing systemic therapy of RGD-PEG-ECO/siDANCR nanoparticles significantly reduces primary tumor burden in TNBC xenografts. RGD-PEG-ECO/NC and RGD-PEG-ECO/siDANCR nanoparticles were formulated at N/P=8, PEG-RGD/ECO=2.5 mol % and [siRNA]=0.3 mg/mL, and characterized for (a) particle size and (b) zeta potential (*p<0.05). (c) Weekly intravenous injections of RGD-PEG-ECO/siDANCR nanoparticles at a siRNA dose of 1.0 mg/kg for 6 weeks result in significant reduction in tumor volumes (*p<0.05). MDA-MB-231 and BT549 xenografts (2 & 4×10$^6$ cells, respectively) were implanted into the mammary fat pads of athymic mice and treatment was started at average tumor volume of 70-90 mm$^3$. (d) Compared to RGD-PEG-ECO/NC, RGD-PEG-ECO/siDANCR nanoparticles mediate significant inhibition of tumor progression. (e) Tumor status at the end of 6 weeks. (f) H&E staining of paraffin-fixed tumor samples from mice treated with RGD-PEG-ECO/siDANCR and NC (scale bar=100 μm) shows large zonal necrosis (arrows) in NC but only focal necrosis with siDANCR treatment. Compared to RGD-PEG-ECO/NC-treated tumors, RGD-PEG-ECO/siDANCR-treated tumors demonstrate (g) significantly reduced DANCR levels (**p<0.005), and significantly lower mRNA expression of (h) EZH2 and (i) survivin, indicating that the targeted RGD-PEG-ECO-siDANCR therapy likely causes epigenetic alterations and apoptosis in the TNBC tumors (*p<0.05).

FIGS. 20(A-D) illustrate a plot and images showing systemic administrations of RGD-PEG-ECO/siDANCR nanoparticles do not cause evident side-effects in the treated mice. (a) Both siDANCR- and NC-treated mice show no changes in their general health and no significant differences in the body weights during the 6 weeks of nanoparticle injections. H&E staining of the tumor sections demonstrates no significant changes in the morphology of the vital organs in NC- and siDANCR-treated mice, with the (b) liver, (c) kidney, and (d) lungs showing normal hepatocyte, renal, and alveolar histology, respectively. (error bars denote s.e.m., scale bar=100 μm).

Figure 21:
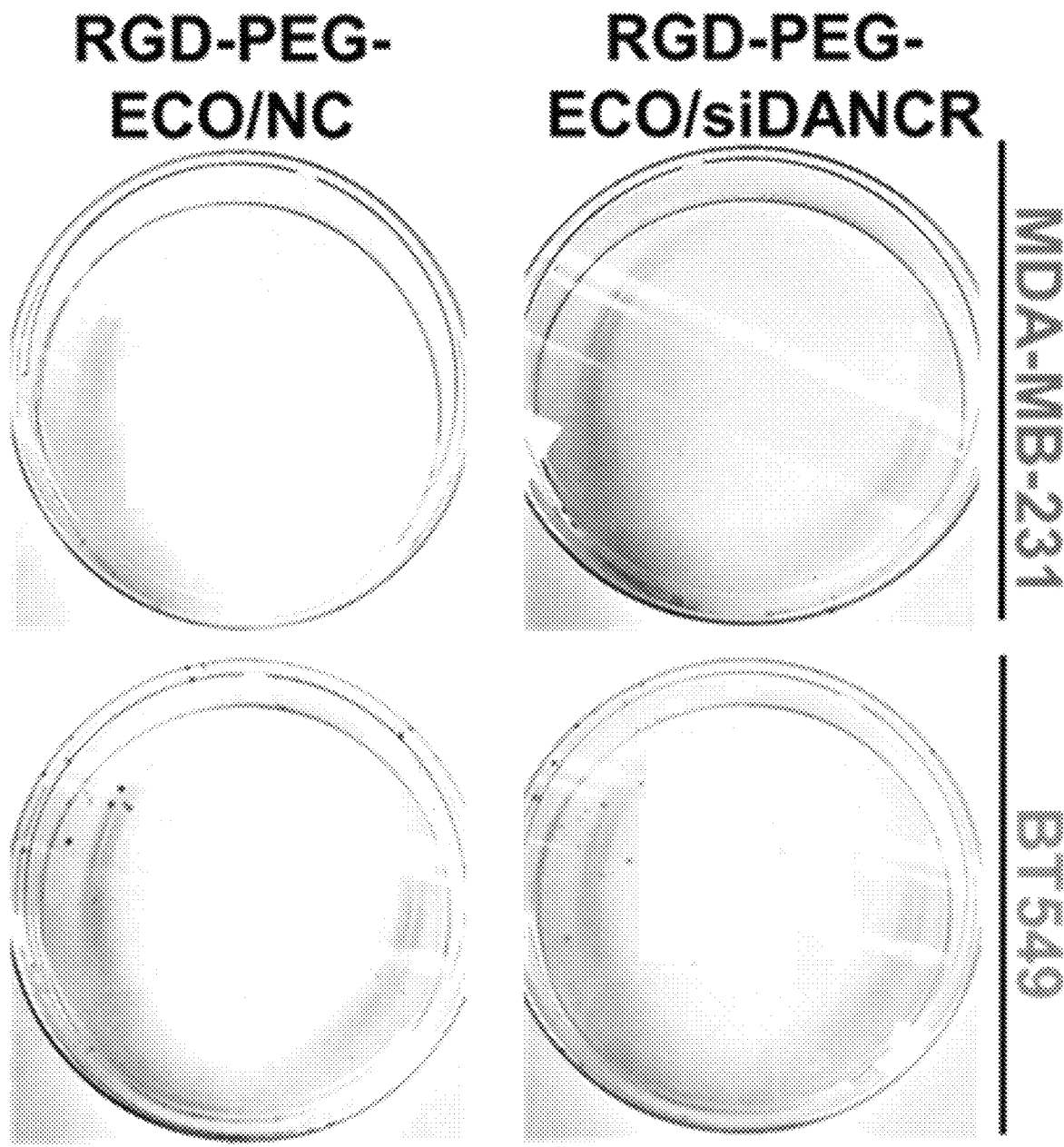

FIG. 21 illustrate images showing RGD-PEG-ECO/siDANCR nanoparticles inhibit TNBC proliferation and survival. Clonogenic assay shows significant suppression of proliferative potential of MDA-MB-231 and BT549 cells treated with RGD-PEG-ECO/siDANCR nanoparticles, compared to NC nanoparticles. Colonies formed after plating of 2000 siDANCR- and NC-treated cells were stained with 0.01% crystal violet after 7-10 days.

Figure 22:
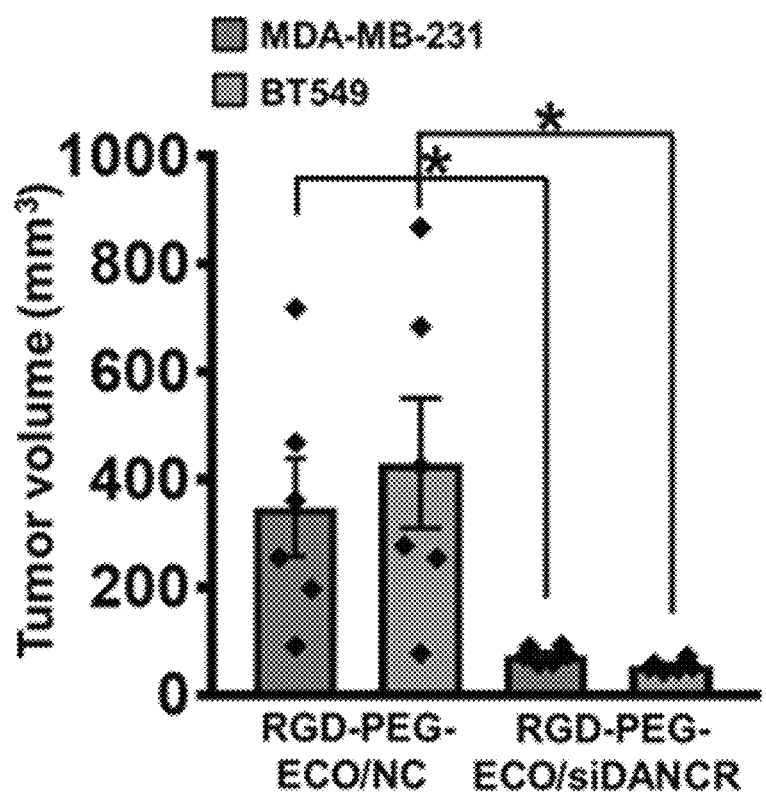

FIG. 22 illustrate a graph showing systemic administration of RGD-PEG-ECO/siDANCR nanoparticles significantly reduces primary tumor burden in TNBC xenografts. Combination plot showing the final tumor volumes (bars) and the individual tumor volumes (dots) of NC- and siDANCR-treated mice bearing MDA-MB-231 and BT549 xenografts at 6 weeks post-treatment (error bars denote s.e.m., *p<0.05).

Figure 23:
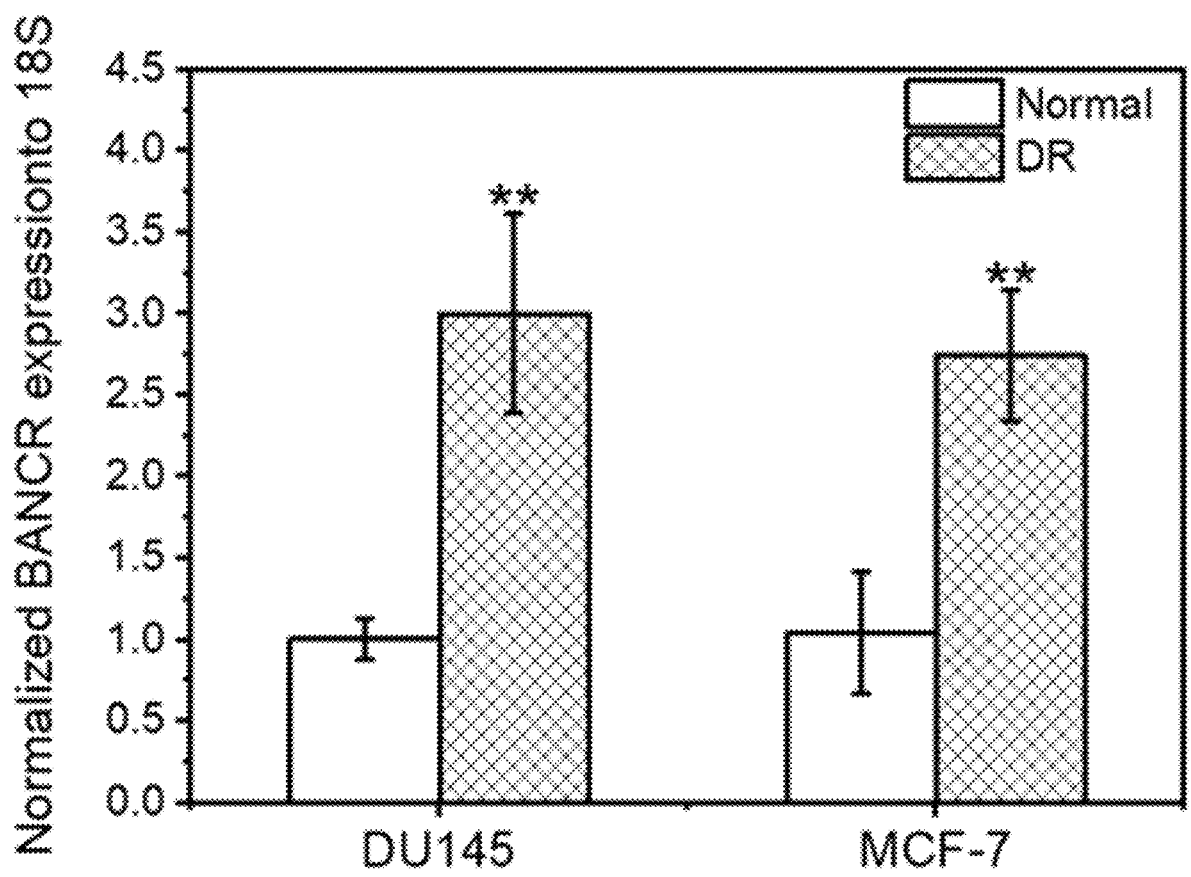

FIG. 23 illustrates a graphs showing BANCR expression in MCF-7 and DU145 cell lines and their corresponding drug-resistant cell lines. (data represent mean±S.D., p<0.01, *p<0.001).

FIGS. 24(A-C) illustrate plots and a graph showing formulation of ECO/siRNA nanoparticles. (a) Size distribution of ECO/siRNA nanoparticles determined by DLS. (b) Zeta potential distribution of ECO/siRNA nanoparticles determined by DLS. (c) BANCR expression MCF-7-DR and DU145-DR cells after treatment with ECO/siNS and ECO/siRNA nanoparticles (data represent mean±S.D., n=3, **p<0.01).

FIGS. 25(A-C) illustrate a graphs and a plot showing Expression of HOTTIP (a) and HOXA13 (b), and correlation between HOTTIP and HOXA13 (c) in different PCa cell lines (data represent mean±S.D., *p<0.05, p<0.01, *p<0.001).

FIG. 26 illustrates a plot showing correlation between HOTTIP and HOXA13 in PCa tissues.

FIGS. 27(A-B) illustrate an image showing morphology of PC3 (a) and DU145-DR (b) cells.

FIGS. 28(A-D) illustrate plots and an immunoassay showing formulation of ECO/siRNA nanoparticles. (a) Size distribution of ECO/siRNA nanoparticles determined by DLS. (b) Zeta potential distribution of ECO/siRNA nanoparticles determined by DLS. (c) Gel retardation assay of ECO/siRNA nanoparticles. (d) HOTTIP expression PCa cells after treatment with ECO/siNS and ECO/siRNA nanoparticles (data represent mean±S.D., n=4, *p<0.05).

FIGS. 29(A-B) illustrate graphs showing cell viability of PC3 (a) and DU145-DR (b) cells treated with or without ECO/siRNA nanoparticles at day 1 to 3 (data represent mean±S.D., *p<0.05, ***p<0.001).

FIG. 30 illustrates images showing Live/dead staining of PC3 and DU145-DR cells treated with or without ECO/siRNA nanoparticles at day 3.

Figure 31:
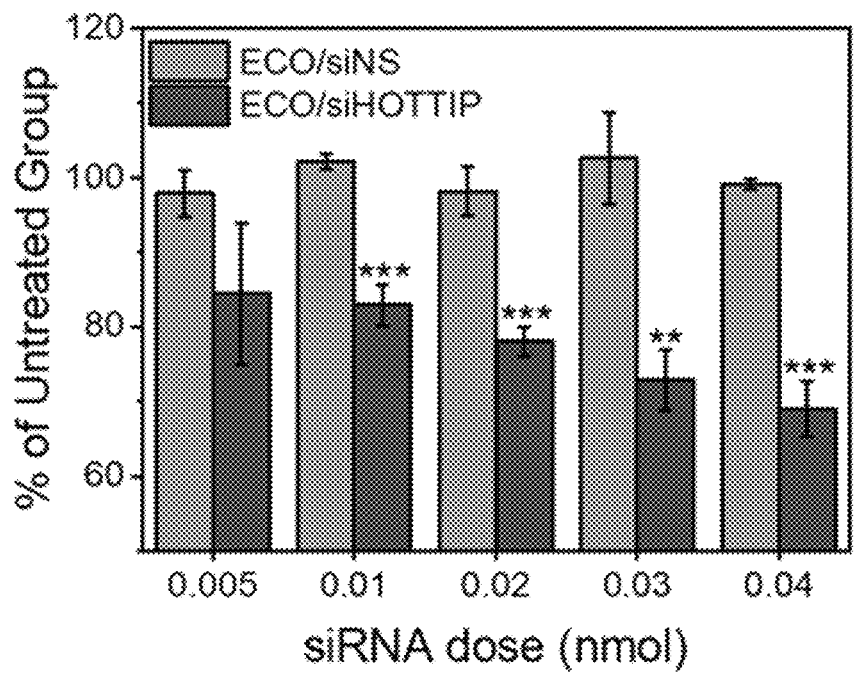

FIG. 31 illustrates a graph showing cell viability of PC3 cells treated with different dose of ECO/siRNA nanoparticles at day 1 (data represent mean±S.D., *p<0.05, ***p<0.001).

Figure 32:
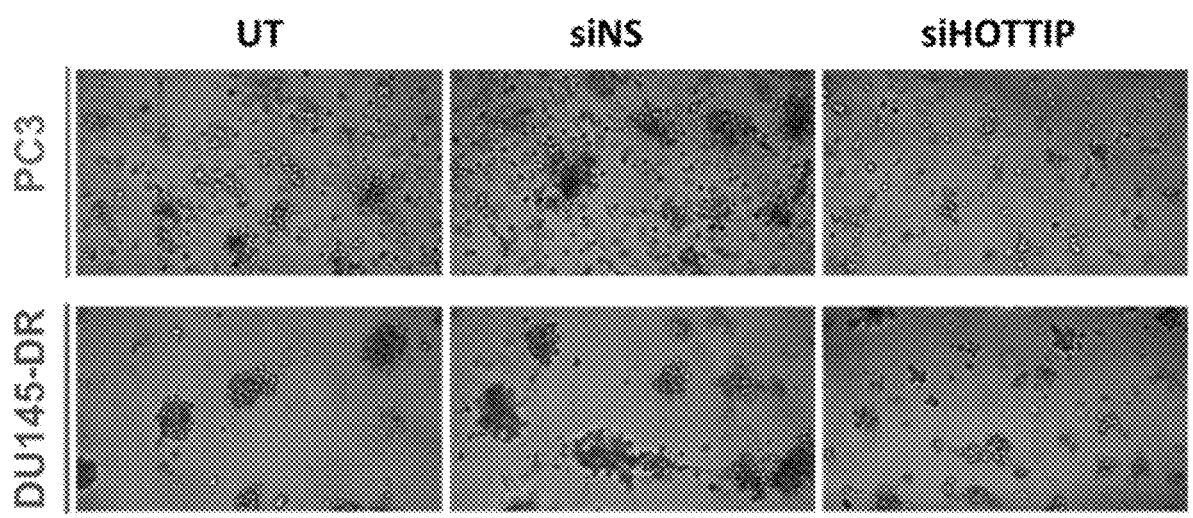

FIG. 32 illustrates images showing 3D tumor spheroid growth in Matrigel of PC3 and DU145-DR cells treated with or without ECO/siRNA nanoparticles at day 7.

Figure 33:
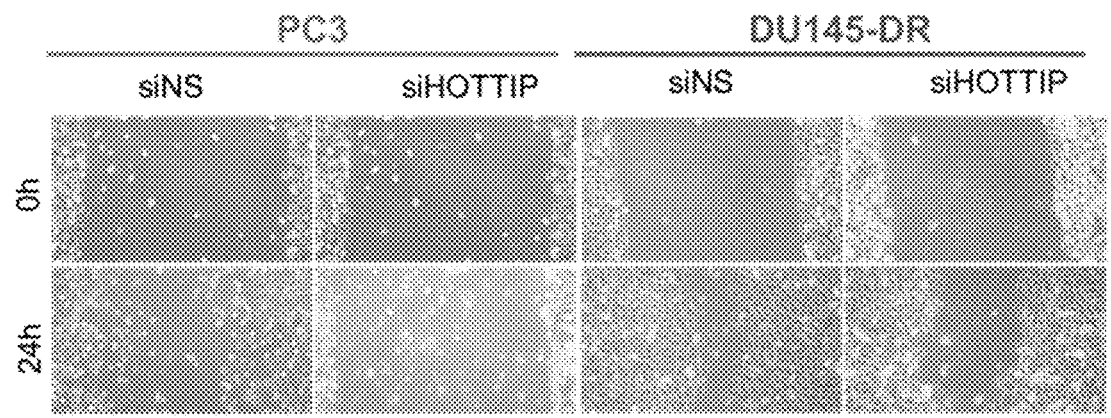

FIG. 33 illustrates images showing cell migration ability of PCa cells (PC3 and DU145-DR) after treatment with ECO/siNS and ECO/siHOTTIP nanoparticles assessed by standard scratch-wound assays.

Figure 34:
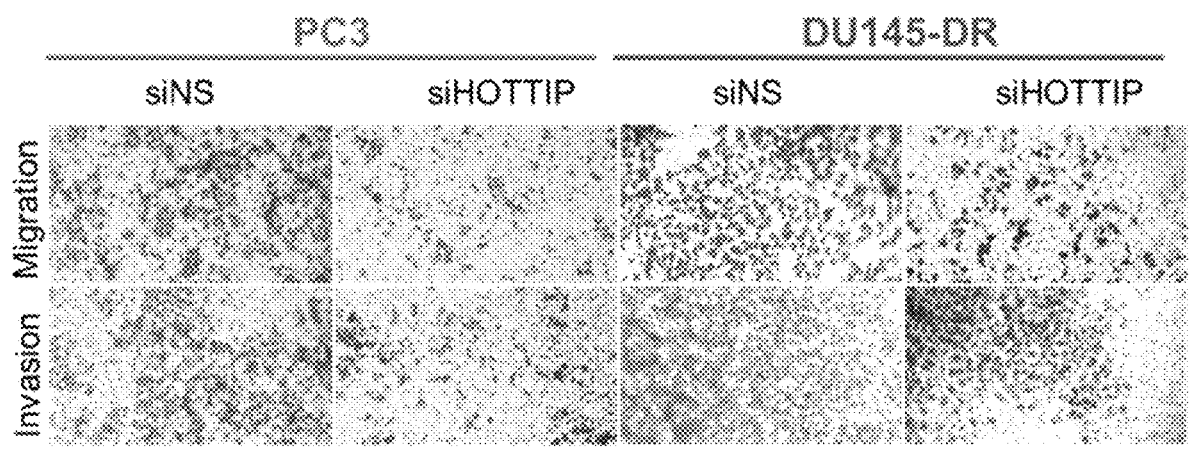

FIG. 34 illustrates images showing cell migration and invasion ability of PCa cells (PC3 and DU145-DR) after treatment with ECO/siNS and ECO/siHOTTIP nanoparticles assessed by Transwell study.

Figure 35:
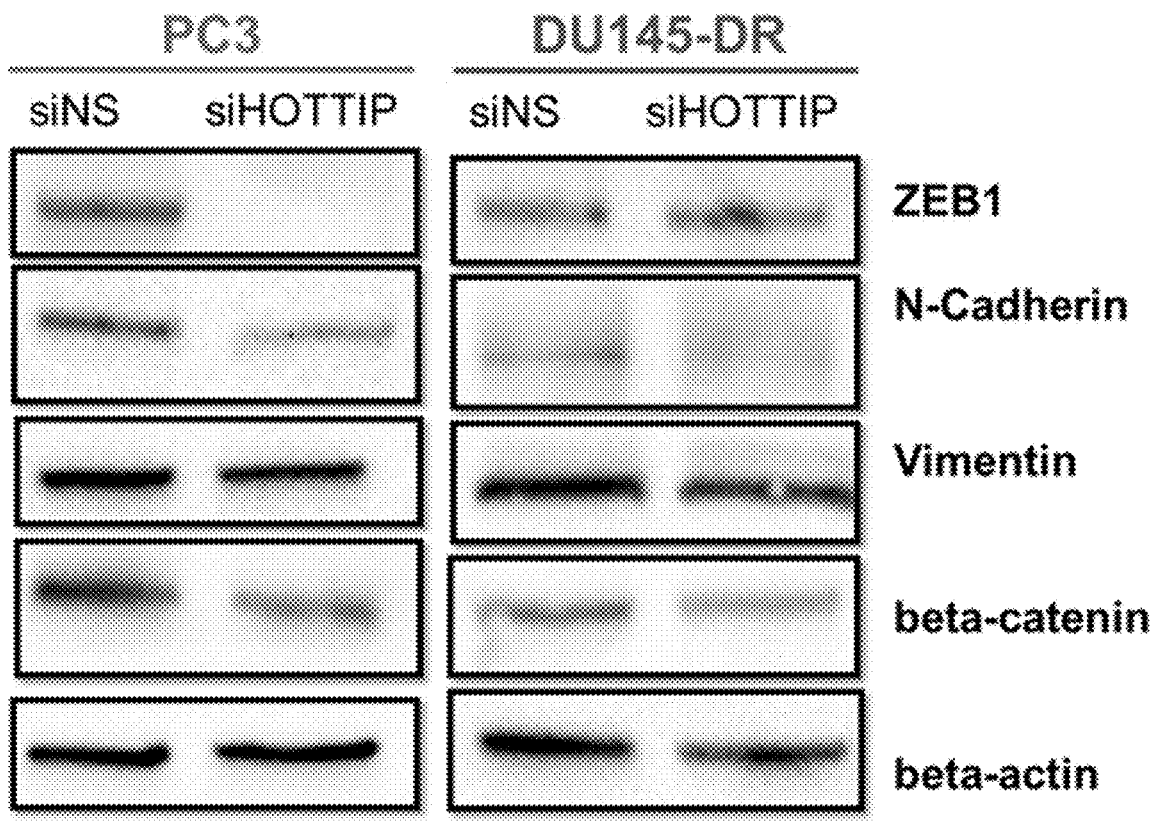

FIG. 35 illustrates Western blot images of EMT markers in PCa cells (PC3 and DU145-DR) after treatment with ECO/siNS and ECO/sieIF4E nanoparticles.

Figure 36:
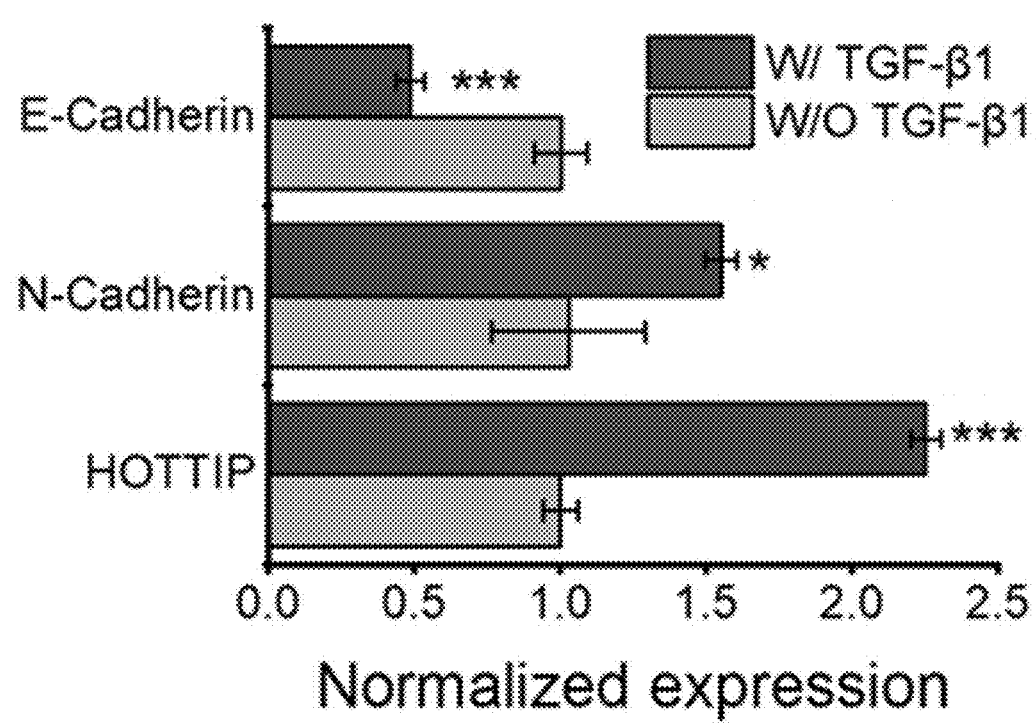

FIG. 36 illustrates a graph showing expression of HOTTIP and EMT makers in DU145 cells treated with or without TGF-β1 at mRNA level (data represet mean±S.D., n=4, *p<0.05, **p<0.01).

Figure 37:
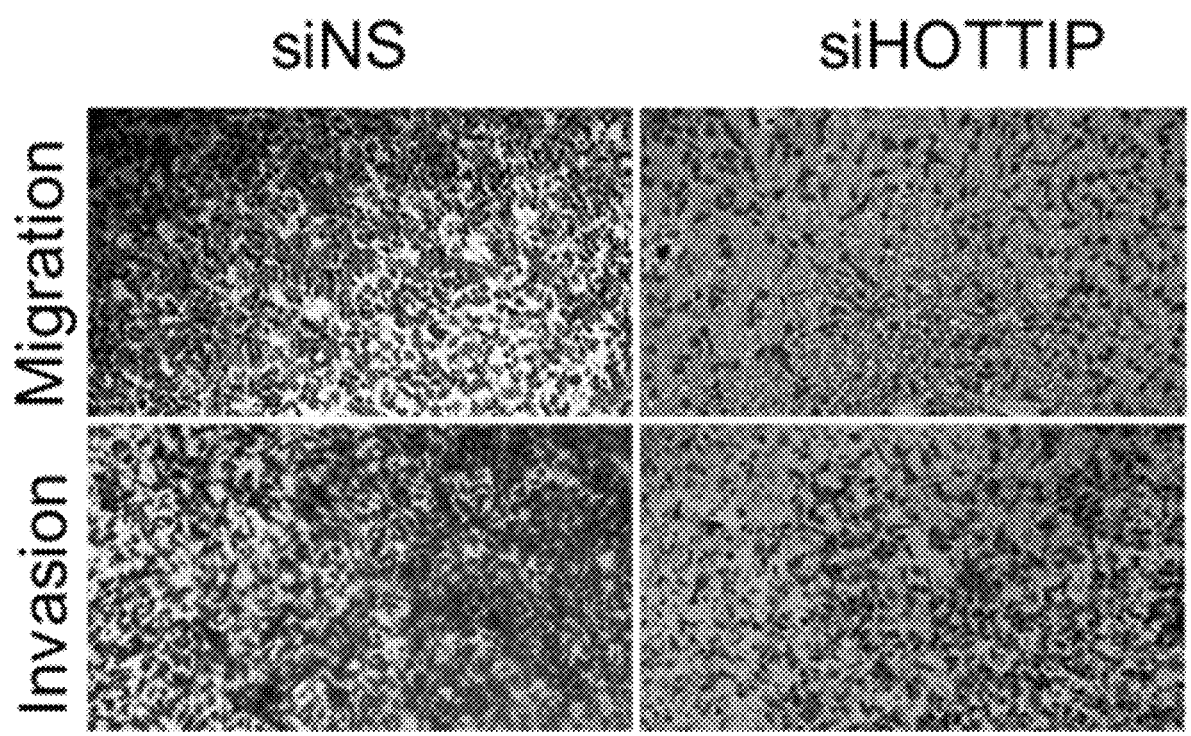

FIG. 37 illustrates images showing cell migration and invasion ability of DU145-TGF-β1 cells after treatment with ECO/siNS and ECO/siHOTTIP nanoparticles assessed by Transwell study.

DETAILED DESCRIPTION

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

It must be noted that, as used in the specification and the appended claims, the singular forms "a," "an" and "the"

include plural referents unless the context clearly dictates otherwise. Thus, for example, reference to "a pharmaceutical carrier" includes mixtures of two or more such carriers, and the like. "Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

The term "alkenyl group" is defined herein as a C2-C20 alkyl group possessing at least one C=C double bond.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "acyl" group as used herein is represented by the formula C(O)R, where R is an organic group such as, for example, an alkyl or aromatic group as defined herein.

The term "alkylene group" as used herein is a group having two or more $CH_2$ groups linked to one another. The alkylene group can be represented by the formula $(CH_2)_a$, where a is an integer of from 2 to 25.

The term "aromatic group" as used herein is any group containing an aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The terms "cancer" or "tumor" refer to any neoplastic growth in a subject, including an initial tumor and any metastases. The terms "cancer cell" or "tumor cell" can refer to cells that divide at an abnormal (i.e., increased) rate.

The phrase "nitrogen containing substituent" is defined herein as any amino group. The term "amino group" is defined herein as a primary, secondary, or tertiary amino group. In the alternative, the nitrogen containing substituent can be a quaternary ammonium group. The nitrogen containing substituent can be an aromatic or cycloaliphatic group, where the nitrogen atom is either part of the ring or directly or indirectly attached by one or more atoms (i.e., pendant) to the ring. The nitrogen containing substituent can be an alkylamino group having the formula $RNH_2$, where R is a branched or straight alkyl group, and the amino group can be substituted or unsubstituted.

The term "long non-coding ribonucleic acid", "long non-coding RNA" or "lncRNA" refers to a ribonucleic acid sequence that is encoded within a genomic intronic or intergenic region. Such lncRNAs are not transcribed into proteins but act directly to regulate various activities including, but not limited to, transcription or translation. For example, an lncRNA may be exemplified by an aptamer that regulates transcription rates of a particular gene or allele.

The term "nucleic acid" refers to oligonucleotides, nucleotides, polynucleotides, or to a fragment of any of these, to DNA or RNA (e.g., mRNA, rRNA, tRNA, miRNA, siRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids containing known analogues of natural nucleotides, as well as nucleic acid-like structures with synthetic backbones.

The term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, aves, etc.), which is to be the recipient of a particular treatment. Typically, the terms "patient" and "subject" are used interchangeably herein in reference to a human subject.

The terms "inhibit," "silencing," and "attenuating" can refer to a measurable reduction in expression of a target mRNA (or the corresponding polypeptide or protein) as compared with the expression of the target mRNA (or the corresponding polypeptide or protein) in the absence of an interfering RNA molecule of the present invention. The reduction in expression of the target mRNA (or the corresponding polypeptide or protein) is commonly referred to as "knock-down" and is reported relative to levels present following administration or expression of a non-targeting control RNA.

The term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The terms "siRNA" refers to either small interfering RNA, short interfering RNA, or silencing RNA. Generally, siRNA comprises a class of double-stranded RNA molecules, approximately 20-25 nucleotides in length. Most notably, siRNA is involved in RNA interference (RNAi) pathways and/or RNAi-related pathways, wherein the compounds interfere with gene expression.

The term "shRNA" refers to any small hairpin RNA or short hairpin RNA. Although it is not necessary to understand the mechanism of an invention, it is believed that any sequence of RNA that makes a tight hairpin turn can be used to silence gene expression via RNA interference. Typically, shRNA uses a vector stably introduced into a cell genome and is constitutively expressed by a compatible promoter. The shRNA hairpin structure may also cleaved into siRNA, which may then become bound to the RNA-induced silencing complex (RISC). This complex binds to and cleaves mRNAs which match the siRNA that is bound to it.

The term "microRNA", "miRNA", or ".mu.RNA" refers to any single-stranded RNA molecules of approximately 21-23 nucleotides in length, which regulate gene expression. miRNAs may be encoded by genes from whose DNA they are transcribed but miRNAs are not translated into protein (i.e. they are non-coding RNAs). Each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

Embodiments described herein relate to compounds used to form multifunctional pH-sensitive carriers that are designed to condense nucleic acids, such as siRNA, and deliver the condensed nucleic acids to cells. The compounds can include a protonable amino head group, fatty acid or lipid tails, and two cysteine residues.

The protonable amino head group can complex with nucleic acids to form nanoparticles for delivery of nucleic acids to cells. The amines in the head groups contribute to the essential pH-sensitive characteristic of the carrier system, which is important for improving endosomal escape and RNAi-mediated silencing efficiency. Greater protonation of the amino head groups can occur in the relatively acidic environment (pH=5-6) of the endosome and lysosome compartments after cellular uptake. This enhances electrostatic interactions between the cationic carriers and the anionic phospholipids of endosomal/lysosomal membranes, promoting the bilayer destabilization and nanoparticle charge neutralization events required for efficient cytosolic release of their nucleic acid payload. By affecting the number of amines, and thus overall pKa, of the cationic carrier, the choice of head group can ultimately determine the degree to which such protonation can occur. The pH-sensitive property of the carrier system is essential so that the nanoparticles do not affect the integrity of the outer cell membrane and cause cell death, but instead are able to selectively fuse with and destabilize the endosomal and lysosomal membranes.

The cysteine residues can form disulfide bridges via autooxidation and react with functional groups of other compounds, such as those containing thiol groups. Once the nucleic acid is complexed with the compound, the thiol groups can produce disulfide (S—S) bonds or bridges by autooxidation to form oligomers and polymers or cross-linking. The disulfide bonds can stabilize the nanoparticles of the nucleic acid and compound and help achieve release of the nucleic acid once the nanoparticle is in the cell.

For example, when the nucleic acid is siRNA, the cleavage of disulfide bonds in the siRNA delivery system in reductive cytoplasm can facilitate cytoplasm-specific release of siRNA. The compounds will be stable in the plasma at very low free thiol concentration (e.g., 15 μM). When the compounds are incorporated into target cells, the high concentration of thiols present in the cell (e.g., cytoplasm) will reduce the disulfide bonds to facilitate the dissociation and release of the nucleic acid.

The disulfide bonds can be readily produced by reacting the same or different compounds before complexation with nucleic acid or during the complexation in the presence of an oxidant. The oxidant can be air, oxygen or other chemical oxidants. Depending upon the dithiol compound selected and oxidative conditions, the degree of disulfide formation can vary in free polymers or in complexes with nucleic acids. Thus, the compounds including two cysteine residues are monomers, and the monomers can be dimerized, oligomerized, or polymerized depending upon the reaction conditions.

The fatty acid or lipid tails groups can participate in hydrophobic condensation and help form compact, stable nanoparticles with the nucleic acids and introduce amphiphilic properties to facilitate pH sensitive escape of nanoparticles from endosomal and lysosomal compartments. This is particularly useful when the compounds are used as in vivo delivery devices.

In general, the transfection efficiency of carriers has been shown to decrease with increasing alkyl chain length and saturation of the lipid tail groups. When saturated, shorter aliphatic chains (C12 and C14) favor higher rates of inter-membrane lipid mixing and reportedly allow for better transfection efficiencies in vitro, as compared to in vivo, whereas the opposite is true for longer chains (C16 and C18). Typically, saturated fatty acids greater than 14 carbons in length are not favorable for nucleic acid transfections due to their elevated phase transition temperature and overall less fluidity than those that are unsaturated. However, it has been discovered that there exists a limit, at which point an increase in unsaturation and lipid fluidity is inversely correlated to transfection efficiency, primarily because some degree of rigidity is required for particle stability, as evidenced by the widespread use of cholesterol in lipid nanoparticle formulations.

Advantageously, multifunctional pH-sensitive carriers formed using the compounds have improved stability when administered systemically to a subject, protect condensed nucleic acids from degradation, and promote endosomal escape and cytosolic release upon cellular uptake.

In some embodiments, a targeting group can be attached to the compound by, for example, a thiol group of a cysteine residue. The targeting group can be useful in the delivery of nucleic acids into cells. The targeting group can be a peptide, an antibody, an antibody fragment or one of their derivatives. For example, target-specific peptides can be conjugated directly to the compound or indirectly via a linker (e.g., polyethylene glycol) prior or during the formation of nanoparticles. Depending upon the selection of the targeting group, the targeting group can be covalently bonded to either the thiol group of the cysteine residues.

In one aspect, the targeting group is indirectly attached to the compound by a linker. Examples of linkers include, but are not limited to, a polyamine group, a polyalkylene group, a polyamino acid group or a polyethylene glycol group. The selection of the linker as well as the molecular weight of the linker can vary depending upon the desired properties. In one aspect, the linker is polyethylene glycol having a molecular weight from 500 to 10,000, 500 to 9,000, 500 to 8,000, 500 to 7,000, or 2,000 to 5,000. In certain aspects, the targeting group is first reacted with the linker in a manner such that the targeting group is covalently attached to the linker. For example, the linker can possess one or more groups that can react with an amino group present on a peptide. The linker also possesses additional groups that react with and form covalent bonds with the compounds described herein. For example, the linker can possess maleimide groups that readily react with the thiol groups. The selection of functional groups present on the linker can vary depending upon the functional groups present on the compound. In one aspect, the targeting group is a peptide such as, an RGD peptide or bombesin peptide that is covalently attached to polyethylene glycol.

In some embodiments, the linker can include an acid labide bond, such as formed by incorporation of a hydazone into the linker, that is hydrolyzable in an endolysomal environment following uptake to cells, such as cancer cells. For example, the linker can be covalently linked to the compound by at least one of a covalent hydrolyzable ester, covalent hydrolyzable amide, covalent photodegradable urethane, or covalent hydrolyzable acrylate-thiol linkage. Following cellular uptake of the compound, within the endosomes, the increasingly acidic environment can cleave the acid labile linkage to promote shedding of a polymer linker, such as PEG, and expose the core of the compound/nucleic complex nanoparticle.

In other aspects, it is also desirable to attach the targeting group to a nanoparticle produced by the compounds described herein. For example, after a nanoparticle composed of a nucleic acid has been produced using the compounds and techniques described herein, the targeting group can be attached to the nanoparticle via a linker.

In some embodiments, the compound can include formula (I):

For example, $R^1$ can include at least one of $CH_2NH_2$, $CH_2CH_2NH_2$, $CH_2CH_2CH_2NH_2$, $CH_2CH_2CH_2CH_2NH_2$, $CH_2CH_2CH_2CH_2CH_2NH_2$, $CH_2NHCH_2CH_2CH_2NH_2$, $CH_2CH_2NHCH_2CH_2CH_2NH_2$, $CH_2CH_2CH_2NHCH_2CH_2CH_2CH_2NHCH_2CH_2CH_2NH_2$, $CH_2CH_2NHCH_2CH_2CH_2NH_2$, $CH_2CH_2NHCH_2CH_2CH_2NHCH_2CH_2CH_2HN_2$, or $CH_2CH_2NH(CH_2CH_2NH)_dCH_2CH_2NH_2$, where d is from 0 to 10.

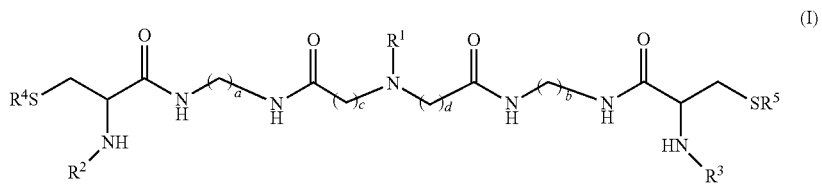

(I)

wherein $R^1$ is an akylamino group or a group containing at least one aromatic group; $R^2$ and $R^3$ are independently an aliphatic group or a hydrophobic group, derived, for example, from a fatty acid;

$R^4$ and $R^5$ are independently H, a substituted or unsubstituted akyl group, an akenyl group, an acyl group, an aromatic group, polymer, a targeting group, or a detectable moiety; a, b, c, and d are independently an integer from 1 to 10 (e.g., a, b, c, and d are each 2); and pharmaceutically acceptable salts thereof.

In some embodiments, $R^1$ can include at least one of:

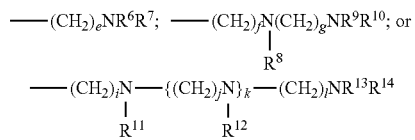

where $R^6$, $R^7$, $R^8$, $R^9$, $R^{10}$, $R^{11}$, $R^{12}$, $R^{13}$, and $R^{14}$ are independently hydrogen, an alkyl group, a hydrophobic group, or a nitrogen containing substituent; and e, f, g, i, j, k, and l, are an integer from 1 to 10.

In some embodiments, $R^1$ can be $CH_2CH_2NH_2$ or $CH_2CH_2NHCH_2CH_2CH_2NHCH_2CH_2CH_2HN_2$. In other embodiments, $R^1$ is $CH_2CH_2NH_2$.

In other embodiments, $R^2$ and $R^3$ are independently an aliphatic group or a hydrophobic group derived from fatty acid, such as oleic acid or linoleic acid, and are the same or different. The additional double bond in linoleic acid introduces an extra kink into the hydrocarbon backbone, giving the compound a broader conical shape than oleic acid and increasing its fluidity. When incorporated into a nanoparticle structure, the extra degree of unsaturation elevates the propensity to form the hexagonal phase during an impending membrane fusion event of cellular uptake.

In some embodiments, $R^4$ and $R^5$ are independently H, a substituted or unsubstituted polymer, a targeting group, or a detectable moiety.

In some embodiments, the compound can have the formulas:

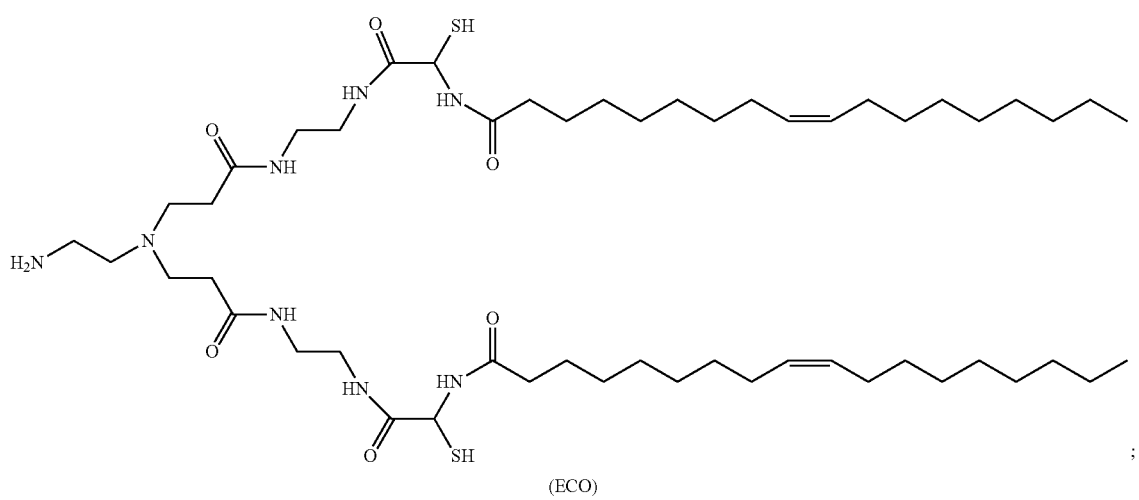

(ECO)

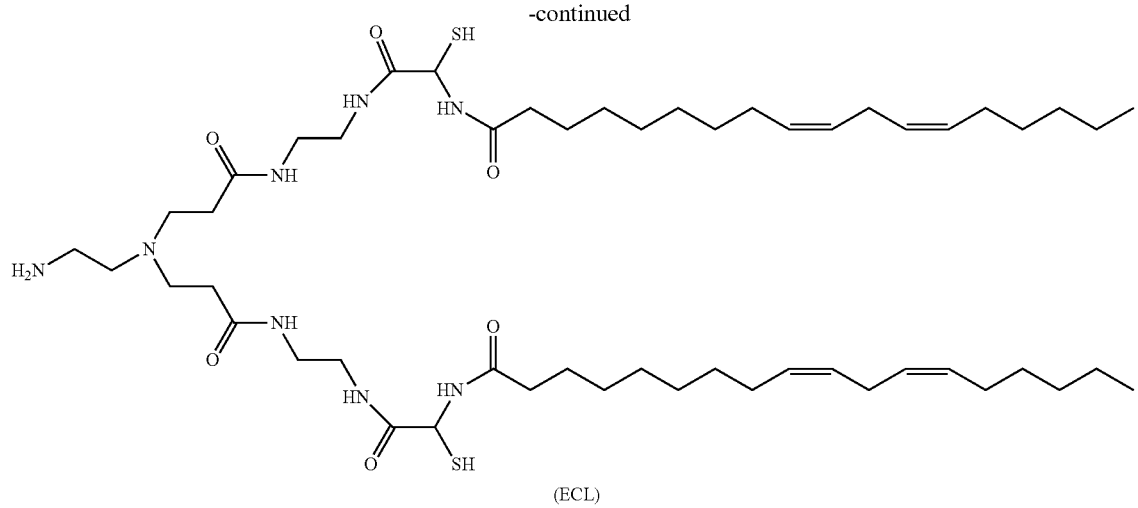

(ECL)

or pharmaceutically acceptable salts thereof.

Figure 1:
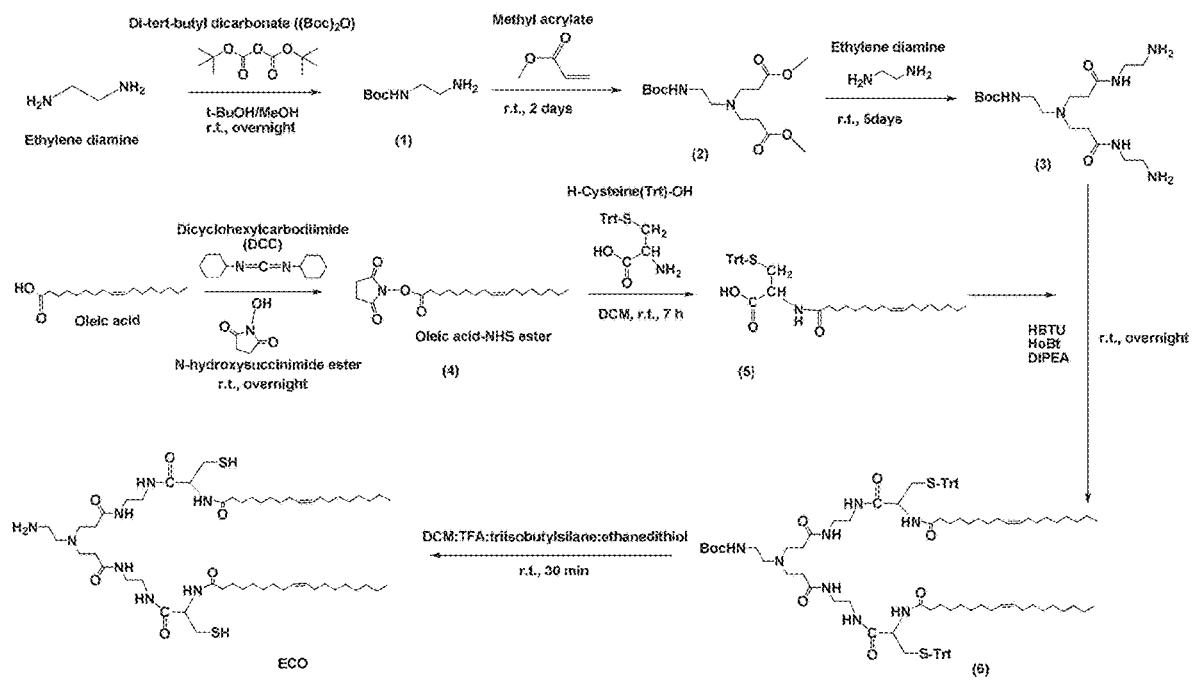
FIG. 1 illustrates a synthetic procedure for ECO.

The compounds having the general formula I can be synthesized using solid phase techniques known in the art. FIG. 1 illustrates an example of a synthetic procedure for preparing the compounds. In general, the approach in FIG. 1 involves the systematic protection/elongation/deprotection to produce a dithiol compound. The hydrophobic group is produced by reacting oleic acid with the amino group present on the cysteine residue. Although FIG. 1 depicts one approach for producing the compounds of formula I, other synthetic techniques can be used.

Any of the compounds described herein can exist or be converted to the salt thereof. In one aspect, the salt is a pharmaceutically acceptable salt. The salts can be prepared by treating the free acid with an appropriate amount of a chemically or pharmaceutically acceptable base. Representative chemically or pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C., such as at room temperature. The molar ratio of the compound to base used is chosen to provide the ratio desired for any particular salts. For preparing, for example, the ammonium salts of the free acid starting material, the starting material can be treated with approximately one equivalent of base to yield a salt.

In another aspect, any of the compounds described herein can exist or be converted to the salt with a Lewis base thereof. The compounds can be treated with an appropriate amount of Lewis base. Representative Lewis bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, THF, ether, thiol reagent, alcohols, thiol ethers, carboxylates, phenolates, alkoxides, water, and the like. In one aspect, the reaction is conducted in water, alone or in combination with an inert, water-miscible organic solvent, at a temperature of from about 0° C. to about 100° C. such as at room temperature. The molar ratio of the compound to base used is chosen to provide the ratio desired for any particular complexes. For example, the ammonium salts of the free acid starting material, the starting material can be treated with approximately one equivalent of chemically or pharmaceutically acceptable Lewis base to yield a complex.

If the compounds possess carboxylic acid groups, these groups can be converted to pharmaceutically acceptable esters or amides using techniques known in the art. Alternatively, if an ester is present on the dendrimer, the ester can be converted to a pharmaceutically acceptable ester using transesterification techniques.

The compounds described herein have numerous applications with respect to the delivery of nucleic acids to a subject. In some embodiments, the compounds described herein can be used in gene therapy to deliver nucleic acid or genetic materials to cells and tissues.

The nucleic acid can be an oligonucleotide, deoxyribonucleic acid (DNA), ribonucleic acid (RNA), or peptide nucleic acid (PNA). The nucleic acid of interest introduced by the present method can be nucleic acid from any source, such as a nucleic acid obtained from cells in which it occurs in nature, recombinantly produced nucleic acid, or chemically synthesized nucleic acid. For example, the nucleic acid can be cDNA or genomic DNA or DNA synthesized to have the nucleotide sequence corresponding to that of naturally-occurring DNA. The nucleic acid can also be a mutated or altered form of nucleic acid (e.g., DNA that differs from a naturally occurring DNA by an alteration, deletion, substitution or addition of at least one nucleic acid residue) or nucleic acid that does not occur in nature.

In one aspect, the nucleic acid can be a functional nucleic acid. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, siRNA, miRNA, shRNA, lncRNA and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acids can be a small gene fragment that encodes dominant-acting synthetic genetic elements (SGEs), e.g., molecules that interfere with the function of genes from which they are derived (antagonists) or that are dominant constitutively active fragments (agonists) of such genes. SGEs can include, but are not limited to, polypeptides, inhibitory antisense RNA molecules, ribozymes, nucleic acid decoys, and small peptides. The small gene fragments and SGE libraries disclosed in U.S. Patent Publication No. 2003/0228601, which is incorporated by reference, can be used herein.

The functional nucleic acids of the present method can function to inhibit the function of an endogenous gene at the level of nucleic acids, e.g., by an antisense, RNAi or decoy mechanism. Alternatively, certain functional nucleic acids can function to potentiate (including mimicking) the function of an endogenous gene by encoding a polypeptide that retains at least a portion of the bioactivity of the corresponding endogenous gene, and may in particular instances be constitutively active.

Other therapeutically important nucleic acids include antisense polynucleotide sequences useful in eliminating or reducing the production of a gene product, as described by Tso, P. et al Annals New York Acad. Sci. 570:220-241 (1987). Also contemplated is the delivery of ribozymes. These antisense nucleic acids or ribozymes can be expressed (replicated) in the transfected cells. Therapeutic nucleic acids or polynucleotides useful herein can also code for immunity-conferring polypeptides, which can act as endogenous immunogens to provoke a humoral or cellular response, or both. The nucleic acids or polynucleotides employed can also code for an antibody. In this regard, the term "antibody" encompasses whole immunoglobulin of any class, chimeric antibodies and hybrid antibodies with dual or multiple antigen or epitope specificities, and fragments, such as $F(ab)_2$, $Fab^2$, Fab and the like, including hybrid fragments. Also included within the meaning of "antibody" are conjugates of such fragments, and so-called antigen binding proteins (single chain antibodies) as described, for example, in U.S. Pat. No. 4,704,692, the contents of which are hereby incorporated by reference.

In some embodiments, the nucleic acid is siRNA. siRNAs are double stranded RNA molecules (dsRNAs) with approximately 20 to 25 nucleotides, which are generated by the cytoplasmic cleavage of long RNA with the RNase III enzyme Dicer. siRNAs specifically incorporate into the RNA-induced silencing complex (RISC) and then guide the RNAi machinery to destroy the target mRNA containing the complementary sequences. Since RNAi is based on nucleotide base-pairing interactions, it can be tailored to target any gene of interest, rendering siRNA an ideal tool for treating diseases with gene silencing. Gene silencing with siRNAs has a great potential for the treatment of human diseases as a new therapeutic modality. Numerous siRNAs have been designed and reported for various therapeutic purposes and some of the siRNAs have demonstrated specific and effective silencing of genes related to human diseases. Therapeutic applications of siRNAs include, but are not limited to, inhibition of viral gene expression and replication in antiviral therapy, anti-angiogenic therapy of ocular diseases, treatment of autoimmune diseases and neurological disorders, and anticancer therapy. Therapeutic gene silencing has been demonstrated in mammals, which bodes well for the clinical application of siRNA. It is believed that siRNA can target every gene in human genome and has unlimited potential to treat human disease with RNAi.

In some embodiments, the nucleic acid can be an RNAi nucleic acid, such as siRNA, that inhibits the expression of long noncoding RNA (lncRNA), such as onco-lncRNA. LncRNAs are the largest class of noncoding RNAs, comprising over 20,000 genes annotated in the ENcylopedia of DNA Elements (ENCODE) and other reference databases. They are defined as transcripts produced by RNA polymerase II that are longer than 200 nucleotides and devoid of an open reading frame that can be translated into a protein. Derrien et al., 2012. "The GENCODE v7 catalog of human long noncoding RNAs: analysis of their gene structure, evolution, and expression. Genome Res 22: 1775-1789.

The function of most lncRNAs is unknown, but they have been proposed to play roles in both negatively and positively regulating gene expression. They can regulate expression of protein-coding genes at both the transcriptional and post-transcriptional levels. Posttranscriptional regulation could occur by competing with endogenous RNA to regulate microRNA levels, modulating mRNA stability and translation by homologous base pairing, or altering cellular localization of mRNAs. Transcriptional regulation can occur in cis with their effects restricted to the chromosome from which they are transcribed and in trans with their effects targeting gene transcription on other chromosomes. Both cis- and trans-acting lncRNAs can mediate their effects through their RNA transcripts; cis-acting lncRNAs can also regulate gene transcription as a result of the process of splicing or of transcription itself.

LncRNAs have been implicated in the regulation of tissue and developmental stage-specific transcription of genes. Mutations and dysregulation of lncRNAs have been increasingly linked with diverse human diseases. Wapinski et al., 2011. "Long noncoding RNAs and human disease" Trends Cell Biol 21: 354-361. Despite their pervasive transcription, very little is currently known about the regulation and function of lncRNAs. They have been proposed to play roles in both negatively and positively regulating gene expression. Their functions are determined by their secondary and tertiary structures and they do not share sequence homology with their targets. Recent reports have demonstrated a role for lncRNA in the regulation of Toll-like-receptor mediated immune responses and differentiation and function of human dendritic cells and T cells, implicating them in immune mechanisms that could modulate autoimmune disease. Mauger et al., 2013. "The genetic code as expressed through relationships between mRNA structure and protein function" FEBS Lett 587: 1180-1188; Carpenter et al., 2013. "A long noncoding RNA mediates both activation and repression of immune response genes" Science 341:789-792; Wang et al., 2014. "The STAT3-binding long noncoding RNA lnc-DC controls human dendritic cell differentiation" Science 344: 310-313; Hu et al., 2013. "Expression and regulation of intergenic long noncoding RNAs during T cell development and differentiation" Nat Immunol 14: 1190-1198; Spurlock et al., 2015. "Expression and functions of long noncoding RNAs during human T helper cell differentiation" Nat Commun 6: 6932; and Collier et al., 2012. "Cutting edge: influence of Tmevpg1, a long intergenic noncoding RNA, on the expression of Ifng by Th1 cells" J Immunol 189: 2084-2088.

In some embodiments, the nucleic acid can be an RNAi nucleic acid, such as siRNA, that inhibits the expression of onco-lncRNA. LncRNAs have recently been identified in the development of multiple oncogenic processes, including EMT, inflammation, cancer sternness, metastasis, and drug-resistance. Aberrant overexpression of oncogenic lncRNAs (onco-lncRNAs) is disease- and tissue-specific, and can influence global gene signatures and clinical outcomes by regulating multi-level gene expression. Examples of onco-lncRNAs include DANCR, NBAT1, LINC00511, LINC-UBC-1, ANCR, BCAR4, TINCR, BANCR, HOTTP, HOTAIR, CCAT1, HULC, LCAL1, MEG3, UCA1, FENDRR, and ANRIL. SiRNA that inhibits expression of onco-lncRNAs can be complexed with the carrier compounds described herein and administered to a subject with cancer to inhibit expression of the onco-lncRNAs and treat cancer in the subject. Examples of siRNA that inhibit the expression of onco-lncRNA described herein can include siDANCR, siBANCR, and siHOTTP. Other examples of siRNA that inhibit the expression of onco-lncRNA and that can be complexed with carrier compounds described herein can be used in treating cancer in a subject.

The nucleic acid can be complexed to the carrier compounds described herein by admixing the nucleic acid and the compound or corresponding disulfide oligomer or polymer. The pH of the reaction can be modified to convert the amino groups present on the compounds described herein to cationic groups. For example, the pH can be adjusted to protonate the amino group. With the presence of cationic groups on the compound, the nucleic acid can electrostatically bond (i.e., complex) to the compound. In one aspect, the pH is from 1 to 7.4.

In another aspect, the N/P ratio of the carrier compounds complexed with nucleic acids can be from 0.5 to 100, where N is the number of nitrogen atoms (e.g., amines) present on the compounds that can form a positive charge and P is the number of phosphate groups present on the nucleic acids. Thus, by modifying the compound with the appropriate number of amino groups in the head group, it is possible to tailor the bonding (e.g., type and strength of bond) between the nucleic acid and the compound. The N/P ratio can be adjusted depending on the cell type to which the nucleic acid is to be delivered. In some embodiments where the cell is cancer, the N/P ratio can be at least about 6, at least about 10, or at least about 15. In other embodiments, the N/P ration can be from about 6 to about 20, about 10 to about 20, about 12 to about 20, or about 6 about 14.

In one aspect, the nucleic acid/carrier complex is a nanoparticle. In one aspect, the nanoparticle has a diameter of about 1000 nanometers or less, for example, about 50 nm to about 200 nm, about 60 nm to about 180 nm, about 70 nm to about 160 nm, about 80 nm to about 140 nm, or about 90 nm to about 120 nm.

In other aspects, the compounds described herein can be designed so that the resulting nucleic acid nanoparticle escapes endosomal and/or lysosomal compartments at the endosomal-lysosomal pH. For example, the compound forming nanoparticles with nucleic acids can be designed such that its structure and amphiphilicity changes at endosomal-lysosomal pH (5.0-6.0) and disrupts endosomal-lysosomal membranes, which allows entry of the nanoparticle into the cytoplasm. In one aspect, the ability of specific endosomal-lysosomal membrane disruption of the compounds described herein can be tuned by modifying their pH sensitive amphiphlicity by altering the number and structure of protonatable amines and lipophilic groups. For example, decreasing the number of protonatable amino groups can reduce the amphiphilicity of a nanoparticle produced by the compound at neutral pH. In one aspect, the compounds herein have 1 to 50, 1 to 40, 1 to 30, 1 to 20, 1 to 10, 1 to 8, 1 to 6, 1 to 4, or 2 protonatable amino or substituted amino groups. The pH-sensitive amphiphilicity of the compounds and nanoparticles produced by the compounds can be used to fine-tune the overall pKa of the nanoparticle. Low amphiphilicity of the nanoparticles at physiological pH can minimize non-specific cell membrane disruption and nonspecific tissue uptake of the nucleic acid. In certain aspects, it is desirable that the carriers have low amphiphilicity at the physiological pH and high amphiphilicity at the endosomal-lysosomal pH, which will only cause selective endosomal-lysosomal membrane disruption with the nanoparticles.

The surface of the nanoparticle complexes can be modified by, for example, covalently incorporating polyethylene glycol by reacting unpolymerized free thiol of the nanoparticle to reduce non-specific tissue uptake in vivo. For example, PEG-maleimide reacts rapidly with free thiol groups. The molecular weight of the PEG can vary depending upon the desired amount of hydrophilicity to be imparted on the carrier. PEG-modification of the carrier can also protect nanoparticles composed of the nucleic acid from enzymatic degradation upon uptake by the cell (e.g., endonucleases). Targeting groups, including peptides, proteins, antibodies or antibody fragment, can also be incorporated into the nanoparticle complexes during the preparation of the complexes to enhance the delivery specificity and efficiency of the genetic materials to the target cells. Polyethylene glycol can be used as the spacer to conjugate targeting agents to the nanoparticle complexes.

The compounds described herein can be used to introduce a nucleic acid into a cell. The method generally involves contacting the cell with a complex, wherein the nucleic acid is taken up into the cell. In one aspect, the compounds described herein can facilitate the delivery of DNA or RNA as therapy for genetic disease by supplying deficient or absent gene products to treat any genetic disease or by silencing gene expression. Techniques known in the art can used to measure the efficiency of the compounds described herein to deliver nucleic acids to a cell.

The term "cell" as used herein is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources.

In one aspect, the cell comprises stem cells, committed stem cells, differentiated cells, primary cells, and tumor cells. Examples of stem cells include, but are not limited to, embryonic stem cells, bone marrow stem cells and umbilical cord stem cells. Other examples of cells used in various embodiments include, but are not limited to, osteoblasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, and neurons.

Atypical or abnormal cells, such as tumor cells, can also be used herein. Tumor cells cultured on substrates described herein can provide more accurate representations of the native tumor environment in the body for the assessment of drug treatments. Growth of tumor cells on the substrates described herein can facilitate characterization of biochemical pathways and activities of the tumor, including gene expression, receptor expression, and polypeptide production, in an in vivo-like environment allowing for the development of drugs that specifically target the tumor.

The complexes (i.e., nanoparticles) described above can be administered to a subject using techniques known in the art. For example, pharmaceutical compositions can be prepared with the complexes. It will be appreciated that the actual preferred amounts of the complex in a specified case will vary according to the specific compound being utilized, the particular compositions formulated, the mode of application, and the particular sites and subject being treated. Dosages for a given host can be determined using conventional considerations, e.g., by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

Pharmaceutical compositions described herein can be formulated in any excipient the biological system or entity can tolerate. Examples of such excipients include, but are not limited to, water, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol.

Pharmaceutical carriers are known to those skilled in the art. These most typically would be standard carriers for administration to humans, including solutions, such as sterile water, saline, and buffered solutions at physiological pH.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice. Pharmaceutical compositions can also include one or more active ingredients, such as antimicrobial agents, antiinflammatory agents, anesthetics, and the like.

The pharmaceutical composition can be administered in a number of ways depending on whether local or systemic treatment is desired, and on the area to be treated. Administration can be topically, including ophthalmically, vaginally, rectally, intranasally. Administration can also be intravenously or intraperitoneally. In the case of contacting cells with the nanoparticlar complexes of nucleic acid described herein, it is possible to contact the cells in vivo or ex vivo.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates. It is understood that any given particular aspect of the disclosed compositions and methods can be easily compared to the specific examples and embodiments disclosed herein, including the non-polysaccharide based reagents discussed in the Examples. By performing such a comparison, the relative efficacy of each particular embodiment can be easily determined. Particularly preferred compositions and methods are disclosed in the Examples herein, and it is understood that these compositions and methods, while not necessarily limiting, can be performed with any of the compositions and methods disclosed herein.

The following example is for the purpose of illustration only and is not intended to limit the scope of the claims, which are appended hereto.

Example 1

RNAi-based therapeutic regimens hold tremendous potential for downregulating oncogene expression. However, clinical applications of RNAi have been limited by challenges associated with delivering siRNA, including potential immunogenicity, poor cellular uptake of unmodified siRNA, and degradation by serum nucleases. Nanoparticle-mediated delivery of siRNA is desirable due to its ability to protect siRNAs and facilitate their uptake into target cells. Although various delivery systems are reported to exhibit efficient transfection, concerns regarding their clinical safety and efficacy continue to prevent the advancement of RNAi-based therapeutics. Cationic lipid-based carriers have demonstrated remarkable delivery potential due to their ability to readily form complexes with negatively charged siRNAs, and to efficiently promote cellular uptake of the siRNA cargo. We developed a multifunctional cationic lipid-based carrier, (1-aminoethyl)iminobis[N-oleicylsteinyl-1-aminoethyl)propionamide] (ECO), which facilitates effective siRNA-mediated RNAi in various cancer cell lines. ECO ionically complexes with siRNA and forms stable nanoparticles to protect the siRNA cargo from degradation (FIG. 2A). Once internalized and trafficked to the late endosomes, the pH-sensitive amphiphilicity of ECO promotes endo-lysosomal escape of the nanoparticles, and reduction of the disulfide linkages created during nanoparticle formation by cytosolic glutathione releases the siRNA to achieve potent gene silencing. ECO is also designed to facilitate facile and versatile functionalization of the surface of these nanoparticles with targeting moieties.

Considering the roles of β3 integrin in tumor progression and the urgent need for targeted therapies tailored specifically to TNBC, we sought to alleviate TNBC metastasis by silencing β3 integrin using ECO/siRNA nanoparticles. The present study demonstrates the efficacy of ECO/siβ3 nanoparticles in silencing β3 integrin expression and the consequent inhibition of TGF-β-mediated EMT and invasion of breast cancer cells in vitro. The nanoparticles were modified with RGD peptides via PEG spacers to improve biocompatibility and systemic target-specific delivery of the therapeutic siβ3 in vivo. The efficacy of the RGD-targeted ECO/siβ3 nanoparticles in alleviating primary and metastatic tumor burden was determined in tumor-bearing mice following multiple intravenous injections.

Preparation of ECO/siRNA Nanoparticles

ECO/siRNA nanoparticles were prepared at an N/P ratio of 8. ECO and siRNA were diluted in equal volumes in nuclease-free water from stock solutions of 2.5 mM in ethanol and 18.8 µM in nuclease-free water, respectively. The equal volumes of ECO and siRNA were mixed followed by a 30-min incubation period at room temperature under gentle agitation. For RGD- and RAD-modified ECO/siRNA nanoparticles, RGD-PEG-Mal or RAD-PEG-Mal (MW=3,400 Da; NANOCS, New York, N.Y.) was added into an ECO solution at 2.5 mol % for 30 min under gentle agitation and subsequently mixed with an equal volume of siRNA in RNase-free water for an additional 30 min. After the incubation, free peptide derivative was removed from RGD- and RAD-modified ECO/siRNA nanoparticles by ultrafiltration (Nanosep, MWCO=100 K, 5000×g, 5 min; Sigma Aldrich, St. Louis, Mo.). The following siRNAs were purchased from Integrated DNA Technologies (Coralville, Iowa): Mouse integrin β3 sense: [GCUCAUCUGGAAGCUACUCAU-CACT] (SEQ ID NO: 1), Mouse integrin β3 antisense: [AGUGAUGAGUAGCUUCCAGAUGAGCUC] (SEQ ID NO: 2), Human integrin β3 sense: [GCUCAUCUGGAAA-CUCCUCAUCACC] (SEQ ID NO: 3), and Human integrin β3 antisense: [GGUGAUGAGGAGUUUCCAGAUGAG-CUC] (SEQ ID NO: 4).

Cell Lines and Reagents

MDA-MB-231 cells were obtained from ATCC (Manassas, Va.) and cultured in Dulbecco's Modified Eagle Medium (DMEM; Gibco, Grand Island, N.Y.) supplemented with 10% fetal bovine serum (FBS; Gibco, Grand Island, N.Y.). NME were engineered as previously described[37] and cultured in DMEM supplemented with 10% FBS and 10 µg/mL of insulin. Both cell lines were engineered to stably express firefly luciferase by transfection with pNifty-CMV-luciferase and selection with Zeocin (500 µg/ml; Invitrogen, Carlsbad, Calif.).

Western Blot Analyses

Immunoblotting analyses were performed as previously described. Briefly, NME and MDA-MB-231 cells were seeded into 6-well plates ($1.5 \times 10^5$ cells/well) and allowed to adhere overnight. The cells were then incubated in the absence or presence of TGF-β1 (5 ng/mL) for 3 d and then treated with ECO/siRNA complexes for 4 h in complete growth medium. At each indicated time point, detergent-solubilized whole cell extracts (WCE) were prepared by lysing the cells in Buffer H (50 mM β-glycerophosphate, 1.5 mM EGTA, 1 mM DTT, 0.2 mM sodium orthovanadate, 1 mM benzamidine, 10 mg/mL leupeptin, and 10 mg/mL aprotinin, pH 7.3). The clarified WCE (20 mg/lane) were separated through 10% SDS-PAGE, transferred electrophoretically to nitrocellulose membranes, and immunoblotted with the primary antibodies, anti-β3 integrin (1:1000; Cell Signaling) and anti-β-actin (1:1000; Santa Cruz Biotechnology).

Flow Cytometry for Nanoparticle Cellular Uptake

Cellular uptake and intracellular delivery of ECO/siRNA and RGD-ECO/siRNA nanoparticles was evaluated quantitatively using flow cytometry. ECO/siRNA and RGD-ECO/siRNA nanoparticles were prepared with 40 nM Alexa Fluor 488-labeled siRNA (Qiagen; Valencia, Calif.). Approximately $2.5 \times 10^4$ U87 cells were seeded onto 12-well plates and grown for an additional 24 h. The cells were transfected with ECO/siRNA nanoparticles in 10% serum media. After 4 h, the transfection media was removed and each well was washed twice with PBS. The cells were harvested by treatment with 0.25% trypsin containing 0.26 mM EDTA (Invitrogen; Carlsbad, Calif.), collected by centrifugation at 1,000 rpm for 5 min, resuspended in 500 µL of PBS containing 5% paraformaldehyde, and finally passed through a 35 m cell strainer (BD Biosciences; San Jose, Calif.). Cellular internalization of the nanoparticles was quantified by the fluorescence intensity measurement of Alexa Fluor 488 for a total of $1 \times 10^4$ cells per sample using a BD FACSCalibur flow cytometer. All the experiments were performed in triplicate and the data represent mean fluorescence intensity and standard deviation.

Semi-Quantitative Real-Time PCR Analyses

Real-time PCR studies were performed as described previously. Briefly, NME or MDA-MB-231 cells (100,000 cells/well) were seeded overnight onto 6-well plates and treated with TGF-β (5 ng/mL) for 3 days upon delivery of ECO nanoparticles with a non-specific siRNA or β3 integrin-specific siRNA. At each indicated timepoint, total RNA was isolated using the RNeasy Plus Kit (Qiagen, Valencia, Calif.) and reverse transcribed using the iScript cDNA Synthesis System (Bio-Rad, Hercules, Calif.). Semi-quantitative real-time PCR was conducted using iQ-SYBR Green (Bio-Rad) according to manufacturer's recommendations. In all cases, differences in RNA expression for each individual gene were normalized to their corresponding GAPDH RNA signals.

Invasion and Proliferation Assays

Invasion assays were conducted as described previously. Briefly, NME cells, unstimulated (Pre-) or stimulated with TGF-β for 3 d (Post-EMT), were treated with the ECO/siRNA complexes for an additional 2 d. The cells were then trypsinized and their ability to invade reconstituted basement membranes ($5 \times 10^4$ cells/well) was measured utilizing modified Boyden chambers, as previously described. For the proliferation assay, the NME cells were cultured ($1 \times 10^4$ cells/well) in the presence (post-EMT) or absence (pre-EMT) of TGF-β (5 ng/mL) for 3 d and then treated with ECO/siRNA. Cell proliferation was determined by $^3$H-thymidine incorporation as previously described.

3-Dimensional (3D)-organotypic cultures 3D-organotypic cultures utilizing the "on-top" method were performed as described previously. NME or MDA-MB-231 cells, which were unstimulated (Pre-EMT) or stimulated with TGF-β (5 ng/mL) for 3 d (Post-EMT), were cultured in 96-well, white-walled, clear bottom tissue culture plates (2,000 cells/well) with 50 µL of Cultrex cushions (Trevigen, Gaithersburg, Md.) in media supplemented with 5% Cultrex. The cells were maintained in culture for 4 d with continuous ECO/siRNA treatment every 2 d. Growth was monitored by bright-field microscopy or bioluminescent growth assays (where indicated) using luciferin substrate.

Tumor Growth and Bioluminescent Imaging (BLI)

All the animal studies were performed in accordance with the Institutional Animal Care and Use Committee for Case Western Reserve University. NME cells were engineered to stably express firefly luciferase, and were subsequently injected into the lateral tail vein of female nude mice ($1 \times 10^6$ cells/mouse) after TGF-β stimulation (5 ng/mL) for 7 days. The pulmonary outgrowth was monitored and determined as described previously. MDA-MB-231 cells, also engineered to express firefly luciferase and stimulated with TGF-β for 7 days, were engrafted into the mammary fat pad of female nude mice.

Immunofluorescence and Immunohistochemical Staining

For visualization of the actin cytoskeleton, immunofluorescent analysis was performed as previously described. NME cells ($5 \times 10^4$ cells/well) were plated onto glass-bottom confocal dishes and allowed to adhere overnight, after which they were simultaneously stimulated with TGF-β (5 ng/mL) and treated with ECO/siRNA nanoparticles, either siβ3 or siNS at 100 nM siRNA concentration. After 48 and 72 h of simultaneous TGF-β stimulation and nanoparticle treatment, the cells were washed with PBS, fixed with 4% paraformaldehyde, permeabilized in 0.1% Triton-X 100, stained with Alexa Flour 488 phalloidin (25 µM; Invitrogen; Carlsbad, Calif.), and visualized under a fluorescent confocal microscope.

For immunohistochemistry, primary tumor samples were frozen in OCT, sectioned, fixed in paraffin, and maintained at −80° C. The samples were stained with H&E to evaluate the presence of tumor tissue. For immunofluorescence detection of fibronectin, the paraffin-embedded slides were first deparaffinized using a series of washes in xylene and decreasing concentrations of ethanol. Following heat-induced antigen retrieval, the samples were blocked in TBST solution containing donkey serum and washed three times with TBST. The primary antibody (Abcam; Cambridge, Mass.) was applied for 1 h followed by three rinses with TBST. The Alexa Fluor 488 secondary antibody (Jackson; West Grove, Pa.) was applied for 1 h followed by three washes with TBST and counterstained with DAPI. After washing with TBST and mounting in an anti-fade mounting solution (Molecular Probes), the samples were imaged using a confocal microscope.

Results

ECO/Siβ3 Nanoparticles Induce Sustained Silencing of β Integrin

We examined the ability of ECO/β3 integrin-specific siRNA nanoparticles (ECO/siβ3) to silence β3 integrin expression in mouse NMuMG-EGFR (NME) breast cancer cells, reminiscent of a basal-like breast cancer cell line, and human MDA-MB-231 breast cancer cells, a mesenchymal-like TNBC cell line. The expression of β3 integrin was elevated in both cell lines after stimulation with TGF-β for 72 h. Subsequent treatment of the stimulated cells with ECO/siβ3 nanoparticles resulted in the rapid loss of β3 integrin mRNA within the first 16 h following treatment (FIG. 2B). β3 integrin expression was reduced by ~75% and this downregulation was sustained for up to 7 d in NME cells treated with TGF-β (FIGS. 1B and C). ECO/siβ3 treatment of MDA-MB-231 cells reduced β3 integrin expression level to that of the unstimulated cells (FIGS. 2B and D). Importantly, treatment with ECO/nonspecific siRNA nanoparticles (ECO/siNS) failed to alter β3 integrin expression in both cell lines (FIGS. 2B, C, and D). Collectively, these results demonstrate the ability of ECO/siβ3 nanoparticles to induce efficient and prolonged silencing of β3 integrin expression in breast cancer cells.

Figures 3A, 3B, 3C, 3D, 3E:
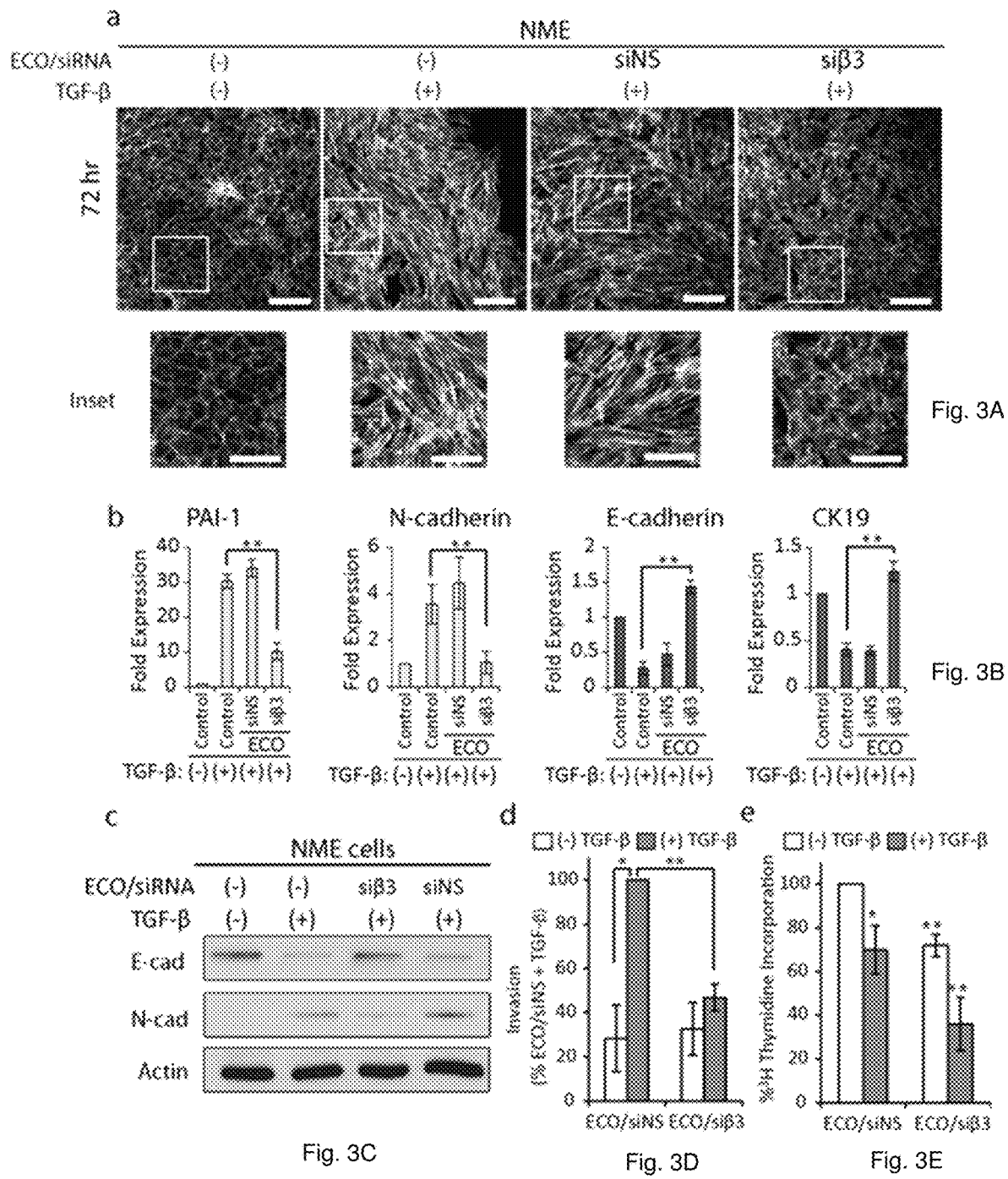
FIGS. 3(A-E) illustrate images, graphs, and an immunoblot showing ECO/siβ3 nanoparticles attenuated TGF-β-mediated EMT, invasion and proliferation. A) Immunofluorescent images of actin cytoskeleton visualized with rhodamine-conjugated phalloidin in mouse NME cells with different treatments (scale bar, 100 m; inset scale bar, 50 m).

ECO/Siβ3 Nanoparticles Attenuate TGF-β-Mediated EMT, Invasion, and Proliferation Next, we investigated the effects of ECO/siβ3 nanoparticles on EMT, invasion, and proliferation of breast cancer cells. Phalloidin staining of the actin cytoskeletal architecture revealed that quiescent NME cells displayed the epithelial hallmark of densely packed and well-organized cortical actin network, while those stimulated with TGF-β exhibited dissolved junctional complexes and acquired an elongated morphology consistent with stress fiber formation that are characteristic of mesenchymal cells (FIG. 3A). Treatment of NME cells with ECO/siβ3 nanoparticles at the time of TGF-β stimulation inhibited dissolution of junctional complexes and stress fiber formation, while treatment with ECO/siNS nanoparticles failed to impact TGF-β-induced morphological changes (FIG. 3A). Moreover, the phenotypic changes in post-EMT cells were accompanied by alterations in the expression of EMT-related genes. Silencing of β3 integrin with ECO/siβ3 nanoparticles significantly reduced TGF-β-mediated upregulation of the mesenchymal markers, N-cad and PAI-1, and inhibited TGF-β-mediated downregulation of the epithelial markers, E-cad and CK-19 (FIGS. 3B and C). ECO/siNS nanoparticles did not alter the effect of TGF-β on the aforementioned EMT markers.

TGF-β-mediated EMT is also associated with increased invasiveness and cell cycle arrest. TGF-β-stimulated NME cells treated with ECO/siNS readily invaded reconstituted basement membrane, while ECO/siβ3 nanoparticles significantly inhibited invasion (FIG. 3D). Conversely, treatment of quiescent NME cells with ECO/siβ3 nanoparticles had no effect on basal invasiveness, an event that is uncoupled from β3 integrin expression. Previous studies demonstrate that parental NMuMG cells readily undergo proliferative arrest when stimulated with TGF-β. We found that EGFR overexpression in the NME cells overrides these cytostatic effects of TGF-β (FIG. 3E), while treatment with ECO/siβ3 partially restores TGF-β-mediated cytostasis (FIG. 3E). Collectively, these findings indicate that ECO/siβ3 nanoparticle-mediated silencing of β3 integrin attenuates TGF-β-induced EMT and invasion, and partially restores TGF-β-mediated cytostasis.

ECO/Siβ3 Nanoparticles Attenuate Outgrowth of Murine and Human MECs in 3D-Organotypic Culture To study the effects of ECO/siβ3 nanoparticles in a physiologically relevant system, we cultured NME and MDA-MB-231 cells in 3D-organotypic cultures to recapitulate the elastic modulus of a distant metastatic site such as the pulmonary microenvironment. This culture method presented additional obstacles in the delivery and uptake of nanoparticles, since these organoids were compact and surrounded by a dense matrix. Using confocal microscopy, we confirmed that ECO/siRNA nanoparticles formulated with fluorescently-labeled siRNA (AF-488) readily gained access to NME organoids by first penetrating into the periphery within 30 min after treatment, and further dispersing throughout the entirety of the organoid to reach a near-uniform distribution within 24 h (FIG. 4A). The dispersion of ECO/siRNA nanoparticles into the inner cell layers of the organoids suggests that ECO/siRNA uptake by these cells may result from diffusion through intercellular spaces or through transcytosis. FIGS. 4B and C show that NME and MDA-MB-231 organoids stimulated with TGF-β exhibited rapid growth as compared to their quiescent counterparts. Treatment with ECO/siβ3 nanoparticles inhibited the growth of both quiescent and TGF-β-stimulated NME and MDA-MB-231 organoids (FIGS. 4B and C) in comparison to treatment with ECO/siNS nanoparticles. These results demonstrate the effectiveness of ECO/siβ3 nanoparticles in attenuating the 3D outgrowth of post-EMT breast cancer cells.

Surface Modification of ECO/siRNA Nanoparticles with RGD Peptide Promotes Cellular Uptake and Sustains Gene Silencing An essential goal of in vivo siRNA delivery is to increase siRNA localization at the disease site while minimizing its accumulation in non-target tissues. We modified ECO/ siRNA nanoparticles with RGD peptides via PEG spacers (3,400 Da), and examined their cellular uptake in both unstimulated and TGF-β-stimulated NME cells. TGF-β stimulation had no effect on the cellular uptake of unmodified ECO/siRNA nanoparticles, while cellular uptake of RGD-ECO/siRNA nanoparticles was robustly enhanced (FIG. 5), leading to effective silencing of β3 integrin in TGF-β-treated cells (FIG. 5). Since αvβ3 is a major receptor that recognizes the RGD targeting peptide, we sought to determine whether β3 integrin silencing impacts cellular uptake of RGD-ECO/siRNA nanoparticles. Although cellular uptake of RGD-targeted nanoparticles was diminished upon β3 integrin silencing, uptake was nonetheless elevated consistently, because of the presence of other receptors for the peptide (FIG. 5). Taken together, these results show that RGD-targeted ECO/siRNA nanoparticles efficiently promote cellular uptake and robust gene silencing, particularly in post-EMT and metastatic breast cancer cells.

RGD-ECO/Siβ3 Nanoparticles Safely Inhibit Pulmonary Outgrowth of Mouse MECs In Vivo To address safety concerns, we examined the acute inflammatory response of intravenously injected PEGylated ECO/siRNA nanoparticles. We examined the acute inflammatory response of intravenously injected PEGylated ECO/siRNA nanoparticles, to address potential safety concerns. Compared to unmodified nanoparticles, PEGylated nanoparticles, which harbor a reduced surface zeta potential, attenuated the elevation of serum interleukin-6 (IL-6) and tumor necrotic factor-α (TNF-α) levels at 4 h post-injection, which were resolved within 24 h. To evaluate the effect of β3 integrin silencing on pulmonary outgrowth, we inoculated TGF-β-treated NME cells into the lateral tail vein of nude mice and subsequently monitored pulmonary outgrowth. Systemic injections of RGD-targeted ECO/siβ3 nanoparticles dramatically inhibited pulmonary outgrowth of post-EMT NME cells, as compared to non-specific RAD-ECO/siβ3 and RGD-ECO/siNS treatment groups. These results demonstrate that PEGylated ECO/siRNA nanoparticles exhibit a good safety profile for systemic siRNA delivery, and that RGD-targeted ECO/siβ3 nanoparticles with PEG spacers can effectively inhibit pulmonary outgrowth of TGF-β-stimulated NME cells, when targeted for in vivo delivery applications.

RGD-ECO/Siβ3 Nanoparticles Effectively Inhibit Primary Tumor Growth and Metastasis of Malignant Human MECs To further evaluate the in vivo effect of our targeted ECO/siβ3 nanoparticles, MDA-MB-231 cells pretreated with TGF-β were engrafted into the mammary fat pad of nude mice. Mice were treated with RGD-ECO/siβ3 (1.5 mg/kg siRNA) every 5 days, starting at day 17. Primary tumor burden was monitored by bioluminescence imaging (BLI) and caliper measurements. Compared to the untreated control, RGD-ECO/siNS or RAD-ECO/siβ3 treatment groups, RGD-ECO/siβ3 treated mice exhibited significantly reduced primary tumor burden (FIG. 6). The primary tumors were resected at week 9 (FIG. 6) and weighed. FIG. 6 shows that RGD-ECO/siβ3 treatment resulted in significantly reduced tumor weights as compared to the control groups. Importantly, the therapeutic efficacy of RGD-ECO/siβ3 was reflected by decreased mRNA expression of β3 integrin in the primary tumors, relative to that in the control groups (FIG. 6). RAD-ECO/siβ3 treatment resulted in marginally reduced β3 integrin expression (FIG. 6), which was consistent with the marginally reduced primary tumor burden, which were not statistically significant (FIG. 6). These data reflect partial uptake of the RAD-ECO/siβ3 nanoparticles by primary tumors as a result of passive tumor accumulation attributed to tumor vascular hyperpermeability. H&E staining of tissue sections demonstrated similar histopathological patterns in RGD-ECO/siβ3-treated and control groups, while untreated mice developed tumors that were more vascularized than RGD-ECO/siβ3-treated tumors. Further immunostaining of tissue sections indicated that RGD-ECO/siβ3-treated primary tumors exhibited decreased expression of the mesenchymal marker, fibronectin (FIG. 6), which is associated with poor overall survival.

RGD-ECO/siβ3 treatment resulted in robust inhibition of tumor metastasis (FIGS. 7A and C) and primary tumor recurrence (FIG. 7B), as compared to control groups at week 12 post-engraftment. Interestingly, RAD-ECO/siβ3 treatment also mediated significant inhibition of tumor metastasis and primary tumor recurrence as compared to RGD-ECO/siNS treatment, but to a lesser extent than RGD-ECO/siβ3. This decrease in the efficacy of RAD-ECO/siβ3 could be attributed to the lack of specific targeting and binding of the nanoparticles to the cancer cells. At 12 weeks post-engraftment, the RGD-ECO/siβ3 group was released from nanoparticle treatment to evaluate the lasting effects of therapeutic β3 integrin silencing on tumor recurrence and metastasis in comparison with the untreated control group. At 4 weeks post-treatment release (16 weeks post-engraftment), the RGD-ECO/siβ3-treated mice remained tumor-free, while the tumor burden of untreated mice continued to increase (FIGS. 7D and E). Finally, throughout the entire course of treatment, no significant difference was observed in the body weights across the different treatment groups, demonstrating the low toxicity of the intravenously administered, targeted PEGylated ECO/siRNA nanoparticles. Collectively, these data highlight the safety and effectiveness of the systemic administration of RGD-ECO/siβ3 nanoparticles for the inhibition of TNBC tumor progression and metastasis.

The data demonstrates that the RGD-ECO/siβ3 nanoparticles constitute an effective targeted therapy to combat TNBC. Cancer metastasis involves a cascade of events, including EMT and local invasion, intravasation, survival in circulation, extravasation, and outgrowth of disseminated cells at the secondary site. In order to alleviate metastasis, it is essential to eliminate post-EMT cells and prevent their metastatic dissemination and outgrowth. Silencing EMT-related genes by RNAi has the potential to revolutionize current treatment standards. β3 integrin has been implicated as a powerful inducer of EMT, potentiating the oncogenic effects of TGF-β by inducing invasion and metastasis of MECs. Although functional disruption of β3 integrin was shown to attenuate TGF-β-mediated EMT and tumor progression, the utilization of β3 integrin siRNA as a therapeutic regimen was previously limited due to the lack of a clinically feasible approach. Here, we highlight how RGD-ECO/siβ3 nanoparticles inhibit TNBC metastasis by silencing the expression of β3 integrin. The inhibition of TGF-β-mediated EMT with ECO/siβ3 nanoparticles was evident by the obstruction of TGF-β-mediated morphological changes, downregulation of epithelial markers, and upregulation of mesenchymal markers. More importantly, the attenuated EMT phenotype, decreased invasiveness resulted in reduced outgrowth of breast cancer cells in 3D-cultures and in vivo, as well as abrogated metastatic dissemination, and subsequently decreased metastatic burden.

Example 2

In this Example, we developed a dual pH-sensitive and peptide-targeted siRNA delivery system. While various attempts have been made to create eIF4E therapies, siRNA-mediated strategies have yet to be employed in vivo. Furthermore, the effect of eIF4E silencing in a drug-resistant TNBC cell line has yet to be established or be translated into a viable systemically-administered therapeutic regimen. The inclusion of the acid-labile hydrazone bond within a peptide-targeted PEG moiety (RGD-PEG(HZ)-ECO/siRNA) created a pH-cleavable coating that sheds from the core ECO/siRNA nanoparticle in response to the acidic endolysosomal environment following uptake into tumor cells. Once the core ECO/siRNA nanoparticle has been re-exposed, the intrinsic pH-sensitive amphiphilicity of ECO/siRNA nanoparticles enables endolysosomal membrane disruption and escape to achieve potent gene silencing. Accordingly, the pH-cleavable nanoparticles will be leveraged to silence eIF4E and resensitize drug-resistant TNBC to paclitaxel therapy.

Materials and Methods

Cell Culture

Human triple-negative breast cancer MDA-MB-231 cells expressing a luciferase reporter enzyme (MDA-MB-231-Luc) were obtained from ATCC (American Type Culture Collection) and cultured in Dulbecco's modified Eagle's media (Invitrogen) and supplemented with 10% fetal bovine serum (Invitrogen), 100 μg/mL streptomycin, and 100 unites/mL penicillin (Invitrogen). The cells were maintained in a humidified incubator at 37° C. and 5% $CO_2$. A paclitaxel-resistant subline of the MDA-MB-231 cell line (MDA-MB-231.DR) was induced by chronic exposure of MDA-MB-231 cells to 5 nM paclitaxel (PTX, Sigma Aldrich) with increasing concentration at each passage over 8 weeks to reach a final concentration of 20 nM. Initially, cells were maintained at 5 nM PTX with increasing concentration in increments of 5 nM after every other passage over 8 weeks to reach a final concentration of 20 nM. Once resistance to paclitaxel was confirmed, the MDA-MB-231.DR cells were maintained at 5 nM PTX.

Synthesis of mPEG(HZ)-Mal and RGD-PEG(HZ)-Mal

NHS-PEG-SH (MW 3400) and mPEG-HZ (MW 5000) were obtained from Nanocs, cRGDfk was obtained from Peptides International.

To synthesize the non-targeted, pH-cleavable PEG spacer, mPEG5000-hydrazide (Laysan Bio) was reacted with N-4-acetylphenyl maleimide (APM). First, 87.8 mg (MW=5000, 1 equivalent, 17.56 μmol) of the hydrazide-derivatized mPEG5000 was dissolved in 10 mL DCM/MeOH (50/50) and 100 mg Na2SO4 was added. Next, 11.7 mg (MW=215.2, 3.1 equivalent, 54.44 μmol) of APM was dissolved in 1 mL DCM/MeOH (50/50) and added dropwise into the mPEG-hydrazide solution. After the addition of APM, acetic acid (1.77 μL of 34% v/v solution in DCM, 0.6 equivalent, 10.54 μmol) was added. The reaction was stirred for 24 hours at room temperature under nitrogen. After 24 hours, the solution was precipitated into cold diethyl ether (3×) to obtain a purified product. The H1 NMR spectrum (Solvent: CDCl3) of mPEG5000(HZ)-maleimide was used to confirm the correct structure using the following characteristic peaks: 8.43 (s, 1H, —NH—), 8.06 (d, 2H, in phenyl), 7.54 (d, 2H, in phenyl), 6.91 (2, 2H, two olefinic protons of maleimide), 3.48-3.58 (m, 438H, PEG).

A three-step reaction was used to synthesize the cRGD-targeted pH-cleavable PEG-hydrazone moiety. First, cRGDfk was first conjugated to the heterobifunctional NHS-PEG3400-SH: 25 mg (MW=603.7, 2 equivalent, 41.4 μmol) of c(RGD)fk was dissolved in 5 mL DMF. Cyclic (RGD)fk was used at 2× molar excess to the NHS-PEG3400-SH. Next, 70.4 mg (MW=3400, 1 equivalent, 20.7 μmol) of NHS-PEG3400-SH was dissolved in 1 mL of DMF and added drop-wise into the c(RGD)fk/DMF solution. After addition, 100 μL of DIPEA was added to the solution. The solution was stirred gently at room temperature for 4 hours. The solution was precipitated into an excess of diethyl ether (3×) to remove excess c(RGD)fk and obtain the purified cRGD-PEG3400-SH product. To ensure free thiol availability, 100 mg of dithiothreitol (DTT) was added to the solution and stirred overnight to reduce any disulfide bonds present in the synthesized cRGD-PEG-SH. Free DTT was removed using a desalting spin column (1.8K MWCO). The product was lyophilized, resuspended in chloroform and stored at −80° C. Conjugation of cRGD to PEG was confirmed by an observed shift of ~600 in the maldi-tof spectrum. To create a hydrazide-activated cRGD-PEG, 25.2 mg (MW≈4000, 1 equivalent, 6.3 mol) of cRGD-PEG-SH was dissolved 5 mL chloroform and reacted with 4.25 mg (N-ε-maleimidocaproic acid) hydrazide (EMCH, MW=225.24, 3 equivalents, 18.9 μmol), 4.39 μL of trimethylamine was added to the reaction (TEA, 5 equivalents, 31.5 μmol). The reaction was carried out for 4 hours at room temperature under stirring. After, the reaction solution was purified using a spin column (1.8K MWCO). The product was lyophilized, resuspended in chloroform and stored at −80° C. For the final step, 12 mg cRGD-PEG(HZ) (1 equivalent, 2.84 mol) was reacted with 1.2 mg N-4-acetylphenyl maleimide (APM, 2 equivalent, 5.68 μmol) overnight at room temperature under constant stirring. The reaction mixture was purified on a silica gel column using chloroform:methanol mobile phase (9:1 v/v). The final product was concentrated and lyophilized. The H1 NMR spectrum (Solvent: DMSO) of cRGD-PEG3400(HZ)-maleimide was used to confirm the structure with the following characteristic peaks: 8.48 (s, 1H, —NH—), 8.0 (d, 2H, in phenyl), 7.6-7.8 (m, cRGD), 7.45 (d, 2H, in phenyl), 7.2 (2, 2H, two olefinic protons of maleimide), 3.1-3.5 (m, 304H, PEG).

Preparation of PEG-Modified ECO/siRNA Nanoparticles

The ECO lipid carrier was synthesized as described previously. ECO (MW=1023) was dissolved in 100% ethanol at a stock concentration of 2.5 mM for in vitro experiments and 50 mM for in vivo experiments. The siRNA was reconstituted in RNase-free water to a concentration of 18.8 μM for in vitro experiments and 25 μM for in vivo experiments. For in vitro experiments, an siRNA transfection concentration of 100 nM was used. ECO/siRNA nanoparticles were prepared at an N/P ratio of 8 by mixing predetermined volumes of ECO and siRNA for a period of 30 minutes in RNase-free water (pH 5.5) at room temperature under gentle agitation to enable complexation between ECO and siRNA. The total volume of water was determined such that the volume ratio of ethanol:water remained fixed at 1:20. For RGD-PEG(HZ)-modified ECO/siRNA nanoparticles, RGD-PEG(HZ)-Mal was first reacted with ECO in RNase-free water at 2.5 mol % for 30 minutes under gentle agitation and subsequently mixed with siRNA in RNase-free water for an additional 30 min. RGD-PEG(HZ)-mal was prepared at a stock solution concentration of 0.32 mM in RNase-free water. Again, the total volume of water was determined such that the volume ratio of ethanol:water remained fixed at 1:20.

Nanoparticle Characterization

The zeta potential of unmodified, mPEG- and mPEG(HZ)-modified ECO/siRNA nanoparticle formulations at different pHs in PBS was determined with a Brookhaven ZetaPALS Particle Size and Zeta Potential Analyzer (Brookhaven Instruments). For each formulation, the nanoparticles were diluted in PBS solutions at pH 7.4, 6.5, or 5.4. The zeta potential measurement was taken at each indicated time point up to 4 hours. Data represents the mean of three independently conducted experiments.

pH-Dependent Membrane Disruption Hemolysis Measurement

The hemolytic activity was measured to determine the membrane-disruptive ability of unmodified, mPEG- and mPEG(HZ)-modified ECO/siRNA nanoparticle formulations at pH levels corresponding to various stages of intracellular trafficking. Red blood cells (RBCs) isolated from rats (Innovative Research Inc.) were diluted 1:50 in PBS solutions at pH 7.4, 6.5, and 5.4. ECO/siRNA nanoparticles were prepared at a volume of 150 µL and incubated with an equal volume of the various RBC solutions in a 96-well plate at 37° C. for 2 hours. Following incubation, samples were centrifuged and the absorbance of the supernatants was determined at 540 nm. Hemolytic activity was calculated relative to the hemolytic activity of 1% Triton X-100 (Sigma Aldrich), a non-ionic surfactant. Each pH was conducted in triplicate and the data presented represents the mean and standard deviation.

Flow Cytometry for Nanoparticle Cellular Uptake Measurements

Cellular uptake and intracellular delivery of various ECO/siRNA nanoparticle formulations include mPEG-maleimide, mPEG(HZ)-maleimide, RGD-PEG-maleimide, RGD-PEG(HZ)-maleimide were evaluated quantitatively with flow cytometry. The ECO/siRNA nanoparticle formulations were prepared with 25 nM AlexaFluor647-labeled siRNA (Qiagen). Approximately $2.5 \times 10^4$ MDA-MB-231 cells were seeded onto 12-well plates and grown for an additional 24 hours. The cells were transfected with each ECO/siRNA nanoparticle formulation in 10% serum media. After 4 hours, the transfection media was removed and each well was washed twice with PBS. The cells were harvested by treatment with 0.25% trypsin containing 0.26 mM EDTA, (Invitrogen) collected by centrifugation at 1000 rpm for 5 min, resuspended in 500 µL of PBS containing 5% paraformaldehyde, and finally passed through a 35 am cell strainer (BD Biosciences). Cellular internalization of ECO/siRNA nanoparticles was quantified by the fluorescence intensity measurement of AlexaFluor 647 fluorescence for a total of 10,000 cells per each sample using a BD FACSCalibur flow cytometer. Each formulation conducted in triplicate and the data presented represents the mean fluorescence intensity and standard deviation.

For studying the endocytic trafficking pathway, the following inhibitors were used 1 hour prior to transfection in MDA-MB-231 cells with the various ECO/siRNA nanoparticles: 4° C., Cytochalasin D (5 µm/mL; Sigma Aldrich), Genistein (200 µM; Sigma Aldrich), and Nocadozole (20 µM; Sigma Aldrich). After 1 hour, the various ECO/siRNA nanoparticles formulated with the fluorescent AF647-labeled siRNA, as described above, were added to the cells. After an additional 2 hours, the cells were harvested and processed as described above. Similarly, cellular internalization of ECO/siRNA nanoparticles was quantified by the fluorescence intensity measurement of AlexaFluor 647 fluorescence for a total of 10,000 cells per each sample using a BD FACSCalibur flow cytometer. Each formulation was conducted in triplicate and the data presented represents the mean fluorescence intensity and standard deviation.

Confocal Microscopy of Nanoparticle Uptake and Intracellular Release of siRNA

Live cell confocal microscopy was used to assess the cellular uptake, endolysosomal escape, and intracellular release of siRNA. Approximately $1 \times 10^5$ MDA-MB-231 cells were seeded onto glass-bottom micro-well dishes. After 24 hours, the cells were stained for 30 minutes each with 5 ag/mL Hoechst 33342 (Invitrogen) and with 50 nM Lysotracker Green DND-26 (Molecular Probes). RGD-PEG- and RGD-PEG(HZ)-modified ECO/siRNA nanoparticles were formed at an N/P ratio of 8 and a 25 nM siRNA concentration with an AlexaFluor 647-labelled siRNA. Images were taken using an Olympus FV1000 confocal microscope while the cells were housed in a humidified weather station under 5% $CO_2$.

In Vitro Luciferase Silencing Efficiency

MDA-MB-231-Luc cells were seeded in 24-well plates at a density of $2 \times 10^4$ cells and allowed to grow for 24 hours. Transfections were carried out in 10% serum media with an N/P ratio of 8 and 100 nM anti-luciferase siRNA concentration (Dharmacon: sense sequence: 5'-CUUACGCUG-AGUACUUCGAdTdT-3' (SEQ ID NO: 5), anti-sense sequence: 5'-UCGAAGUACUCAGCGUAAGdTdT-3' (SEQ ID NO: 6)). Following a 4 hour transfection period, the media was replaced with fresh serum-containing media and the cells continued to grow for up to 72 hours. For experiments using chloroquine (Sigma Aldrich), transfections were conducted in a similar manner either with or without 100 µM chloroquine. As above, following a 4 hour transfection period, the media was replaced with fresh serum-containing media and the cells continued to grow for up to 48 hours. At each time point for luciferase silencing experiments, the cells were rinsed twice with PBS and lysed using the reporter lysis buffered provided in the Promega Luciferase Assay kit. Following lysis, the cells were centrifuged at 10,000 g for 5 minutes and 20 µL cell lysate was transferred to a 96-well plate. To quantify luciferase expression, 100 µL Luciferase Assay Reagent was added to each well and the luminescence was read using a SpectraMax microplate reader (Molecular Devices). Luciferase activity was normalized to the total protein content measured from the cell lysate of each well using the BCA assay (Thermo Scientific). Data was presented relative to the control, which received no siRNA treatment.

In Vivo Luciferase Silencing Efficiency

MDA-MB-231-Luc cells were engrafted into the mammary fat pad of female nude mice ($2 \times 10^6$ cells/mouse). Once the tumors reached an average of 250 $mm^3$, the mice were randomly sorted into 5 groups (n=3): 1) PBS control, 2) PEG-ECO/siLuc, 3) PEG(HZ)-ECO/siLuc, 4) RGD-PEG-ECO/siLuc, 5) RGD-PEG(HZ)-ECO/siLuc. All siRNA nanoparticle variations were formulated at 1.0 mg/kg siRNA in a total injection volume of 150 µL. All mice received a single intravenous tail vein injection of the various nanoparticle formulations following bioluminescent imaging on day 0. Expression of luciferase was quantified using bioluminescence imaging on day 0, 1, 3, 5, and 7. The bioluminescence signal intensity was quantified from a region of interest (ROI) placed over the tumor area. Data was normalized to the average signal intensity of day 0.

Fluorescence Molecular Tomography

Fluorescence imaging of siRNA accumulation within primary MDA-MB-231 mammary fat pad tumors was performed using the FMT 2500 quantitative fluorescence tomography system (Perkin-Elmer). Mice were treated with an intravenous tail vein administration of AlexaFluor 647-conjugated siRNA (1.0 mg/kg) with the various ECO nanoparticle formulations in a total injection volume of 150 µL. The mice were imaged before and after intravenous injection of the nanoparticles at 30 min, 1 h, 2 h, 4 h, 8 h, and 24 h.

Ex Vivo Flow Cytometry and Confocal Microscopy

Mice treated with AF 647-loaded ECO nanoparticles were sacrificed at 48 hours post-injection whereupon the primary tumor was resected and disaggregated into single cell suspensions using mechanical force and disaggregation solution as described previously. The cell suspension was stained with FITC-conjugated mouse MAb against human epithelial antigen (EpCAM) (HEA125; Miltenyi Biotec, Auburn, Calif.) in the dark and on ice for 10 minutes. After staining, the cells were washed and centrifuged, fixed with paraformaldehyde, and finally passed through a 35 m cell strainer (BD Biosciences). Flow cytometry was conducted using the fluorescein channel for HEA-FITC and Cy5 channel for AF647-conjugated siRNA delivered by the ECO nanoparticles for a total of 10,000 cells per each sample using a BD FACSCalibur flow cytometer. Gating within the fluorescein channel was used to identify EpCAM (+) and EpCAM (−) populations. Each formulation was conducted in triplicate and the data presented represents the mean fluorescence intensity and standard deviation. Following flow cytometry, the cell suspensions were examined under an Olympus FV100 confocal microscope.

Semi-Quantitative Real-Time PCR Analyses

Real-time PCR studies were performed as described previously. Briefly, MDA-MB-231 or MDA-MB-231.DR cells (100,000 cells/well) were seeded overnight onto 6-well plates. The cells were then treated with ECO nanoparticles with a non-specific siRNA or eiF4E-specific siRNA (eIF4E: AAGCAAACCUGCGGCUGAUCU (SEQ ID NO: 7)). At each indicated time point, total RNA was isolated using the RNeasy Plus Kit (Qiagen) and reverse transcribed using the iScript cDNA Synthesis System (Bio-Rad). Semi-quantitative real-time PCR was conducted using iQ-SYBR Green (Bio-Rad) according to manufacturer's recommendations. In all cases, differences in RNA expression for each individual gene were normalized to their corresponding GAPDH RNA signals.

Primer Sequences:

```
eIF4E:
Sense
                                  (SEQ ID NO: 8)
5'-CTACTAAGAGCGGCTCCACCAC-3';

Antisense
                                  (SEQ ID NO: 9)
5'-TCGATTGCTTGACGCAGTCTCC-3';

GAPDH
Sense
                                 (SEQ ID NO: 10)
5'-ACGGATTTGGTCGTATTGGGCG-3';

Antisense
                                 (SEQ ID NO: 11)
5'-CTCCTGGAAGATGGTGATGG-3'.
```

Western Blot Analyses

Immunoblotting analyses were performed as previously described. Briefly, MDA-MB-231 and MDA-MB-231.DR cells were seeded into 6-well plates ($1.5 \times 10^5$ cells/well) and allowed to adhere overnight. The cells were then treated with RGD-PEG(HZ)-ECO/siRNA complexes (N/P=8, siRNA concentration of 100 nM) in complete growth medium. After 5 days, detergent-solubilized whole cell extracts (WCE) were prepared by lysing the cells in Buffer H (50 mM β-glycerophosphate, 1.5 mM EGTA, 1 mM DTT, 0.2 mM sodium orthovanadate, 1 mM benzamidine, 10 mg/mL leupeptin, and 10 mg/mL aprotinin, pH 7.3). The clarified WCE (20 mg/lane) were separated through 10% SDS-PAGE, transferred electrophoretically to nitrocellulose membranes, and immunoblotted with the primary antibodies, anti-eIF4E (1:1000; Abcam) and anti-β-actin (1:1000; Santa Cruz Biotechnology).

Cytotoxicity Assay

Cytotoxicity assays were performed in a 96-well plate as described previously, by seeding 2,000 MDA-MB-231 or MDA-MB-231.DR cells/well. First, RGD-PEG(HZ)-modified ECO/siRNA nanoparticles were used to transfect MDA-MB-231 or MDA-MB-231.DR with either siNS or sieIF4E for 48 hours. Next, the wells were washed twice with PBS and incubation with various concentrations of PTX in fresh media. After 2 additional days, the MTT reagent (Invitrogen) was added to the cells for 4 hours followed by the addition of SDS-HCl and further incubation for 4 hours. The absorbance of each well was measured at 570 nm using a SpectraMax spectrophotometer (Molecular Devices). Cellular viability was calculated as the average of the set of triplicates for each PTX concentration and was normalized relative to the no treatment control. Drug resistance was confirmed with an MTT assay to determine the $IC_{50}$ of paclitaxel. The $IC_{50}$ was defined as the dose of drug required to inhibit cell viability by 50%.

In Vivo Tumor Growth Inhibition Study

For in vivo anti-tumor efficacy studies, MDA-MB-231.DR cells ($2 \times 10^6$ cells/mouse) were inoculated in the mammary fat pads of female nu/nu mice. When the tumors reached and average of 150 mm$^3$, the mice were randomly sorted into 4 groups (n=5): 1) PBS control, 2) RGD-PEG(HZ)-ECO/siNS (1.5 mg/kg siRNA)+PTX (5 mg/kg), 3) RGD-PEG(HZ)-ECO/sieIF4E (1.5 mg/kg siRNA)+PTX (5 mg/kg), 4) RGD-PEG(HZ)-ECO/sieIF4E (1.5 mg/kg siRNA). RGD-PEG(HZ)-ECO/siRNA nanoparticles were administered by intravenous injection into the lateral tail vein while PTX was administered in 10% DMSO/PBS with an intraperitoneal injection. Tumor growth was monitored by BLI and tumor size was monitored with caliper measurements. Three days after the final treatment, the mice were sacrificed to harvest tumor tissues.

Bioluminescent Imaging

Longitudinal imaging of the mice was performed using the Xenogen IVIS 100 imaging system. D-luciferin (Xenogen) was dissolved in PBS (15 mg/mL), and 200 μL of the luciferin stock solution (15 mg/mL) was injected i.p. 5 minutes before measuring the light emission. Mice were anesthetized and maintained under 2.5% isoflurane. Bioluminescent signals were quantified using Living Image software (Xenogen) by drawing an ROI over the tumor area.

Immunofluorescence and Immunohistochemical Staining

For immunohistochemistry, primary tumor samples were embedded in optimum cutting temperature (O.C.T.) compound (Tissue-TeK; Torrence, Calif.) in preparation for cryostat sectioning and immediately frozen. The samples were then sectioned, fixed in paraffin, and maintained at −80° C. The samples were stained with H&E to evaluate the presence of tumor tissue. Briefly, the samples were fixed in 10% formalin, rehydrated in 70% ethanol and rinsed in deionized water prior to hematoxylin staining. Samples were then rinsed in tap water, decolorized in acid alcohol, immersed in lithium carbonate and rinsed again in tap water. Next, the eosin counterstain was applied and slides were dehydrated in 100% ethanol, rinsed in Xylene and finally mounted on a coverslip with Biomount.

For immunofluorescence detection of eIF4E (Abcam: ab1126), survivin (Abcam: ab76424), Cyclin D1 (Abcam: ab16663), and VEGF (Abcam: ab46154), the paraffin-embedded slides were first deparaffinized using a series of washes in xylene and decreasing concentrations of ethanol.

Heat-induced antigen retrieval was performed using a pressure cooker in sodium citrate buffer (10 mM Sodium citrate, 0.05% Tween 20, pH 6.0) for 20 minutes. Following heat-induced antigen retrieval, the samples were blocked in TBST solution containing donkey serum and washed three times with TBST. The primary antibody was applied at dilution of 1:100 in blocking solution for 1 h followed by three rinses with TBST. The Alexa Fluor 647 secondary antibody (Abcam: ab150079) was applied at a dilution of 1:1000 in blocking solution for 1 h followed by three washes with TBST and counterstained with DAPI at a dilution of 1:2500 in blocking solution. After washing with TBST and mounting in an anti-fade mounting solution (Molecular Probes), the samples were imaged using a confocal microscope.

Toxicity, Immune Response, and Pathology Studies

Female BALB/c mice (Jackson Laboratories) were used to study the toxicity and immune response of systemic treatment with ECO/siRNA and RGD-PEG(HZ)-ECO/siRNA nanoparticles. Following 1, 3 and 5 injections (n=5 for each amount of injections) spaced 5 days apart, blood was collected at 2 h and 24 h post-injection. Plasma was isolated from blood samples using Microtainer tubes (Becton Dickinson). To measure plasma cytokine levels, TNFα, IL-6, IL1-2, INFγ were quantified by ELISA according to the manufacturer's instructions (Invitrogen).

Statistical Analyses

Statistical values were defined using unpaired Student's t-test, with $p<0.05$ considered to be statistically significant.

Results

Figure 8A:
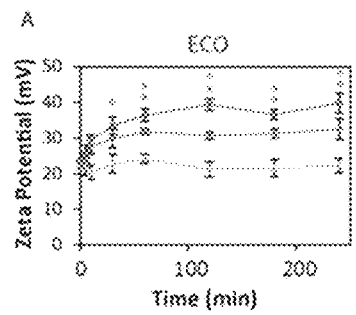
Figure 8B:
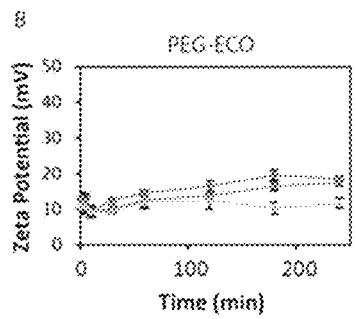

Surface Modification of ECO/siRNA Nanoparticles with pH-Cleavable PEG Layer Restores Intrinsic pH-Sensitive Activity The chemical structure of ECO contains various amino groups such that it carriers a net positive charge at neutral pH. These amine groups electrostatically complex with the siRNA cargo and contribute towards the pH-sensitive amphiphilic characteristic of the delivery system. The amino groups, across a range of pKa's, become protonated in an acidic environment to promote pH-dependent membrane disruption to allow for endolysosomal escape. At an N/P ratio of 8, ECO/siRNA nanoparticles exhibit a zeta potential of 22.3±1.73 mV at neutral pH. With increasing acidity, unmodified ECO/siRNA nanoparticles exhibit a pH-sensitive and time-dependent increase in zeta potential correlating to the protonation of the cationic ethylenediamine head group (FIG. 8A). This protonation is hypothesized to enhance the electrostatic interactions between the ECO carrier and the anionic membrane lipids to promote bilayer destabilization to enable escape into the cytosol. It was observed that modification of the siRNA nanoparticle surface with mPEG3400 at a 2.5 mol % through thiol-maleimide chemistry decreased the overall zeta potential to 12.3±1.39 mV (FIG. 8B). While unmodified ECO/siRNA nanoparticles exhibited pH-sensitivity at pH 6.5 and 5.4, this behavior was attenuated in PEG-modified nanoparticles. After 4 hours of incubation in PBS solutions at pH 6.5 and 5.4, PEGylated ECO/siRNA nanoparticles carried a zeta potential of 17.4±1.1 mV and 18.6±2.9 mV, respectively, compared to 32.5±2.7 mV and 39.8±3.1 mV for unmodified ECO/siRNA nanoparticles. This suggests that the surface aqueous phase formed by PEGylation may impede the protonation of the cationic head group. This was confirmed with the observation that the pH-sensitivity is further diminished towards neutrality by increasing the PEG surface density to 10 mol % (FIG. 9).

Figure 8C:
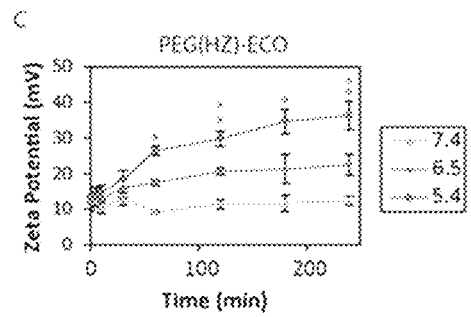

The insertion of the acid-labile hydrazone linkage within the PEG moiety created a pH-cleavable PEG layer to restore the pH-sensitivity of the core ECO/siRNA nanoparticles (FIG. 8C). Hydrazone is a well-characterized linkage known to hydrolyze at pH levels corresponding to the environment of the endolysosomal compartments. The hydrolysis of hydrazone occurs when the —C=N nitrogen is protonated causing a nucleophilic attack of water and the ultimate cleavage of the C—N bond. Previously, the hydrazone linkage has found popularity as a means to conjugate chemotherapeutics, such as doxorubicin, to a wide array of drug delivery systems and prodrugs to enhance intracellular release. This particular hydrazone-modified PEG linkage has also been used previously to create PEG(HZ)-phosphatidylethanolamine conjugates capable of forming micelles. The hydrazone-based micelles were found to be stable at physiological pH but highly sensitive to mildly acidic pHs, resulting in robust degradation of micelles at pH 5.5. Similarly, the observed increase in zeta potential at pH 6.5 and 5.4 presumably corresponds to the acid-catalyzed hydrolysis of the hydrazone linkage and subsequent shedding of the PEG layer whereupon the cationic ECO/siRNA core nanoparticle surface is exposed. Once exposed, the ethylenediamine head group within the ECO/siRNA nanoparticles becomes protonated. At pH 7.4, the zeta potential remains constant at −12 mV indicating that the PEG layer remains intact as a result of the hydrazone linkage stability. Importantly, the stability of surface charge at pH 7.4 suggests the ECO/siRNA nanoparticles will remain PEGylated within the bloodstream at the normal physiological pH. Following exposure to pH 5.4, the hydrazone bond is degraded to remove the PEG layer. In turn, the surface zeta potential of PEG(HZ)-ECO/siRNA nanoparticles gradually increases and after 4 hours is similar to that of the unmodified ECO/siRNA nanoparticles, 36.3±1.9 mV and 39.8±2.8 mV, respectively. However, the time to reach the maximum zeta potential is prolonged, possibly due to the slower kinetics involved with the hydrolysis of the hydrazone linkage.

We have previously shown that the protonation of the cationic head group of ECO is directly coupled with the ability to induce pH-sensitive membrane disruption, a key step for successful and efficient cytosolic delivery of siRNA. To compare the effect of pH-cleavable to non-cleavable PEGylation, we examined the pH-sensitive hemolytic activity of ECO/siRNA nanoparticles modified with both PEGylation strategies (FIG. 9). Non-cleavable PEG-ECO/siRNA nanoparticles had a significantly lowered ability to induce hemolysis at pH 6.5 and 5.4 compared to unmodified ECO/siRNA nanoparticles. Again, this is indicative of the PEG layer inhibiting the interactions with the lipid membrane of the blood cells and also the protonation of the cationic head group of ECO. In alignment, increasing the PEG surface density further inhibited the hemolytic activity of the non-cleavable PEGylated nanoparticles. Conversely, the pH-cleavable PEG(HZ)-ECO/siRNA nanoparticles induced pH-sensitive hemolysis on par with unmodified ECO/siRNA nanoparticles. As the hemolytic activity was evaluated 2 hours following exposure of the red blood cells to the nanoparticles, both formulations of nanoparticles would have reached similar levels of protonation, as observed in FIGS. 8A and C, indicating the cleavage of the hydrazone linkage and subsequent shedding of the PEG layer.

pH-Cleavable RGD-PEG Modification Induces Potent In Vitro Silencing Efficiency

Figure 10A:
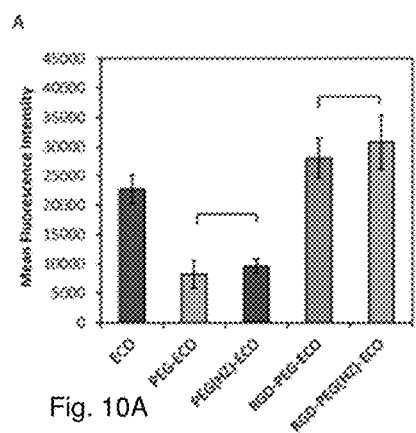

To facilitate ligand-specific uptake of the ECO/siRNA nanoparticles into the target population of cells, a cyclic- RGD (RGD) peptide was conjugated to both pH-cleavable and non-cleavable PEG moieties. Cellular uptake into MDA-MB-231 human breast cancer cells was quantified using flow cytometry with nanoparticles formulated with fluorescently labelled siRNA (FIG. 10A). The inclusion of the hydrazone linkage in both RGD-targeted and non-targeted ECO/siRNA nanoparticles had no significant difference in the ability of the nanoparticles to gain internalization into the cells when compared to the non-cleavable counterparts. Unmodified ECO/siRNA nanoparticles exhibited robust cellular uptake due to strong ionic interactions with the anionic cellular membrane. PEGylation endows neutrality to the nanoparticle surface and impedes such interactions with the cell surface. The addition of the RGD targeting peptide enhanced the cellular uptake and internalization due to specific binding of the RGD peptide to the $\alpha_v\beta3$ integrin known to be present on the cellular surface of the MDA-MB-231 cells.

Surface modification of nanoparticles has been shown to influence the endocytic mechanism through which they are internalized by cells. Further, the endocytic mechanism can dictate the fate of nanoparticles within the intracellular trafficking pathways. By using a series of known pharmacological inhibitors of various endocytic pathways, the primary mechanism of uptake was elucidated for the various formulations of ECO/siRNA nanoparticles in MDA-MB-231 cells: 1) incubation of cells at 4° C. to inhibit energy-dependent endocytic mechanisms, 2) cytochalasin D is generally classified as an inhibitor of macropinicytosis/phagocytosis but recently has been implicated with inhibition of clathrin- and caveolae-mediated pathways, 3) Genistein inhibits caveolae-mediated endocytosis and 4) Nocodazole inhibits clathrin-mediated pathways. PEGylated ECO/siRNA nanoparticles were found to be internalized primarily via clathrin-mediate endocytosis while RGD-targeted nanoparticles entered primarily via caveolae-mediated endocytosis. Interestingly, unmodified ECO/siRNA nanoparticles were found to rely on both energy-dependent and independent mechanisms suggesting that the ECO lipid may be able to directly fuse with the phospholipid membrane of cells. Nanoparticles internalized by Clathrin- and caveolae-dependent mechanisms are often transferred to the lysosomes for degradation, therefore, the ability of both RGD-targeted and non-targeted nanoparticles to escape from the endolysosomal pathway is an important step for achieving gene silencing. No significant difference was observed in endocytic pathways between pH-cleavable and non-cleavable surface modifications.

Figure 10B:
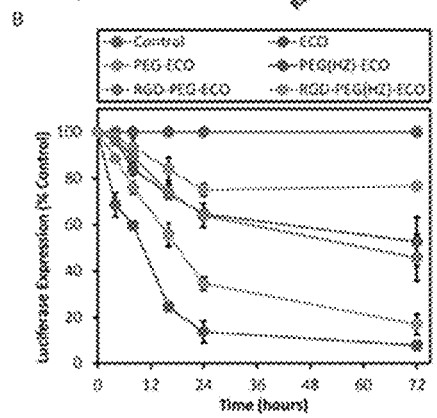

The in vitro luciferase silencing efficacy of the surface modified ECO/siRNA nanoparticles was evaluated in the MDA-MB-231-Luc cell line (FIG. 10B). We have shown that unmodified ECO/siRNA nanoparticles induce potent and sustained gene silencing upwards of 95% due to their ability to readily become internalized, escape from the endolysosomal pathway, and release the cargo siRNA into the cytosol. Accordingly, ECO/siRNA nanoparticles achieved 92.33±2.08% luciferase silencing 72 hours post-treatment in MDA-MB-231-Luc cells. The luciferase silencing efficiency was significantly inhibited upon non-cleavable PEGylation of the nanoparticles (PEG-ECO/siRNA) to only 23.45±1.52% after 72 hours. While decreased cellular uptake contributes to the attenuated silencing efficiency, our hemolysis assay data suggests PEGylation also interferes with the ability of the nanoparticles to escape from the endolysosomal pathway (FIG. 9). Indeed, the silencing efficiency significantly increased to 47.86±10.59% when the pH-cleavable PEG was used when compared to PEG-ECO/siRNA. This observation was highlighted with the addition of the RGD targeting peptide. Non-cleavable RGD-PEG-ECO/siRNA nanoparticles only achieved 54.17±10.01% luciferase silencing while the pH-cleavable RGD-PEG(HZ)-ECO/siRNA formulation reached 83.64±4.58% luciferase silencing 72 hours post-treatment.

Inclusion of Hydrazone Linkage Enhances Endosomal Escape

Figure 10C:
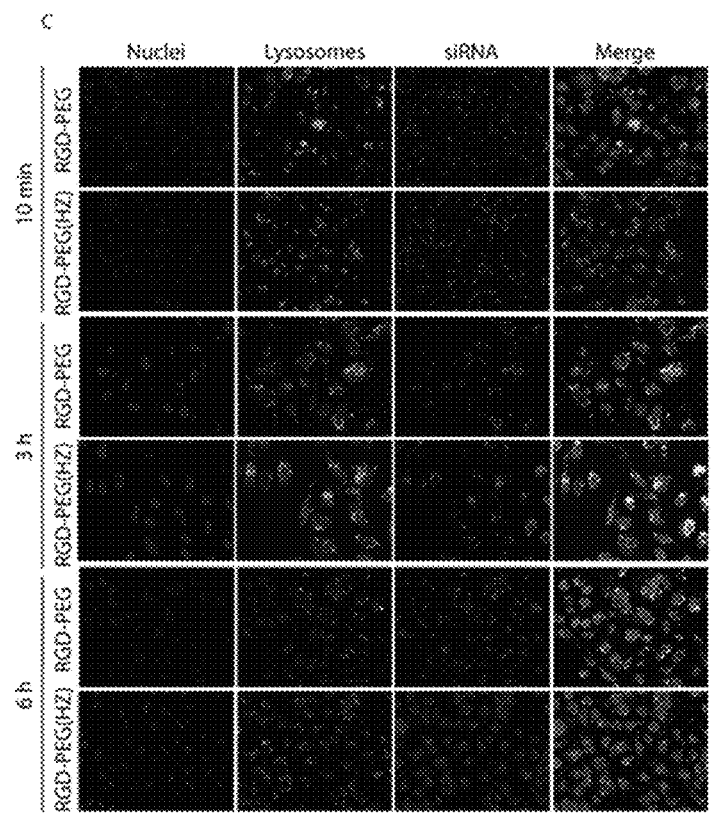

The ability of the hydrazone linkage to enable successful endolysosomal escape was confirmed through live cell confocal imaging (FIG. 10C). MDA-MB-231 cells were transfected with pH-cleavable and non-cleavable RGD-targeted ECO nanoparticles formulated with a fluorescently labelled siRNA while co-stained with Lysotracker (green) to visualize the acidic compartments of the endosomes and lysosome. Images taken after 10 minutes reveal that both RGD-targeted nanoparticle formulations have similar interactions with the cellular membranes. At 3 hours, both formulations exhibit strong co-localization (yellow) with the late endosomes and lysosomes, consistent with the intracellular trafficking of caveolae-mediated endocytosis. However, 6 hours post-treatment, the non-cleavable RGD-targeted nanoparticles appear contained within the endolysosomes as evident by the co-localization of the siRNA and Lysotracker fluorescent signal. In contrast, the pH-cleavable RGD-targeted nanoparticles appear to have successfully escaped from the endolysosomal pathway. Minimal co-localization of the siRNA and Lysotracker signal is observed and the dispersed siRNA signal within the cytosol indicates the siRNA has been released from the nanoparticles, as seen with unmodified ECO/siRNA nanoparticles. The inability of the non-cleavable RGD-targeted nanoparticles to escape into the cytosol further validates the observed discrepancy in gene silencing efficiency when compared with the pH-cleavable counterpart (FIG. 10C).

The endosomolytic agent chloroquine that causes endosome rupture and content release into the cytosol was used to further verify the role the hydrazone linkage plays in promoting escape. For both targeted and non-targeted nanoparticles, the silencing efficiency of pH-cleavable nanoparticles was not affected by chloroquine whereas non-cleavable nanoparticles exhibited a significantly enhanced silencing efficiency. The data suggests that upon treatment with chloroquine, complexes modified with the non-cleavable PEG that were trapped within endolysosomes were then freed into the cytosol while nanoparticles modified with the pH-cleavable PEG moiety had already escaped from the endolysosomes.

Targeted pH-Sensitive Nanoparticles Exhibit Potent and Sustained In Vivo Gene Silencing To study differences in the in vivo gene silencing efficiency of the developed pH-cleavable surface modification strategy, the delivery of anti-luciferase siRNA (1.0 mg/kg) following a single systemic administration was investigated using bioluminescent imaging in a primary mammary fat pad MDA-MB-231 breast cancer tumor model (FIGS. 10A and B). Unlike the in vitro luciferase silencing findings, the non-targeted ECO/siRNA nanoparticles, both pH-cleavable and non-cleavable formulations, had a negligible silencing effect on luciferase expression, suggesting minimal cellular uptake of the siRNA into the tumor cells. In contrast, both RGD-targeted formulations induced luciferase silencing to varying degrees for up to 7 days: the non-cleavable RGD-targeted ECO achieved 52.04% luciferase silencing while the pH-cleavable RGD-targeted formulation achieved 85.17% silencing compared to the no treatment control on day 7. This trend is consistent with the enhancement of silencing efficiency observed in vitro (FIG. 10C).

Figure 11A:
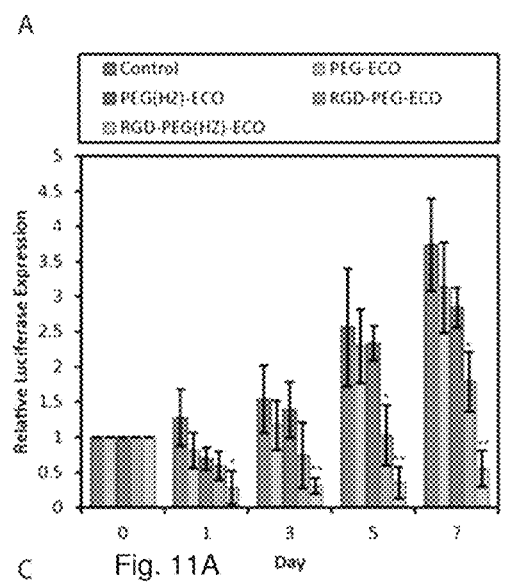
Figure 11B:
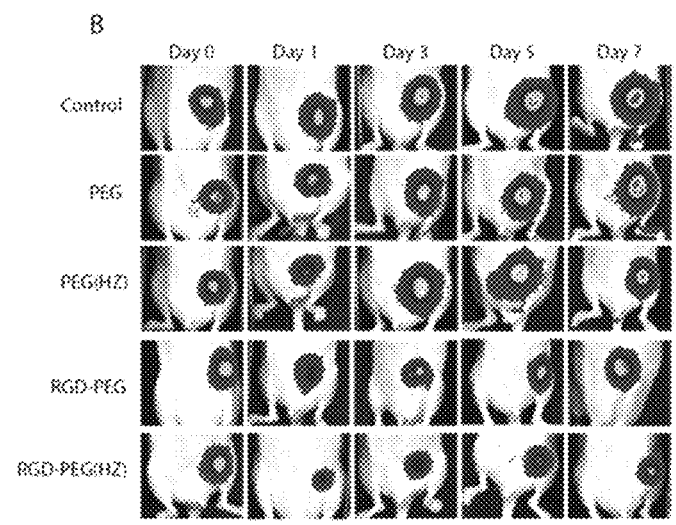
Figure 11C:
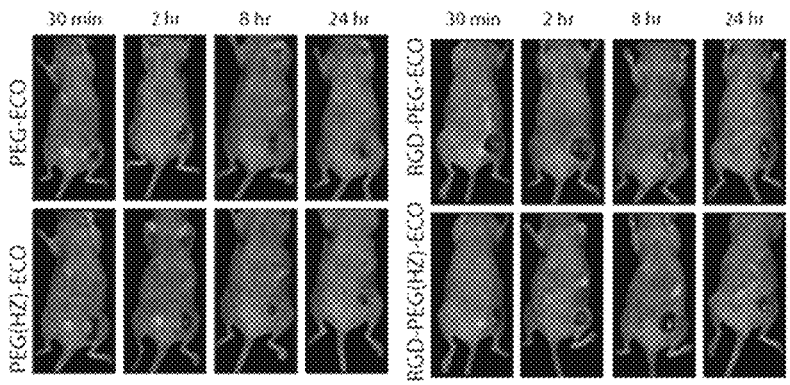
Figure 11D:
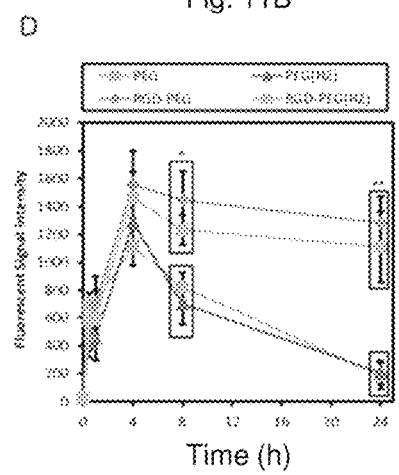

Targeting Ligand Enhances Tumor Retention of Nanoparticles by Promoting Internalization within Tumor Cells The tumor localization and subsequent delivery of functional siRNA following systemic administration of the various siRNA nanoparticle formulations was investigated. Fluorescence molecular tomography (FMT) enabled the analysis of tumor accumulation and retention of the nanoparticle-delivered siRNA over time. Mice received a single systemically administered dose of fluorescently-labeled siRNA (AF 647) delivered by the various surface modified ECO/siRNA nanoparticle formulations. Recent studies have demonstrated that the presence of a targeting ligand does not necessarily impact the initial tumor accumulation of the nanomedicine delivery system, but rather may facilitate tumor cell targeting resulting in longer tumor retention. In alignment, longitudinal FMT imaging studies revealed that the initial tumor localization of siRNA delivered by the targeted and non-targeted nanoparticles was not significantly different for the first 4 hours following systemic administration (FIGS. 11C and D). By 8 hours however, RGD-targeted nanoparticles were observed to accumulate within the tumor to a greater extent than the non-targeted formulations, regardless of whether the PEG modification was pH-cleavable or not. At 24 hours, both RGD-targeted nanoparticle formulations were retained within the tumor while the non-targeted formulations appeared to be washed out, due in part to the inability of the non-targeted nanoparticles to promote cellular internalization, as evident by the minimal presence of siRNA signal from the tumor ROI.

Active targeting of the ECO/siRNA nanoparticles using the RGD peptide may aid in the specific selection of cancer cells within the tumor site and promote internalization of the nanoparticles to a greater extent inside the target cells compared to non-target cells. To evaluate if selective uptake dependent upon cell type occurred, ex vivo flow cytometry was used to quantify siRNA internalization to study differences in cellular uptake of the targeted and non-targeted nanoparticles between human tumor and murine stromal cells. At 48 hours, tumors from the systemically treated mice were excised, disaggregated into single cell suspensions, and stained for the epithelial cellular adhesion molecular (EpCAM) using HEA-FITC to distinguish between the human MDA-MB-231 cancer cells and the murine stromal cells. FACS analysis of the cell suspensions in the FITC channel revealed two distinct cellular populations: EpCAM (+), human cancer cells and EpCAM (−), murine stromal cells. Gating for EpCAM (−) cells in the AlexaFluor 647 channel revealed a minimal shift in fluorescence between both targeted and non-targeted nanoparticle formulations compared to the PBS negative control. A distinct shift was observed in EpCAM (+) cells for targeted nanoparticles compared to both the non-targeted and PBS control groups, suggesting that the RGD-targeted nanoparticles are internalized more efficiently and preferentially by the human cancer cells. Contour plots highlight the two distinct EpCAM (+) and EpCAM (−) cellular populations. While the siRNA signal from non-targeted nanoparticle formulations was evenly distributed throughout both populations, the siRNA signal in EpCAM (+) cells was markedly higher for the RGD-targeted nanoparticle formulations. No difference was observed between pH- and non-cleavable formulations (data not shown).

Following flow cytometry, the cell suspensions were observed under a confocal microscope. Microscopy analysis revealed both pH-cleavable and non-cleavable RGD-targeted nanoparticle formulations were readily internalized by EpCAM (+) cells whereas the non-targeted formulations showed minimal uptake. While the targeted ECO/siRNA nanoparticles did not initially transport the siRNA cargo to the tumor site more efficiently than non-targeted nanoparticles according to the FMT data (FIG. 11D), it appears that RGD peptide enabled cell-specific recognition and internalization of the siRNA. The enhanced cellular uptake correlated to the prolonged retention of fluorescent signal within the tumor ROI as determined by FMT (FIG. 11D) and also the sustained luciferase silencing efficiency of the targeted nanoparticles (FIGS. 11A and B). As internalization of siRNA from pH-cleavable and non-cleavable RGD-targeted nanoparticle formulations appeared similar according to FMT and ex vivo confocal microscopy, the improvement in silencing efficiency of the pH-cleavable formulation may be a direct result of enhanced endolysosomal escape.

A surface modification strategy that combines PEGylation and active targeting not only allows the ECO/siRNA nanoparticles to retain stealth properties during circulation and accumulate at the tumor site by passive targeting, but the PEG shielding moiety provides a tether for versatile incorporation of various active targeting ligands. When further combined with the pH-cleavable hydrazone linkage, the developed surface modification strategy may significantly improve the therapeutic efficacy of the ECO/siRNA nanoparticle delivery system compared to the non-targeted and non-cleavable systems. Taken together with the in vivo luciferase silencing data, the differences in silencing efficiency across all formulations suggest: i) targeted nanoparticles are internalized to a greater extent by the tumor cells and ii) once internalized, formulations with the pH-cleavable PEG modification are more effective in delivering siRNA into the cytosol due to enhanced endolysosomal escape.

Silencing eIF4E by RGD-Targeted pH-Cleavable PEG-Modified ECO/siRNA Nanoparticles Enhances Sensitivity to Paclitaxel in a Drug-Resistance Triple-Negative Breast Cancer Cell Line The ability of the pH-cleavable RGD-PEG(HZ)-ECO/siRNA nanoparticles to mediate knockdown of eIF4E mRNA and protein was next evaluated in vitro. To study the therapeutic consequence of eIF4E downregulation on drug-resistant breast cancer cells, a paclitaxel-resistant subline of the MDA-MB-231 cell line (MDA-MB-231.DR) was induced by chronic exposure of MDA-MB-231 cells to paclitaxel. Interestingly, PTX-resistant cells were found to upregulate eIF4E expression (FIGS. 12A and B). While a widely used chemotherapeutic agent, PTX has been shown to activate signaling pathways that both promote and inhibit cell death. Normally, binding of 4E-BP1 to eIF4E will prevent eIF4E from binding to eIF4G and initiating cap-dependent translation. PTX has been found to diminish the suppressive role of 4E-BP1 through hyperphosphorylation to reduce the association affinity with eIF4E and promote its release. By doing so, eIF4E activity is elevated through a regained association with eIF4G and initiation of translation. Along these lines, treatment of MDA-MB-231 cells with PTX has been demonstrated elsewhere to also increase eIF4E expression in a dose-dependent manner. Importantly, treatment of both cell lines with sieIF4E delivered by targeted and pH-cleavable nanoparticles was able to sustain potent eIF4E mRNA and protein silencing for upwards of 5 days. Nanoparticles delivering a non-specific siRNA induced no significant downregulation of eIF4E expression suggesting that all silencing activity was due to the siRNA and not the ECO carrier.

Figure 12C:
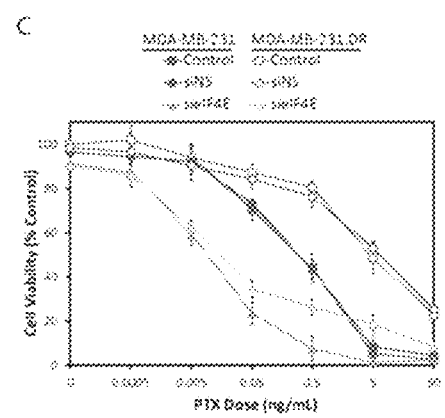

The therapeutic response of eIF4E silencing on enhancing the sensitivity of breast cancer cells to paclitaxel was determined by quantifying the cell viability after a combination of eIF4E silencing by the siRNA nanoparticles followed by treatment with PTX (FIG. 12C). Cells were first treated with RGD-PEG(HZ)-ECO/siRNA nanoparticles for 48 hours followed by treatment with varying concentrations of PTX for an additional 48 hours. For all conditions, cell viability decreased in a PTX concentration-dependent manner. The acquisition of resistance to PTX in the MDA-MB-231.DR subline was evident by a shift in the dose-response curve and the $IC_{50}$. A clear re-sensitization of MDA-MB-231.DR cells to PTX was observed when eIF4E was downregulated using siRNA delivered by RGD-PEG(HZ)-ECO/siRNA nanoparticles. For example, at 0.5 ng/mL PTX, treatment with PTX alone induced 44.6±6.6% viability in MDA-MB-231 cells and 80.7±2.9% viability in the drug-resistant subline. When coupled with silencing of eIF4E, viability dropped to 7.5±5.4% and 26.3±3.6% in MDA-MB-231 and MDA-MB-231.DR, respectively, using the same concentration of PTX.

Figure 13A:
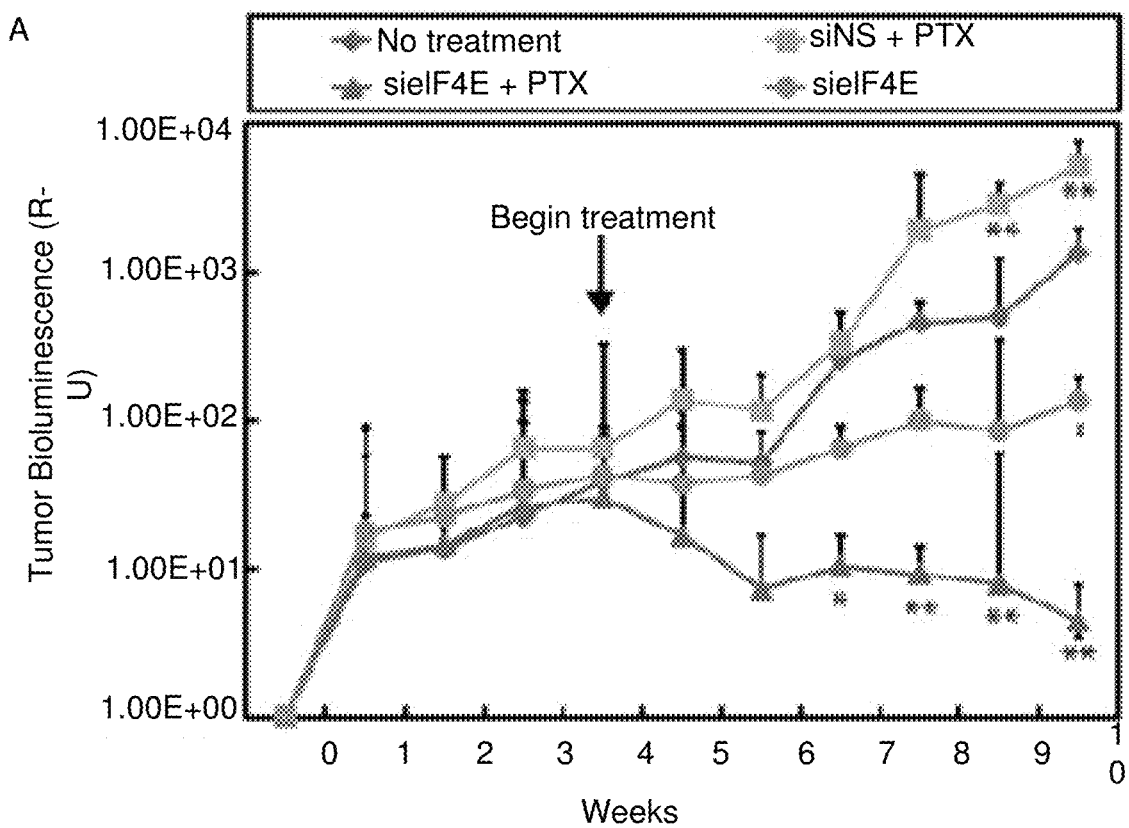
Figure 13B:
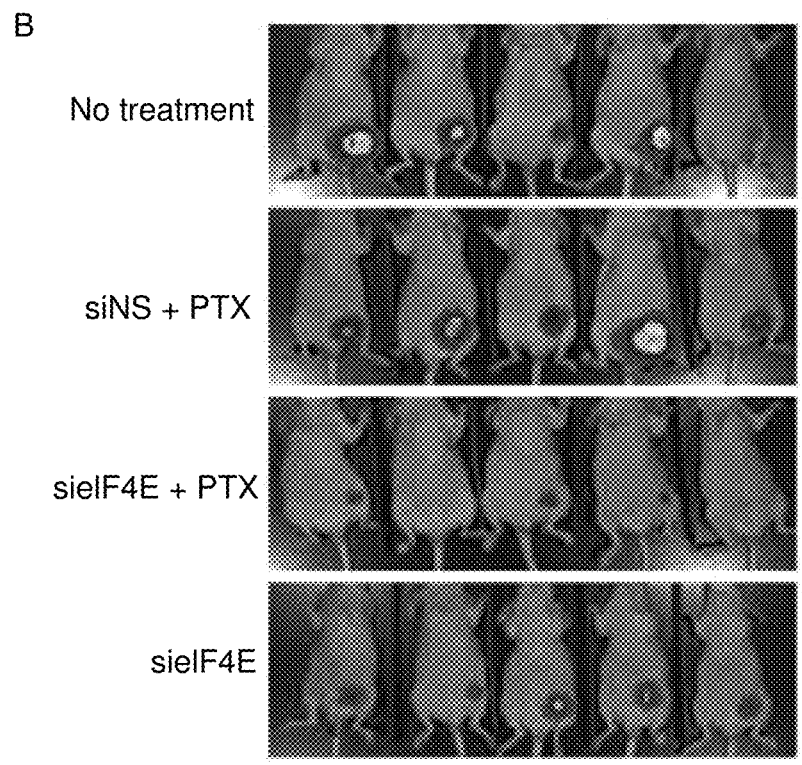
Figure 13C:
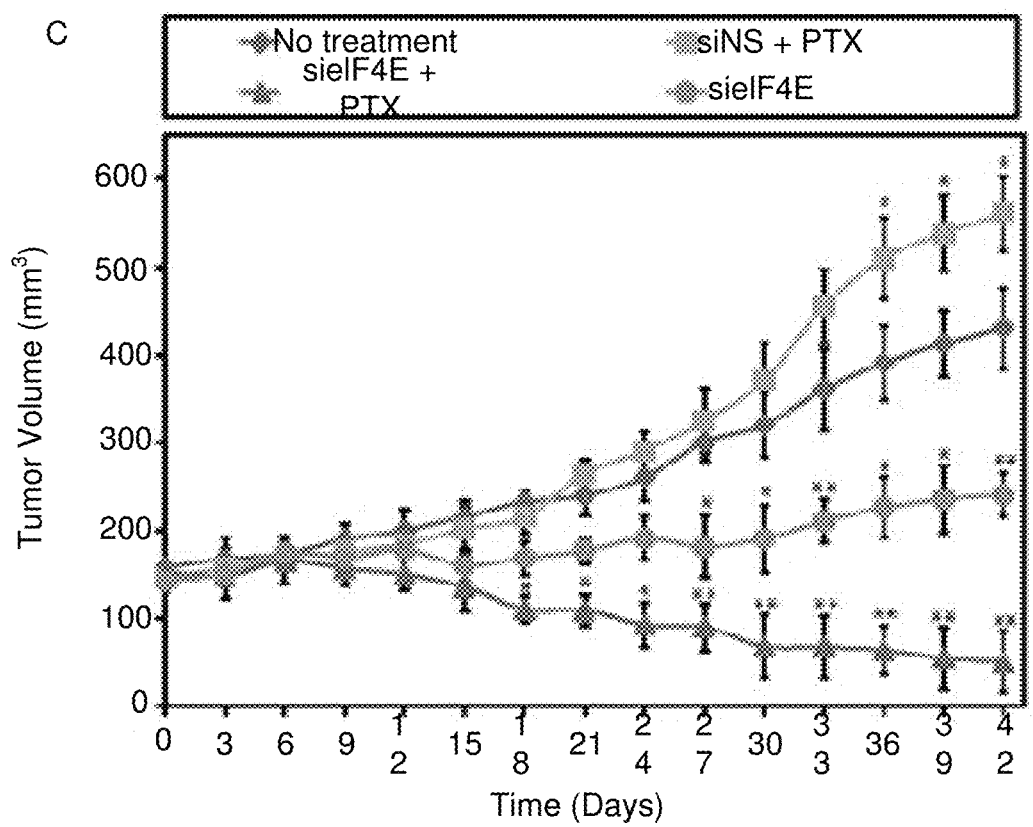
Figure 13D:
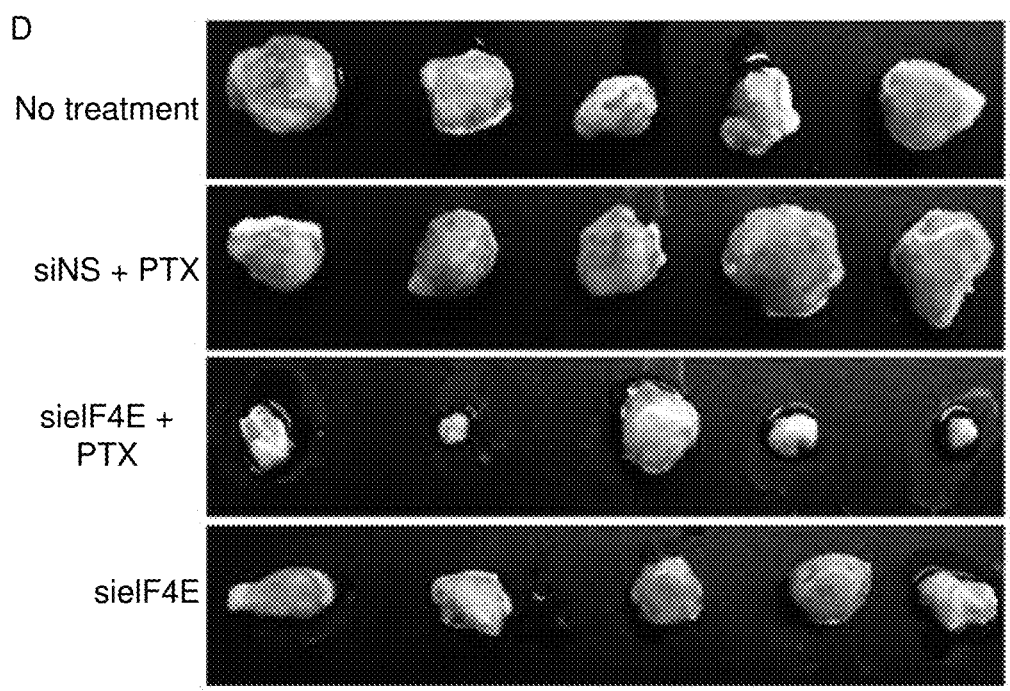
Figure 13E:
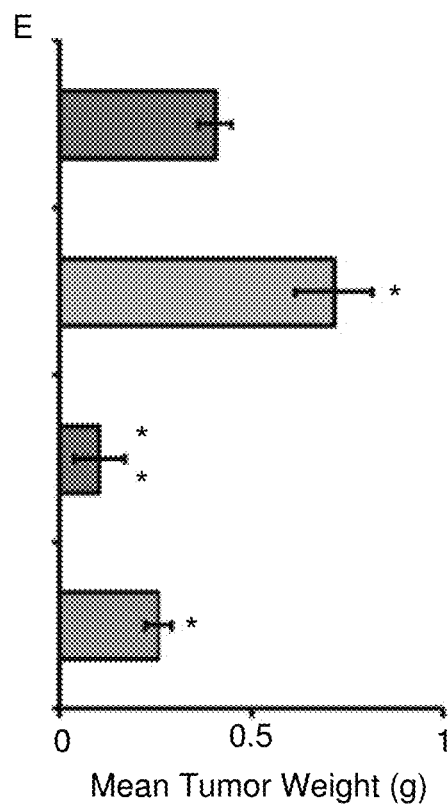
Figure 13F:
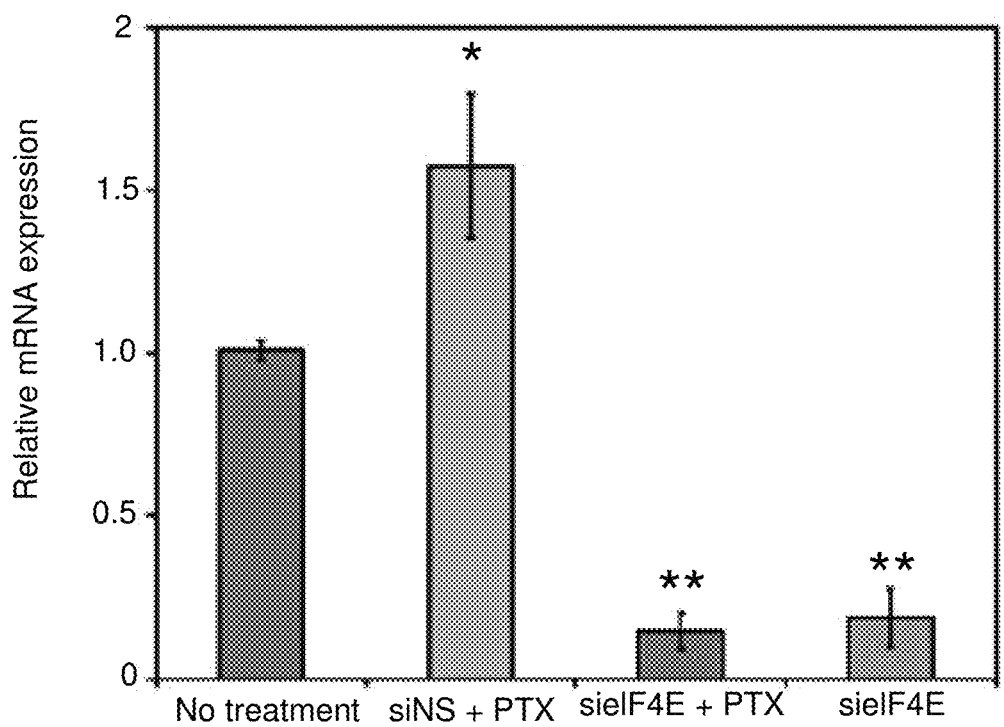

Combination of siRNA Targeting eIF4E and Paclitaxel Inhibits Primary Tumor Growth of Drug-Resistant MDA-MB-231 Cells The ability of the pH-cleavable RGD-PEG(HZ)-modified ECO/siRNA nanoparticles to re-sensitize PTX-resistant MDA-MB-231.DR tumors was evaluated in vivo. Female nude mice were engrafted with MDA-MB-231.DR cells in the mammary fat pad. When the tumors reached approximately 150 mm$^3$ in volume, the mice began receiving alternating treatments with siRNA nanoparticles (1.5 mg/kg siRNA dose) and PTX (5 mg/kg) every 6 days. Treatment with nanoparticles delivering non-specific siRNA (siNS) in combination with PTX had no inhibitory effect on tumor growth. In fact, after several weeks of treatment, the tumors of mice treated with siNS+PTX grew larger and more rapidly compared to the no treatment control, as determined by bioluminescent imaging and tumor volume measurements (FIG. 13A-C). After 42 days of treatment, the no treatment control tumors were an average of 430.1±37.8 mm$^3$ in volume and weighed 404.9±43.6 mg whereas siNS+PTX tumors were 560.3±46.2 mm$^3$ in volume and weighed 715.3±101.5 mg (FIG. 13C-E). Treatment of tumors with nanoparticles delivering anti-eIF4E siRNA alone significantly attenuated tumor growth to 240.4±35.7 mm$^3$ and 256.8±33.5 mg at day 42. This finding is supported by previously established data which demonstrates that silencing of eIF4E induces cell growth arrest. Likewise, Phase I clinical evaluation of the LY2275796 antisense oligonucleotide targeting eIF4E found only cytostasis, and not anti-tumor activity, was achieved upon eIF4E downregulation. A combination of sieIF4E and PTX significantly inhibited tumor growth and lead to tumor regression, 50.2±35.7 mm$^3$ and 103.2±67.4 mg. Significant knockdown of eIF4E mRNA was observed in both groups of mice treated with RGD-PEG(HZ)-ECO/sieIF4E nanoparticles (FIG. 13F).

Interestingly, from Immunofluorescent staining of primary tumor samples, siNS+PTX-treated tumors exhibited elevated levels of eIF4E, survivin, cyclin D1 and VEGF mRNA compared to the no treatment group, suggesting that treatment of drug-resistance cancers with PTX can further drive cancers to become more aggressive (FIG. 13C-E). This may occur through activation of the (PI3K)/akt signaling pathway implicated with both cell survival and drug resistance. As PTX relies upon apoptosis to induce tumor regression, elevated expression of survivin, an antiapoptotic factor, may contribute to the observed resistance to PTX therapy: experimental upregulation of survivin has been shown to confer taxol resistance. A downregulation of survivin exhibited in treatment groups receiving sieIF4E may help suppress tumor growth by increasing the susceptibility of cancer cells to apoptosis, particularly when coupled with PTX therapy. Tumor growth may also be suppressed through a reduction of angiogenesis, a consequence of VEGF downregulation also observed in groups receiving sieIF4E. These data in conjunction with the significant tumor regression observed for the sieIF4E+PTX treatment group indicates that knockdown of eIF4E re-sensitized the MDA-MB-231.DR cells to the cytotoxic effect of PTX.

Chemoresistance is a limitation in the treatment of patients with TNBC, where the lack of effective targeted therapies has left small-molecule based strategies as the sole option. Molecular targets exploited for targeted therapy against drug-resistant TNBCs could contribute significantly to an improved standard of care. While eIF4E has been explored as a therapeutic target in TNBCs before, the presented study represents the first evaluation of eIF4E in a drug-resistance TNBC cell line, therefore adding to the promising body of work surrounding eIF4E.

Long-Term Systemic Administration of RGD-PEG(HZ)-ECO/siRNA Nanoparticles Elicits No Chronic Immune Response or Organ Damage A concern of an RNAi-based approach to eIF4E therapy is the implication of non-specific silencing of eIF4E in healthy tissues. While the inclusion of the RGD-targeting peptide can enhance selective uptake within tumor cells, accumulation of the siRNA nanoparticles in non-specific tissues may lead to eIF4E downregulation outside of the tumor. In the current study, the expression of eIF4E following treatment with the siRNA nanoparticles was not evaluated in other vital organs, however, it has been reported elsewhere that no systemic toxicity was observed when 80% knockdown of eIF4E was achieved in essential organs using antisense technology. This may be explained by the phenomenon known as oncogene addition whereby cancer cells are overly dependent on the expression of a single gene for continued survival and proliferation. Under normal conditions, eIF4E is likely to be inactive due to being bound to the inhibitory 4E-BPs. A reduction in eIF4E levels would therefore have a minimal effect. Cancer cells characterized with elevated eIF4E expression, however, are more dependent on eIF4E expression than non-malignant cells or cancer cells with normal eIF4E expression.

Histopathological examination of liver and kidney tissues from mice receiving the long-term PTX and nanoparticle treatments was performed by hematoxylin and eosin (H&E) staining. No substantial toxicity or tissue damage to the liver or kidney was observed across all treatment groups. The absence of toxicity from treatment groups who received multiple administrations of PTX may be attributed to the relatively low and infrequent dosing: 5 mg/kg every 6 days compared to the conventional dose of 10 mg/kg. Treatment groups who received sieIF4E treatment also revealed no structural damage to the tissues, suggesting any systemic silencing of eIF4E harbors minimal toxicity.

As nude mice bear an inhibited immune system, such animals are not a suitable model to study potential immunogenic responses following systemic administration of ECO/siRNA nanoparticles. Accordingly, immunocompetent BALB/c mice were used to study the possible immune response following repeated tail-vein injections for RGD-PEG(HZ)-modified ECO/siRNA nanoparticles. Blood was collected at 2 h or 24 h following injections following 1, 3 and 5 injections spaced 5 days apart. Systemic treatment with unmodified ECO/siRNA nanoparticles elicited a robust activation of all cytokines measured at both the 2 h and 24 h timepoints due to the high surface charge of the nanoparticles. PEGylation in the form of RGD-PEG(HZ)-modification significantly attenuated the immune response for all tested cytokines. While cytokine levels increased at 2 h for IL-6, IL-12 and IFN-γ, the serum levels were reduced to basal levels at 24 h, indicative of a transient response. Importantly, serum levels were not compounded over the course of 5 repeated injections. These data, in conjunction with pathological examination of the liver and kidneys are indicative of the long-term safety of PEGylated ECO/siRNA nanoparticles.

Example 3

Figure 14A:
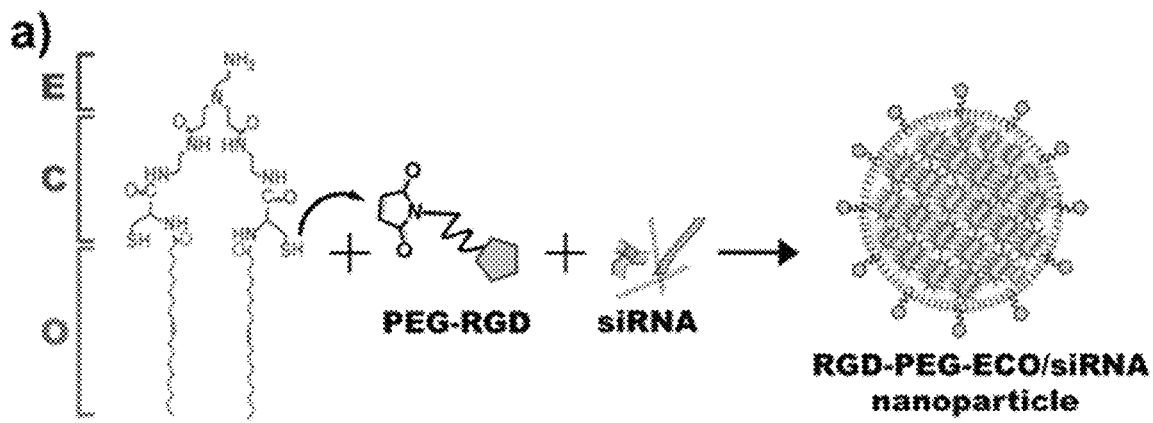
Figure 14B:
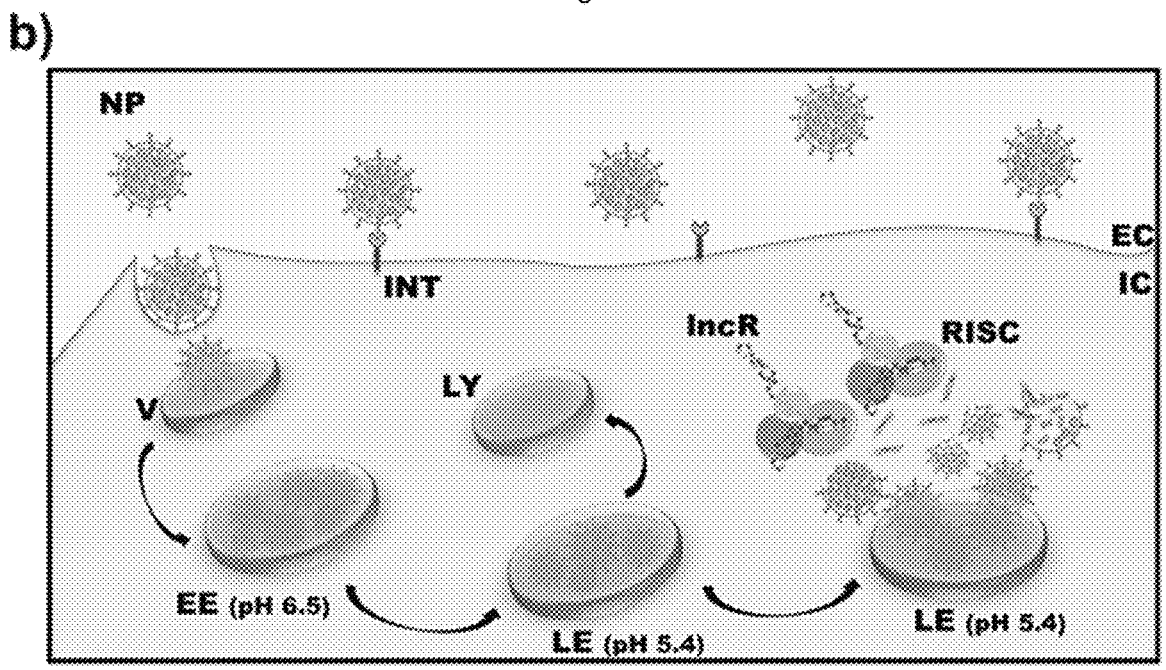

In this Example, we implemented the multifunctional amino lipid carrier ECO, (1-aminoethyl)iminobis[N-oleicyl-cysteinyl-1-aminoethyl)propionamide], which can form stable self-assembly nanoparticles with therapeutic nucleic acids, including siRNA, DNA, and CRISPR/Cas. FIG. 14 illustrates the schematic for the formation and working of the nanoparticle system. ECO undergoes electrostatic complexation with siRNA to form ECO/siRNA nanoparticles that are further stabilized by the hydrophobic condensation of the oleic acid tails and auto-oxidation of cysteine residues to form disulfide bonds. The ECO/siRNA nanoparticles can also be functionalized by conjugation with polyethylene glycol (PEG) for improved biocompatibility and with cyclic RGD peptide for tumor targeting for in vivo gene delivery (FIG. 14*a*). The nanoparticles are known to mediate efficient cytosolic siRNA delivery and robust knockdown of target mRNAs through the PERC mechanism: pH-sensitive amphiphilic endosomal escape, followed by reductive dissociation and cytosolic release of the siRNA cargo, to enable effective RNAi (FIG. 14*b*).

Here, we demonstrate efficient and effective nanoparticle-mediated targeting of the onco-lncRNA DANCR for TNBC therapy. We established the significant overexpression of DANCR in human breast cancer (BCa) cells, tumors, and The Cancer Genome Atlas (TCGA) database. We then investigated DANCR as a therapeutic target for effective TNBC therapy in two cell lines and mouse models by silencing its expression using tumor-targeting RGD-PEG-ECO/siDANCR nanoparticles to facilitate efficient cytosolic delivery of siDANCR. Transfections of RGD-PEG-ECO/siDANCR nanoparticles showed significant and prolonged DANCR silencing and inhibited invasion and proliferation of TNBC cells. Systemic injections of the RGD-PEG-ECO/siDANCR nanoparticles led to suppression of TNBC proliferation in mice with high efficacy and no overt side-effects. We also investigated the mechanism of action of DANCR and observed its pleiotropic roles in regulating multiple cancer-associated signaling pathways in TNBC.

Materials and Methods
Cell Lines and Culture

Normal human mammary epithelial cells (HMECs), hormone receptor positive breast cancer cell lines MCF7 ($ER^+$, $PR^{+/-}$, $Her2^-$) and ZR-75-1 ($ER^+$, $PR^{+/-}$, $Her2^+$), and triple-negative breast cancer cell lines, namely, MDA-MB-231, Hs578T, and BT549 (claudin-low $ER^-$, $PR^-$, $Her2^-$), were purchased from ATCC (Manassas, Va.). HMECs were passaged in Mammary Epithelial Cell Basal Medium supplemented with components of the Mammary Epithelial Cell Growth Kit (Lonza, Allendale, N.J.). MCF7 and ZR-75-1 cells were cultured in Eagle's Minimum Essential Medium (EMEM) supplemented with 10% FBS, 1% Penicillin/Streptomycin and 0.01 mg/mL recombinant human insulin (Sigma, St. Louis, Mo.). MDA-MB-231, Hs578T, and BT549 cells were maintained in Dulbecco's Modified Eagle's Medium (DMEM) supplemented with 10% fetal bovine serum (FBS) and 1% Penicillin/Streptomycin. All the cells were grown at 37° C. and 5% $CO_2$. The cell lines were tested for the absence of *mycoplasma* using the MycoAlert™ *Mycoplasma* Detection Kit (Lonza).

TCGA Analysis

RNA-Seq data from TCGA database for DANCR transcript (ENST00000411630) was mined from the lncRNAtor website. Graphpad Prism was used to perform differential gene expression analysis between 104 normal and 790 breast cancer samples (comprising 80 TNBC, 584 $ER^+$, 508 $PR^+$, 128 $Her2^+$ samples). Graphpad Prism was also used to construct dot plots and heat maps, and perform statistical analyses for the expression data.

cDNA Array

Breast cancer cDNA Array IV (BCRT104) was purchased from Origene Technologies (Rockville, Md.). DANCR expression was quantified by qRT-PCR using SyBr Green PCR Master Mix (Applied Biosystems, CA) and DANCR-specific primers, with 18S primers as controls. Gene expression was analyzed by the $2^{-\Delta\Delta Ct}$ method with 18S expression as the control.

Nanoparticle Formulation and Transfections

ECO-PEG-RGD/siRNA nanoparticles were formulated as previously described. Briefly, the amino lipid ECO (5 mM stock in ethanol) was gently agitated with RGD-PEG-Mal (RGD-PEG/ECO=2.5 mol %) in nuclease-free ultra-pure water for 30 min at RT. This was followed by complexation with siDANCR or siLuc (as negative control NC) at a final siRNA concentration of 100 nM and N/P=10 for an additional 30 min to enable self-assembly formation of ECO-PEG-RGD/siDANCR or ECO-PEG-RGD/NC nanoparticles, respectively. For transfections, the nanoparticle formulation was mixed with culture media and added on to plated cells for 24-48 h, depending on the relevant experiments. The siDANCR duplex [sense 5'-GGU CAU GAG AAA CGU GGA UUA CAdCdC-3' (SEQ ID NO: 12) and antisense 5'-GGU GUA AUC CAC GUU UCU CAU GAC CUC-3' (SEQ ID NO: 13)] was purchased from IDT (Coralville, Iowa). The siLuc duplex [sense 5'-CCU ACG CCG AGU ACU UCG AdTdT-3' (SEQ ID NO: 14) and antisense 5'-dTdT GGA UGC GGC UCA UGA AGC U-3' (SEQ ID NO: 15)] was purchased from Dharmacon (Lafayette, Colo.).

Nanoparticle Characterization

The nanoparticles were diluted in nuclease-free water and characterized for particle size and zeta potential on the LiteSizer™ 500 (Anton Paar), according to manufacturer's instructions. The morphology of the nanoparticles was determined using Transmission electron microscopy (TEM), as described previously. In short, the nanoparticle suspension (20 µL) was pipetted onto a 300-mesh copper grid coated with a thin amorphous carbon film (20 nm). After blotting away excess sample with a filter paper, 3 µL of 2% uranyl acetate solution was added to stain the samples. After two rounds of staining, the samples were dried and imaged via TEM.

RNA Extraction and Analysis

Total RNA was extracted from cells and tissues using the RNeasy Plus Mini Kit (Qiagen, Germantown, Md.), according to manufacturer's instructions. Reverse transcription was performed using the miScript II RT Kit (Qiagen) and qPCR was performed using the SyBr Green PCR Master Mix. Gene expression was analyzed by the $2^{-\Delta\Delta Ct}$ method with 18S expression as the control. The following primer sequences were used—DANCR: Fwd 5'-GCGCCACTATG TAGCGGGTT-3' (SEQ ID NO: 16) and Rev 5'-TCAATGGCTTGTGCCTGTAGTT-3' (SEQ ID NO: 17); 18S: Fwd 5'-TCAAGAAC GAAAGTCGGAGG-3' (SEQ ID NO: 18) and Rev 5'-GGACATCTAAGGGCATCACA-3' (SEQ ID NO: 19); EZH2: Fwd 5'-AGGA CGGCTCCTCTAACCAT-3' (SEQ ID NO: 20) and Rev 5'-CTTGGTGTTGCACTGTGCTT-3' (SEQ ID NO: 21); Survivin: Fwd 5'-ATGGCCGAGGCTGGCTTCATC-3' (SEQ ID NO: 22) and Rev 5'-ACGGCGCACTTTCTTCGCAGTT-3' (SEQ ID NO: 23).

Viability Assay

MTT assay was performed according to manufacturer's protocol (Thermo Fisher Scientific, Waltham, Mass.). Briefly, 5000 cells were plated on 96-well plates. After 24 h, the cells were transfected with therapeutic and negative control nanoparticles. After 48 h, MTT agent (5 mg/mL) was added into the wells and incubated for 4 h. The purple crystals were dissolved in SDS-HCl by incubation for 4 h. The absorbance was measured on SpectraMax microplate reader at 570 nm. Viability of control cells was normalized to 100%, for comparison to treated cells.

BrdU Incorporation Assay

BrdU incorporation was measured using the BrdU Cell Proliferation ELISA Kit from Abcam (Cambridge, Mass.), according to manufacturer's instructions. Briefly, 5000 cells were plated on a 96-well plate for 24 h and then transfected with the nanoparticles. After 40 h, diluted BrdU reagent was added to the cells. After 8 h, the cells were fixed for 30 min and incubated with anti-BrdU antibody for 1 h. After 3 washes, the cells were then incubated with Peroxidase Goat Anti-mouse IgG conjugate for 30 min. Finally, TMB Peroxidase Substrate was added for color development (30 min), followed by the Stop Solution. Absorbance was measured at 450 nm using SpectraMax Microplate reader. Viability of control cells was normalized to 100%, for comparison to treated cells.

Scratch Wound and Transwell Migration Assays

For the scratch wound assay, approximately $5 \times 10^5$ TNBC cells were plated on 6-well plates for 24 h. A single straight scratch was made in the monolayer with a small pipet tip. After washing the detached cells with PBS, the cells were transfected with therapeutic and control nanoparticles and monitored for up to 48 h, or until the scratch wounds were closed. Images were taken using the Moticam T2 camera.

For Transwell migration assays, $1-2 \times 10^5$ cells transfected with nanoparticles were plated on Transwell inserts (VWR, Radnor, Pa.) coated with 0.28 mg/mL Corning™ Matrigel™ Membrane Matrix (Corning, N.Y.). The next day, the unmigrated cells in the inserts were removed by swabbing with Q-tips. The migrated cells were fixed by treating the inserts with 10% formalin for 10 min. After washing with PBS three times, the inserts were placed in 0.05% crystal violet stain for 20 min to stain the migrated cells. The inserts were washed under running water to remove excess stain and set to dry overnight. Images of the purple migrated cells were taken using the Moticam T2 camera. The cells in the images were counted using the ImageJ software.

3D Tumor Spheroid Growth

For the Matrigel growth assay, $3-4 \times 10^5$ TNBC cells were transfected with the nanoparticles, suspended in 5% Matrigel™-containing media and plated on to 24-well plates coated with a thick layer of Corning™ Matrigel™ Membrane Matrix. The ability of the cells to form tumor spheroids in the 3D Matrix was monitored and photographed for up to 7 days using the Moticam T2 camera.

Western Blot

Total cellular protein was extracted. Protein extracts (40 ag) were separated by SDS-PAGE, transferred onto nitrocellulose membrane and immunoblotted with primary antibodies overnight. The following primary antibodies were purchased from Cell Signaling Technology (Danvers, Mass.)-: anti-β-catenin, anti-ZEB 1, anti-N-cadherin, anti-EZH2, anti-SUZ12, anti-me$^3$-H3K7, and anti-survivin. After secondary antibody incubation, the membranes were developed using ChemiDoc™ XRS+ Imager (Biorad, Hercules, Calif.). β-Actin was used as the loading control.

RNA Immunoprecipitation (RIP)

*Magna* RIP kit and DZNep were purchased from Millipore Sigma (Burlington, Mass.). RIP was performed according to manufacturer's instructions. Briefly, cell lysates were incubated with antibody-bead mix overnight at 4° C. Following this, proteins were degraded and the RNA was isolated by the phenol-chloroform extraction method. The RNA was precipitated using Kit components and ethanol at −80° C. overnight. For EZH2 inhibition, cells were treated with 500 µM DZNep for 72 h before harvesting for RIP assay.

Phosphokinase Array

The differential phosphorylation status of 43 different kinases and 2 whole proteins with and without DANCR silencing was detected using the Proteome Profiler Human Phospho-Kinase Array Kit (RnD Systems, Minneapolis, Minn.). MDA-MB-231 and BT549 cells were transfected with RGD-PEG-ECO/NC and RGD-PEG-ECO/siDANCR nanoparticles. After 48 h, the cells were lysed and the lysates were analyzed for the relative phosphorylation profiles, according to the manufacturer's instructions. The expression was quantified by subtracting the background signal from the mean pixel intensity of the duplicate spots and plotted as bar graphs.

Animal Models

Nude athymic mice (6-week-old nu/nu females) were purchased from the Athymic Animal and Preclinical Therapeutic Facility of the Case Comprehensive Cancer Center and housed in the Case Center for Imaging Research at CWRU. All animal experiments were performed according to the protocol and guidelines laid down by the IACUC and ARC of CWRU. For tumor xenografts, $2 \times 10^6$ MDA-MB-231 cells and $4 \times 10^6$ BT549 cells suspended in Matrigel-PBS (6 mg/mL) were injected into the mammary fat pads of each nude mouse. Tumor volumes were monitored and measured once a week using a Vernier caliper. When the average tumor volumes reached 70-90 mm$^3$, mice were randomized into control and treatment groups (n=6 for MDA-MB-231 and n=4 for BT549).

Tumor Xenograft Treatments

For in vivo therapy, nanoparticles were formulated as follows: ECO (50 mM stock) was conjugated to RGD-PEG-Mal (RGD-PEG/ECO=2.5 mol %) for 30 min, followed by complexation with siDANCR or siLuc (siRNA dose=1 mg/kg, [siRNA]=0.3 mg/mL) at N/P=8 for 30 more min, to obtain ECO-PEG-RGD/siDANCR or ECO-PEG-RGD/NC nanoparticles, respectively. The formulations were made in nuclease-free ultra-pure water and injected into the tail vein at siRNA dose of 1.0 mg/kg (100 µL per mouse) once a week for 6 weeks. Tumor volumes and body weights of mice were monitored once a week for 6 weeks. At the end of the experiment, the animals were euthanized, and the tumors and vital organs were harvested for analysis of morphology, histology, and metastasis. Portions of the tissues were fixed in 10% neutral buffered formalin, followed by paraffin embedding, sectioning, and H&E staining. Staining and IHC services were provided by the Tissue Resources Core Facility of CWRU. All the slides were reviewed by a certified pathologist.

Statistical Analyses

All the experiments were independently replicated at least 3 times (n=3), unless otherwise stated. Data are represented as mean±s.e.m. Statistical analysis was performed using Graphpad Prism. Data between two groups was compared using unpaired Student's t-test. Data between three groups was compared using One-way ANOVA. p<0.05 was considered to be statistically significant.

Results

DANCR is Overexpressed in Triple-Negative Breast Cancer (TNBC)

We examined the endogenous levels of DANCR in a wide range of human BCa cells, tumors, and healthy tissues. Using qRT-PCR, we compared the expression of DANCR in BCa cell lines with distinct molecular profiles: hormone receptor (HR)-positive MCF7 and ZR-75, and TNBC Hs578T, BT549, and MDA-MB-231 cells. Compared to normal human mammary epithelial cells (HMECs), the BCa cells showed significantly elevated (4-9 fold) levels of DANCR (FIG. 15a). Among the cancer lines, the TNBC cells (particularly, BT549 and MDA-MB-231) overexpressed DANCR more (2-fold) than the HR-positive cells. Next, we quantified DANCR levels using a cDNA array and found that DANCR is significantly upregulated (40-fold) in TNBC tumors than in normal breast tissues (FIG. 15b). Analysis of the RNA-Seq data from TCGA database for DANCR expression in 104 normal and 790 BCa samples showed consistent results, where DANCR was significantly overexpressed in BCa patients (FIG. 15c), and particularly in TNBC patients (FIG. 15d), compared to healthy controls. The heat map in FIG. 15e shows a diverse range of DANCR expression in the individual normal (N) and TNBC (T) patients, indicating the heterogeneity of the lncRNA. An additional comparison revealed higher DANCR expression in TNBC samples than in the ER$^+$, PR$^+$, and Her2$^+$ tumors (1.34-fold, 1.33-fold, and 1.27-fold, respectively) (FIG. 15f-h). These results demonstrate that DANCR is substantially upregulated in BCa, and especially more so in TNBC.

Targeted RGD-PEG-ECO/siDANCR Nanoparticles Facilitate Robust and Prolonged DANCR Silencing in TNBC Cells To effectively downregulate DANCR expression in TNBC, we formulated stable targeted nanoparticles using the lipid ECO and unmodified siDANCR via self-assembly. The nanoparticles were functionalized with cyclic RGD peptide via a PEG spacer (3,400 Da) for tumor targeting and improved biocompatibility during systemic delivery. These RGD-PEG-ECO/siDANCR nanoparticles mediate efficient cytosolic siRNA delivery and robust knockdown of target mRNAs through the PERC mechanism (FIG. 14). RGD-PEG-ECO/siDANCR nanoparticles were formulated ([siRNA]=100 nM, N/P=10, RGD-PEG/ECO=2.5 mol %,) as previously described. Control RGD-PEG-ECO/NC (NC) nanoparticles were similarly prepared using siLuciferase as the non-specific siRNA (NC). The targeted nanoparticles possessed a narrow size and charge distribution, as characterized by dynamic light scattering (FIG. 16a,b). The RGD-PEG-ECO/NC and RGD-PEG-ECO/siDANCR nanoparticles had a zeta potential of 20±4.6 mV and 24.67±3.6 mV and hydrodynamic diameter of 107.83±19.28 nm and 109.12±6.34 nm, respectively, FIG. 16c. The siRNA loading efficiency and encapsulation in the nanoparticles were evaluated by gel retardation assay, FIG. 16d. Both the nanoparticles demonstrated efficient siRNA encapsulation, with negligible free siRNA bands. The structure and morphology of the nanoparticles were visualized by transmission electron microscopy (FIG. 16e) and consistent sizes (ca. 100 nm) were observed.

The efficiency and kinetics of DANCR silencing by RGD-PEG-ECO/siDANCR nanoparticles were tested in MDA-MB-231 and BT549 cells with high DANCR expression on days 1, 4, and 7 post-treatment. Compared to the control, RGD-PEG-ECO/siDANCR nanoparticles induced 80-90% silencing of DANCR in both the cell lines for at least 7 days after a single transfection (FIG. 16f). These results demonstrate that RGD-PEG-ECO/siDANCR nanoparticles can facilitate efficient, robust, and prolonged silencing of DANCR in TNBC cells.

RGD-PEG-ECO/siDANCR Nanoparticles Suppress the Invasion and Proliferation of TNBC Cells To determine if DANCR depletion plays a role in TNBC suppression, we performed loss-of-function studies in MDA-MB-231 and BT549 cells treated with RGD-PEG-ECO/siDANCR and RGD-PEG-ECO/NC to evaluate functional changes. After confirming ~80% knockdown of DANCR expression after 24 h of siDANCR-nanoparticle treatment (FIG. 17a), the transfected cells were tested for their migratory and invasive capacity. The RGD-PEG-ECO/siDANCR-treated cells showed a significant reduction in their ability to invade Matrigel-coated membranes in standard transwell assays compared to the control-treated cells, evidenced by the reduced number of migrated cells stained using crystal violet (FIG. 17b) and counted using ImageJ (FIG. 17c). The siDANCR-treated cells also showed a significant decrease in their ability to close the wounds scratched into a confluent monolayer, as compared to those treated with the control (FIG. 17d). These results demonstrate that DANCR downregulation inhibits the invasion and migration of TNBC cells.

Next, we determined the effect of RGD-PEG-ECO/siDANCR-mediated DANCR silencing on the survival, growth, and proliferative abilities of MDA-MB-231 and BT549 cells. The cells were treated with the nanoparticles for 48 h, and their viability was measured using the MTT assay. Compared to control, DANCR knockdown caused a significant decrease (30-70%) in the viability of both the cell lines (FIG. 17e), which was further validated by BrdU incorporation assay. RGD-PEG-ECO/siDANCR-treated cells showed significant reduction in BrdU incorporation (FIG. 17f), indicating that DANCR knockdown suppresses the proliferation of TNBC cells.

The effect of RGD-PEG-ECO/siDANCR treatment in MDA-MB-231 and BT549 cells was also assessed in 3D Matrigel culture. Silencing of DANCR significantly reduced the ability of the cells to form 3D tumor spheroids, as compared to control-treated cells (FIG. 17g), at 5 days post-treatment. Finally, the ability of single TNBC cells to grow and proliferate into colonies following DANCR silencing was evaluated by standard clonogenic assay. Control and siDANCR-treated cells were serially-diluted and allowed to grow for 10-15 days. Individual colonies formed were stained with 0.01% crystal violet and counted. As shown in FIG. 17h and FIG. 21, RGD-PEG-ECO/siDANCR-treated cells showed significant reduction of colonies than the NC-treated cells, indicating that loss of DANCR can inhibit the ability of TNBC cells to establish new colonies.

RGD-PEG-ECO/siDANCR Nanoparticles Suppress TNBC Invasion and Proliferation by Influencing Multiple Oncogenic Targets The mechanism of biological functions of DANCR was investigated by evaluating the expression of multiple onco-proteins in MDA-MB-231 and BT549 cells treated with RGD-PEG-ECO/siDANCR or ECO-PEG-RGD/NC. These cell lines represent the claudin-low mesenchymal TNBC subtype, which is particularly aggressive, and is characterized by highly active EMT and Wnt signaling. As shown in FIG. 18a, DANCR silencing downregulated the expression of the Wnt signaling protein 0-catenin, the EMT markers ZEB 1 and N-cadherin, as well as the anti-apoptotic marker survivin. DANCR is known to mediate its effects through EZH2-mediated epigenetic regulation. Since EZH2 is a part of Polycomb repressive complex 2 (PRC2) that facilitates target gene silencing through trimethylation of H3K27 residues, we tested the expression of EZH2 and SUZ12 in siDANCR-treated cells and found a significant decrease in the expression of the two proteins. This was also accompanied by a reduction in the total levels of H3K27-trimethylation (FIG. 18b), suggesting that DANCR may play a role in PRC2-mediated trimethylation and repression of target genes.

Since siDANCR strongly inhibits PRC2 expression, we performed RNA immunoprecipitation (RIP) for EZH2. As shown in FIG. 18c, DANCR directly binds to EZH2 in both MDA-MB-231 and BT549 cells, showing a 12-fold and 8-fold enrichment with anti-EZH2 antibody pull-down, respectively. This enrichment was lost when the cells were treated an EZH2-inhibitor, DZNep. This direct binding coupled with the methylation changes suggests that DANCR influences the expression of its target genes by epigenetic control.

Because lncRNAs are known to play dynamic roles in multiple oncogenic signaling pathways, we evaluated the effect of DANCR silencing on molecular alterations in the TNBC phosphorylation network using a Phospho-kinase array. The functional status of most oncogenes and tumor suppressors is governed by post-translational modifications like phosphorylation, which are widely dysregulated in TNBC. Among these, the phosphorylation status of over 40 kinases expressed in MDA-MB-231 and BT549 cells were analyzed after treatment with RGD-PEG-ECO/siDANCR and RGD-PEG-ECO/NC, FIG. 18d. The kinases that showed a significant change in phosphorylation with siDANCR treatment are highlighted by numbered boxes and depicted in FIG. 18e. A common subset of tumor-promoting kinases, including p38α, ERK1/2, AMPKα1, Src, RSK, FAK, and PRAS40 (#1-7), was significantly less phosphorylated with DANCR silencing in both cell lines.

Interestingly, DANCR knockdown showed a differential phosphorylation pattern between the 2 TNBC cell lines, with reduced phosphorylation of 2 distinct residues of AKT1/2/3 (T308 in MDA-MB-231 vs S473 in BT549 cells, #11), contrasting S133 phosphorylation levels of CREB (#9), phosphorylation of JNK1/2/3 and PDGF-Rβ in MDA-MB-231 (#12,13) only, and phosphorylation of Fyn, Yes, WNK1, and PYK in BT549 (#12-15) only. DANCR silencing reduced the total level of β-catenin (*) in both cell lines, independently validating the results in FIG. 18a, and also altered the phosphorylation patterns of tumor suppressors like p53, $p^{27}$ and transcription factors (TFs) like Stat proteins. The endogenous kinase profiles and the siDANCR-mediated changes in these profiles are distinct between the two cell lines, highlighting the heterogeneity of the disease and broad functions of the lncRNA. Our results underscore the dynamic and complex role of DANCR in impacting multiple oncogenic and tumor suppressor proteins in different TNBC models.

Systemic Administration of RGD-PEG-ECO/siDANCR Nanoparticles Mediates Effective Therapy of TNBC In Vivo The efficacy of RGD-PEG-ECO/siDANCR nanoparticles in treating TNBC was investigated in mice bearing MDA-MB-231 and BT549 xenografts. For the in vivo experiments, RGD-PEG-ECO/siDANCR and RGD-PEG-ECO/NC nanoparticles were formulated at N/P=8, RGD-PEG/ECO=2.5 mol %, and siRNA dose=1.0 mg/kg. Given the higher siRNA concentration, the nanoparticles were larger than those formed for in vitro transfections (FIG. 16), (average diameter 189.46±14.3 nm and 188.11±6.82 nm for RGD-PEG-ECO/NC and RGD-PEG-ECO/siDANCR nanoparticles, respectively) (FIG. 19a). Compared to unmodified ECO/NC and ECO/siDANCR nanoparticles (51.15±2.15 mV and 53.1±1.7 mV), the RGD-PEG-ECO/NC and RGD-PEG-ECO/siDANCR nanoparticles showed a reduction in the zeta potential (29.7±0.6 mV and 40.35±1.65 mV, respectively), indicating proper RGD-PEG conjugation (FIG. 19b). Mice were intravenously injected with RGD-PEG-ECO/NC and RGD-PEG-ECO/siDANCR nanoparticles weekly for 6 weeks. The treatment with RGD-PEG-ECO/siDANCR resulted in a complete suppression of tumor proliferation and reduced tumor volumes (90.3±18.77 to 59.79±18.73 mm$^3$ for MDA-MB-231 and 72.9±14.75 to 58.79±18 mm$^3$ for BT549), while the RGD-PEG-ECO/NC-treated mice showed a rapid tumor growth (91.5±32 to 718±237 mm$^3$ for MDA-MB-231 and 77.77±17.4 to 868.1±238.3 mm$^3$ for BT549), FIG. 19c-e and FIG. 22.

H&E staining of the tumors showed poorly differentiated high-grade malignancy (FIG. 19f). While the NC-treated tumors showed large areas of zonal necrosis, the siDANCR-treated tumor sections showed only focal areas of necrosis. The efficacy of RGD-PEG-ECO/siDANCR was also validated by measuring DANCR expression in total RNA extracted from the primary tumors. Significant downregulation of DANCR was observed in the siDANCR-treated tumors, compared to the NC-treated tumors (FIG. 19g), confirming that RGD-PEG-ECO/siDANCR effectively delivered siDANCR into the cancer cells to mediate efficient DANCR silencing and anti-tumor activity.

As quantified by qRT-PCR, significant reduction of EZH2 (FIG. 19h) and survivin (FIG. 19i) was observed in the siDANCR-treated tumors, suggesting that the tumor suppression and regression are likely due to epigenetic changes and apoptotic/cytostatic effects of systemic siDANCR therapy.

No changes in the body weight were observed in the siDANCR- and NC-treated mice during the entire treatment period (FIG. 20a). The vital organs of the mice were assessed by H&E-staining. As shown in FIG. 20b-d, the liver, kidneys, and lungs showed normal hepatocyte, renal, and alveolar histology, with no evidence of inflammation and fibrosis/interstitial disease, respectively. No significant difference in morphology was observed between the siDANCR- and NC-treated mice, indicating that repeated injections of the nanoparticles did not adversely affect the vital organs and health of the mice.

ECO self-assembles with siRNA to form stable ECO/siRNA nanoparticles, which possess unique features that protect the siRNA cargo during systemic delivery and facilitate pH-sensitive endosomal escape and reductive cytosolic siRNA release (PERC) in target cells. RGD-PEG-ECO/siDANCR nanoparticles mediate robust silencing of DANCR in TNBC cells for at least a week. DANCR knockdown induces apoptotic/cytostatic effects and inhibits invasion, migration, and colony formation, which are important characteristics of tumorigenesis, proliferation, and aggression in TNBC. Consequently, weekly systemic injections of RGD-PEG-ECO/siDANCR nanoparticles at a low dose result in tumor suppression and regression in TNBC models. It can be speculated that the tumor growth arrest or cytostasis may, in part, be due to increased apoptosis, suppression of tumor-promoting proteins, and as yet unidentified epigenetic changes. The therapeutic efficacy of DANCR silencing can be attributed to the diverse gene expression changes we observed in the treated TNBC cells.

Although the overexpression of DANCR has been shown to be associated with poor prognosis and tumor progression in multiple cancers, little is known about the pathways that upregulate DANCR in TNBC. During epidermal and osteoblast development, DANCR is required to maintain the progenitor cells in the undifferentiated state. Since TNBC consists of many poorly differentiated cell types, and a high content of cancer stem cells, it is possible that the maintenance of self-renewal and cancer stemness or the transformation of well-differentiated mammary epithelial cells into the highly aggressive, mesenchymal and poorly differentiated phenotype requires or triggers the overexpression of DANCR. Irrespective of the underlying causes, we demonstrate that DANCR functions pleiotropically at epigenetic, transcriptional, translational, and post-translational levels of gene expression. DANCR silencing results in inhibition of EZH2 and PRC2-mediated H3K27-trimethylation at the epigenetic level; downregulation of TFs β-catenin, ZEB 1, and Stat proteins, and proteins N-cad and survivin; and decreased phosphorylation of Src, FAK, and other oncoproteins. These proteins are upregulated in TNBC; they play critical roles in disease progression, metastasis and drug resistance, and some of them are common targets for developing targeted therapies. Unfortunately, limited curative outcomes have been achieved with these targeted therapies individually. The pleiotropic effects of DANCR silencing with RGD-PEG-ECO/siDANCR may overcome the limitations of conventional approaches of targeting an individual pathway or protein to achieve better therapeutic outcomes. DANCR silencing and the consequent downregulation of the EZH2-SUZ12 axis of the PRC2 complex likely alters the recruitment or binding of EZH2 to its target genes or proteins, in turn impacting the transcriptional silencing of tumor promoters or activation of tumor suppressors. It can be hypothesized that DANCR downregulation enables collective repression of multiple TNBC-promoting pathways, including Wnt and EMT signaling, anti-apoptosis, phosphorylated FAK, Src, RSK1/2/3, AKT1/2/3, and other oncoproteins, resulting in efficacious therapeutic outcome. Thus, it can be speculated that the functional downregulation of a single onco-lncRNA can simultaneously impair several different tumor-promoting pathways, potentially circumventing the problem of compensatory mitogenic pathways arising from drug resistance.

In summary, we demonstrate that DANCR is overexpressed in TNBC and plays pleiotropic roles by regulating multiple molecular pathways. DANCR silencing mediates effective regulation of an array of oncogenic activities and inhibits invasion and proliferation of TNBC cells. Additionally, systemic treatment with targeted nanoparticles results in tumor suppression and regression in two independent TNBC models.

Example 4

BANCR Summary
BANCR Expression in Drug-Resistant Breast Cancer and Prostate Cancer Cells The lncRNA BRAF activated non-coding RNA (BANCR), a 4-exon transcript of 693-bp, was first discovered as an oncogenic long non-coding RNA in $BRAF^{V600E}$ melanomas cells in 2012 and was related to melanoma cell migration. Besides melanoma, increasing evidence has explored the potential role of BANCR in the development and progression of multiple other human malignancies, such as breast cancer and prostate cancer, etc. Here, we checked the expression of BANCR in breast cancer cell line (MCF-7) and its corresponding palbociclib-resistant cell line (MCF-7-DR) and prostate cancer cell line (DU145) and its corresponding paclitaxel-resistant cell line (DU145-DR) by RT-PCR. It was found that both MCF-7-DR and DU145-DR showed upregulated BANCR expression as compared to their parental cells (FIG. 23).

ECO/siBANCR Nanoparticles Facilitate Efficient BANCR Silencing

To effectively downregulate BANCR expression in MCF-7-DR and DU145-DR cells, we formulated stable nanoparticles using the lipid ECO and siBANCR via self-assembly. AllStars Negative Control siRNA (Qiagen) was employed as non-specific siRNA duplex (siNS). The BANCR-specific siRNA duplex (siBANCR, sense: 5'-GCA CAG GAC UCC AUG GCA AUU-3' (SEQ ID NO: 24); antisense: 5'-UUG CCA UGG AGU CCU GUG CUU-3' (SEQ ID NO: 25)) was also purchased from Dharmacon. The particle size and zeta potential distribution of formulated ECO/siRNA were determined by dynamic light scattering (DLS) measurement. Both ECO/siBANCR and ECO/siNS (control) nanoparticles displayed uniform size distribution with an average hydrodynamic diameter of 169 nm and 155 nm (FIG. 24a) and positive zeta potential of 33±0.8 mV and 29±1 mV, respectively (FIG. 24b). For transfection, the plated MCF-7-DR and DU145-DR cells were treated with ECO/siNS or ECO/siBANCR nanoparticles for 24 h. Thereafter, the efficiency of BANCR silencing by ECO/siBANCR nanoparticles were tested in MCF-7-DR and DU145-DR cells with high BANCR expression. Compared to the control, ECO/siBANCR nanoparticles induced significant knockdown of BANCR in both the cell lines (FIG. 24c). These results demonstrate that ECO/siBANCR nanoparticles can facilitate efficient silencing of BANCR.

Example 5

HOTTIP Summary
HOTTIP and HOXA13 Expression in Prostate Cancer (PCa) Cells

The lncRNA HOXA transcript at the distal tip (HOTTIP) located at the 5'-end of the HOXA cluster, which is a key locus control element of HOXA genes, and is brought into close proximity to the 5' HOXA genes by chromosomal looping. HOTTIP has been suggested as a potential prognostic biomarker and therapeutic target for diverse cancers. HOTTIP plays major roles in cell proliferation, EMT, and metastasis, by regulating HOXA13. Here, we firstly checked the expression of HOTTIP and HOXA13 in different PCa cell lines by RT-PCR, DU145 and its corresponding paclitaxel (PTX)-resistant cell line, DU145-DR, PC3 and its corresponding PTX-resistant cell line, PC3-DR, and C4-2. As shown in FIG. 25, it was found that both HOTTIP (FIG. 25a) and HOXA13 (FIG. 25b) were significantly upregulated in PC3 and DU145-DR cells. Interestingly, the expression of HOTTIP and HOXA13 exhibited a high correlation score in PCa cells (Person's r=0.993, FIG. 25c). We also determined the expression level of HOTTIP and HOXA13 in 496 primary tumor tissues samples (data from TCGA). Consistently, the expression of HOTTIP and HOXA13 also had a strongly positive correlation in PCa tissues (Person's r=0.715, FIG. 26).

Considering the high expression of HOTTIP in PC3 and DU145-DR cells, we chose these two cell lines as models to study the role of HOTTIP in PCa cells. According to our previous study, PC3 and DU145-DR cells both exhibit an elongated and spindle-like morphology, which is characteristic of mesenchymal cells (FIG. 27).

ECO/siHOTTIP Nanoparticles Facilitate Efficient HOTTIP Silencing in PCa Cells

To effectively downregulate HOTTIP expression in PCa cells, we formulated stable nanoparticles using the lipid ECO and siHOTTIP via self-assembly. The pH-sensitive lipid ECO was synthesized in our lab. A 5 mM stock solution of ECO (MW: 1023) in ethanol was employed to form nanoparticles with siRNA. The siRNA was dissolved in RNase-free water at a concentration of 25 µM. ECO/siRNA nanoparticles were prepared by mixing the stock solutions of ECO and siRNA at an N/P ratio of 10 in RNase-free water under gentle agitation for about half an hour. The Lincode Non-Targeting Control siRNA #1 (Dharmacon) was employed as non-specific siRNA duplex (siNS). The HOTTIP-specific siRNA duplex (siHOTTIP, sense: 5'-CGG CAG GAG CCC AAG GAA AUU-3' (SEQ ID NO: 26); antisense: 5'-UUU CCU UGG GCU CCU GCC GUU-3' (SEQ ID NO: 27)) was also purchased from Dharmacon. ECO/siRNA nanoparticles have been demonstrated to efficiently mediate cytosolic siRNA delivery and gene silencing through pH-sensitive amphiphilic endosomal escape. The particle size and zeta potential distribution were determined by dynamic light scattering (DLS) measurement. Both ECO/siHOTTIP and ECO/siNS (control) nanoparticles displayed uniform size distribution with an average hydrodynamic diameter of 111 nm and 95 nm (FIG. 28a) and positive zeta potential of 32±1 mV and 45±1 mV, respectively (FIG. 28b). The ability of ECO to entrap siRNA was evaluated by gel electrophoresis. ECO/siRNA nanoparticle solution (7 µL) mixed with 3 µL of loading dye was loaded into a 1% agarose gel. Free siRNA was also loaded as control. After electrophoresis at 100 V for 20 min, the gel was imaged using a ChemiDoc XRS+ System to visualize the encapsulated and free siRNA bands. The gel retardation assay demonstrated efficient encapsulation of siRNA in the nanoparticles, with negligible free siRNA bands (FIG. 28c). These results indicate that stable ECO/siRNA nanoparticle formulations with a robust entrapment of negatively charged siRNA were achieved.

For transfection, the plated PC3 and DU145-DR cells were treated with ECO/siNS or ECO/siHOTTIP nanoparticles for 24 h. Thereafter, the efficiency of HOTTIP silencing by ECO/siHOTTIP nanoparticles were tested in PC3 and DU145-DR cells with high HOTTIP expression. Compared to the control, ECO/siHOTTIP nanoparticles induced significant knockdown of HOTTIP in both the cell lines (FIG. 28d). These results demonstrate that ECO/siHOTTIP nanoparticles can facilitate efficient silencing of HOTTIP in PCa cells.

ECO/siHOTTIP Inhibits Proliferation of PCa Cells

In order to study the effect of ECO/siHOTTIP in proliferation of PCa cells. We performed a cell viability assay using CCK-8. PCa cells (untreated, UT) or PCa cells transfected with ECO/siRNA nanoparticles (siNS or siHOTTIP) were seeded onto a 96-well plate at a density of 5,000 cells/well and incubated overnight to allow adherence. CCK-8 assay was performed at day 1, 2 and 3 after seeding according to manufacturer's protocol. Briefly, CCK-8 with a 10% vol. of the medium was added into each well. After 1 h incubation at 37° C., the absorbance (O.D.) of the solution at 450 nm was measured using a microplate reader. The O.D. values were normalized to the blank. The experiments were carried out in quadruplicate.

As shown in FIG. 29, compared to untreated group and siNS control, HOTTIP knockdown caused a significant decrease in the viability of both the cell lines at day 1 to day 3, indicating that HOTTIP knockdown suppresses the proliferation of PCa cells.

This was further validated by live/dead staining using calcein-AM (Dojindo) and propidiumiodide (PI). Approximately 1,000,000 PCa cells (untreated, UT) or PCa cells transfected with ECO/siRNA nanoparticles (siNS or siHOTTIP were seeded onto a 6-well plate for 24 h. At day 3 after seeding, the cells were washed by pre-warmed PBS and stained with 2 µM calcien-AM for live cells (in green fluorescence) and 4 µM PI for dead cells (in red fluorescence) for 15 min at 37° C. Thereafter, the samples were imaged under a confocal microscope. As shown in FIG. 30, compared to untreated group and siNS control, HOTTIP knockdown caused a significant increase in the number of dead cells (in red fluorescence). Moreover, the effect of silencing HOTTIP by ECO/siHOTTIP nanoparticles on cell viability were dose dependent. As increase in the dose of siHOTTIP, the cell viability significantly decreased compared to the siNS control in PC3 cells (FIG. 31).

3D tumor spheroid growth assay, a cell culture technique that provides a more physiological model to mimic in vivo tumor conditions was performed. Transfected PCa cells (300,000) were suspended in 5% Matrigel-containing media and plated on to 24-well plates coated with a thick layer of Corning™ Matrigel™ Membrane Matrix. The ability of the cells to form tumor spheroids in the 3D Matrix was monitored and photographed at day 7 using the Moticam T2 camera. Silencing of HOTTIP significantly reduced the ability of the cells to form 3D tumor spheroids, as compared to siNS control-treated cells (FIG. 32), at 7 days' post-treatment. Taken together, these results indicate that silencing HOTTIP by ECO/siRNA nanoparticles can inhibit proliferation and 3D tumor spheroid growth of PCa cells (PC3 and DU145-DR).

ECO/siHOTTIP Inhibits Invasion, Migration and Epithelial-Mesenchymal Transition (EMT) of PCa Cells The transfected cells were tested for their migratory and invasive capacity by scratch wound closure assay and transwell cell migration and invasion assay. For scratch wound closure assay, approximately 1,000,000 PCa cells transfected with ECO/siRNA nanoparticles were seeded onto a 6-well plate for 24 h. A sterilized 200 µL pipette tip was used to press firmly against the top of the plate and make a vertical wound down through the cell monolayer. After aspirating the media and cell debris, fresh media was added slowly to avoid detaching additional cells. An initial 0 h picture was taken using Moticam and wound closure was monitored for up to 24 h post-scratch. The siHOTTIP-treated cells also showed a significant decrease in their ability to close the wounds scratched into a confluent monolayer, as compared to those treated with the control (FIG. 33).

For transwell cell migration and invasion assay, PCa cells transfected with ECO/siRNA nanoparticles were seeded onto Transwell inserts coated with (for invasion) or without (for migration) 0.28 mg/mL Corning™ Matrigel™ Membrane Matrix (Corning, USA). After 24 h, cotton-tipped applicators were used to remove the gel and/or remaining cells that have not migrated from the top of the inserts. Then, the inserts were fixed with 3.7% formalin for 10 min and immersed in 0.1% crystal violet for 20 min to stain the migrated cells. Images of the stained inserts were taken using Moticam. ECO/siHOTTIP treated PC3 and DU145-DR cells showed a significant reduction in their ability of migration and invasion, evidenced by the significantly reduced number of migrated cells stained in purple compared with those treated with ECO/siNS (FIG. 34).

In addition to functional changes, silencing of HOTTIP with ECO/siHOTTIP nanoparticles also resulted in changes in molecular signatures of PC3 and DU145-DR cells. Reduced expression of the mesenchymal markers, ZEB-1, N-cadherin, β-Catenin and vimentin, was observed in the western blots of ECO/siHOTTIP treated cells (FIG. 35). Taken together, these results indicate that silencing HOTTIP by ECO/siRNA nanoparticles can inhibit invasion, migration and EMT of PCa cells (PC3 and DU145-DR).

Role of HOTTIP in TGF-β1 Treated DU145 Cells

In order to confirm the role of HOTTIP in PCa cells with mesenchymal feature, DU145 cells, which display the epithelial hallmark of densely packed squamous morphology and express lower level of HOTTIP, were treated with 5 ng/mL TGF-β1. After treated with TGF-β1, DU145-TGFβ1 cells exhibited mesenchymal hallmark of elongated and spindle-like morphology. Furthermore, significant upregulation of mesenchymal markers, N-cadherin, and downregulation of epithelial marker, E-cadherin was observed for the DU145-TGF-β1 cells as compared to DU-145 cells. Interestingly, expression of HOTTIP was also upregulated after treatment with TGF-β1 (FIG. 36).

Next, we determined the effect of ECO/siHOTTIP-mediated HOTTIP silencing on the migration and invasion capacity of DU145-TGF-β1 cells using Transwell study. Similar to the result of PC3 and DU145-DR cells, ECO/siHOTTIP treated DU145-TGF-β1 cells showed a significant reduction in their ability of migration and invasion, evidenced by the significantly reduced number of migrated cells stained in purple compared with those treated with ECO/siNS (FIG. 37).

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A nanosized complex comprising siRNA and a compound comprising formula (I):

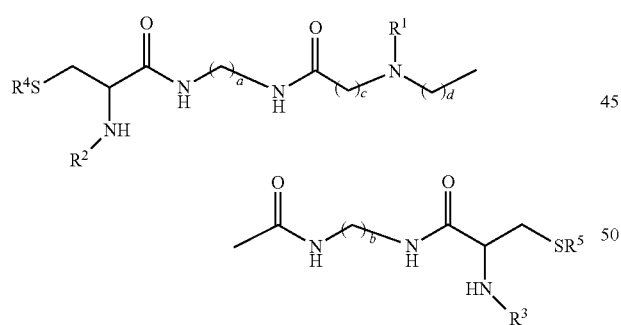

wherein $R^1$ is an alkylamino group or a group containing at least one aromatic group;

$R^2$ and $R^3$ are independently an aliphatic group or a hydrophobic group;

$R^4$ and $R^5$ are independently H, a substituted or unsubstituted akyl alkyl group, an alkenyl group, an acyl group, an aromatic group, polymer, a targeting group, or a detectable moiety;

a, b, c, and d are independently an integer from 1 to 10; and pharmaceutically acceptable salts thereof.

2. The nanosized complex of claim 1, wherein $R^1$ comprises at least one of:

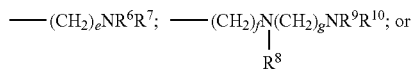

where $R^6$, $R^7$, $R^8$, $R^9$, $R^{10}$, $R^{11}$, $R^{12}$, $R^{13}$, and $R^{14}$ are independently hydrogen, an alkyl group, a hydrophobic group, or a nitrogen containing substituent; and e, f, g, i, j, k, and l, are an integer from 1 to 10.

3. The nanosized complex of claim 1, wherein $R^2$ and $R^3$ are independently a hydrophobic group derived from oleic acid or linoleic acid.

4. The nanosized complex of claim 3, wherein $R^2$ and $R^3$ are the same.

5. The nanosized complex of claim 1, wherein $R^4$ and $R^5$ are independently H, a substituted or unsubstituted polymer, a targeting group, or a detectable moiety.

6. The nanosized complex of claim 1, wherein a, b, c, and d are each 2.

7. The nanosized complex of claim 1, $R^1$ comprises $CH_2CH_2NH_2$.

8. The nanosized complex of claim 1, wherein the compound is

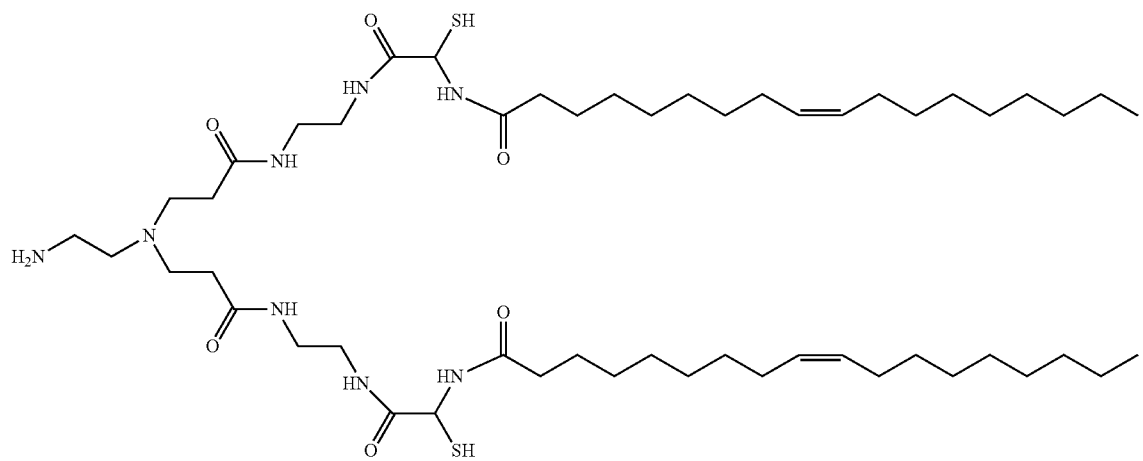

(ECO) or

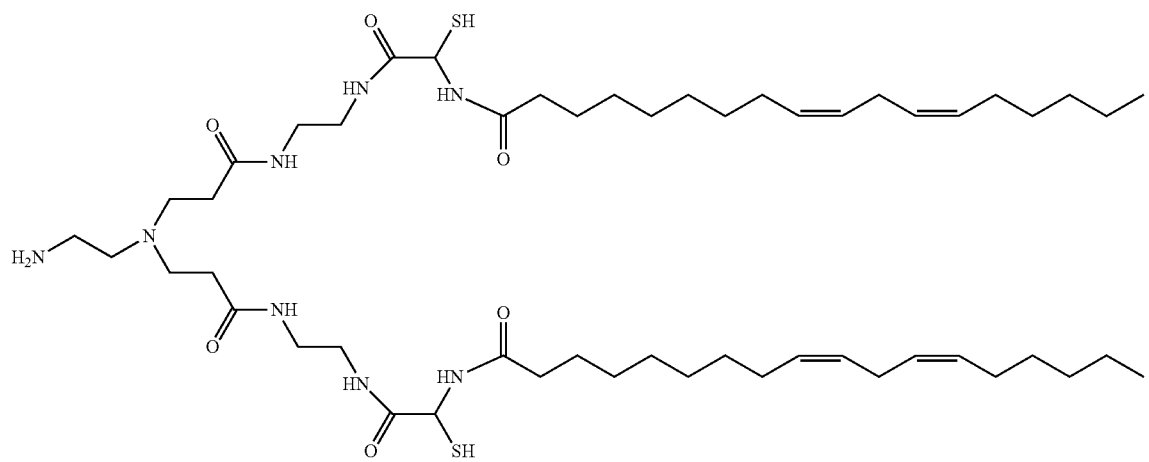

(ECLn)

9. The nanosized complex of claim 1, wherein polyethylene glycol is covalently attached to the compound.

10. The nanosized complex of claim 1, wherein the targeting group is covalently attached to the compound by a linker.

11. The nanosized complex of claim 10, wherein the linker comprises a polyamino acid group, a polyalkylene group, or a polyethylene glycol group.

12. The nanosized complex of claim 10, wherein the targeting group comprises a peptide, a protein, an antibody, or an antibody fragment.

13. The nanosized complex of claim 11, wherein the linker comprises an acid labile bond.

14. The nanosized complex of claim 1, wherein the siRNA inhibits expression of an lncRNA upon delivery of the nanosized complex to a cell.

15. The nanosized complex of claim 14, wherein the lncRNA is an onco-lncRNA.

16. A method of treating cancer in a subject in need thereof, the method comprising:

administering to the subject a nanosized complex comprising siRNA and a compound comprising formula (I):

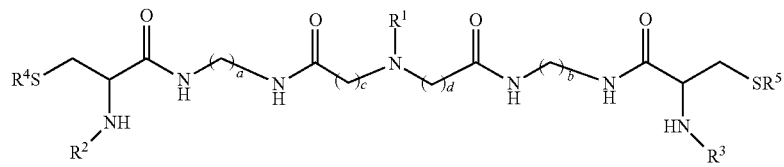

wherein $R^1$ is $CH_2CH_2NH_2$;
$R^2$ and $R^3$ are independently an aliphatic group or a hydrophobic group;
$R^4$ and $R^5$ are independently H, a substituted or unsubstituted alkyl group, an alkenyl group, an acyl group, an aromatic group, polymer, a targeting group, or a detectable moiety;

a, b, c, and d are independently an integer from 1 to 10; and pharmaceutically acceptable salts thereof.

17. The method of claim 16, wherein $R^2$ and $R^3$ are independently a hydrophobic group derived from oleic acid or linoleic acid.

18. The method of claim 16, wherein the compound is

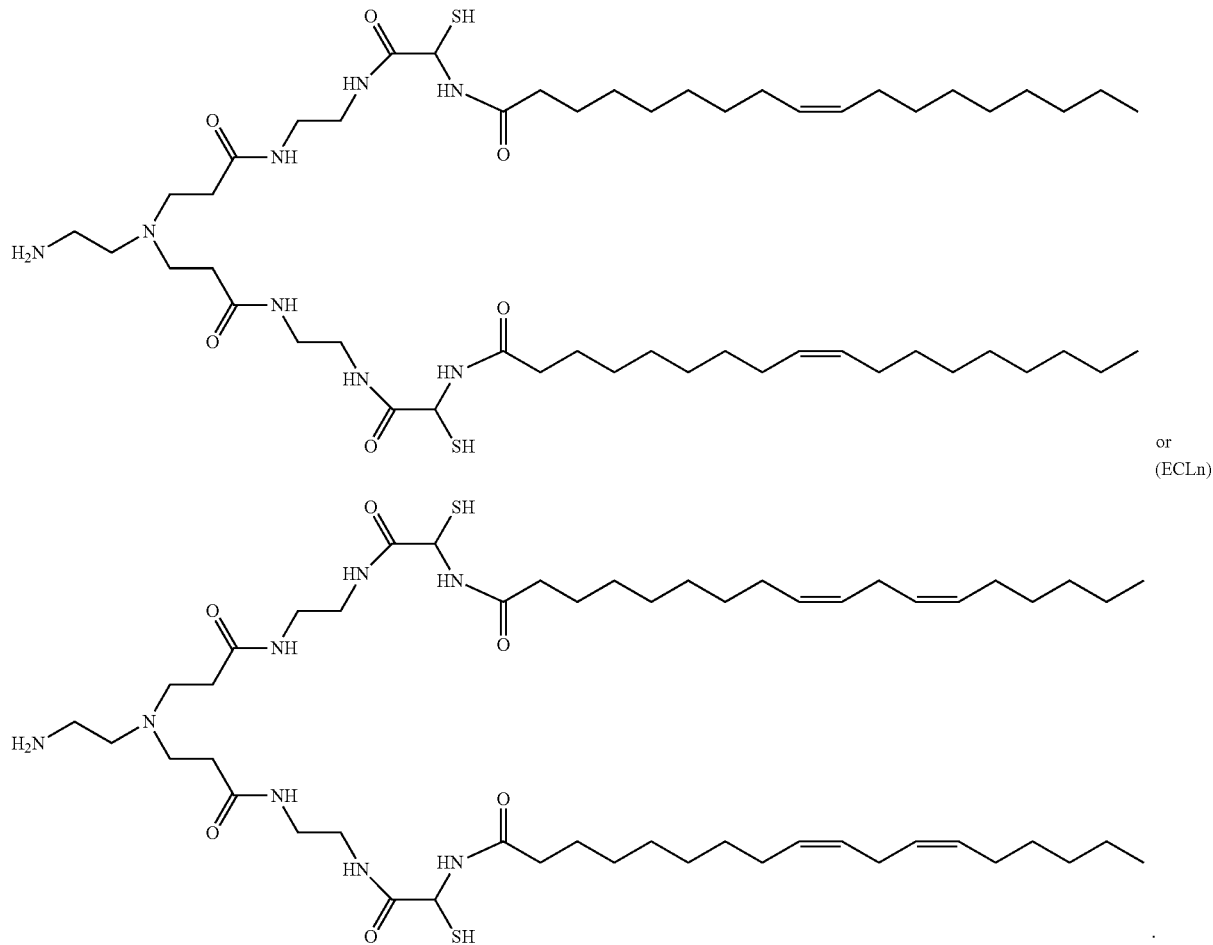

(ECO)

or (ECLn)

19. The method of claim 16, wherein the siRNA inhibits expression of an lncRNA upon delivery of the nanosized complex to a cell.

20. The method of claim 16, wherein the lncRNA is an onco-lncRNA.

* * * * *